(12) United States Patent
Zheng et al.

(10) Patent No.: US 10,332,616 B2
(45) Date of Patent: Jun. 25, 2019

(54) MOVABLE TYPE METHOD APPLIED TO PROTEIN-LIGAND BINDING

(71) Applicants: University of Florida Research Foundation, Inc., Gainesville, FL (US); Board of Trustees of Michigan State University, East Lansing, MI (US)

(72) Inventors: Zheng Zheng, Gainesville, FL (US); Kenneth M. Merz, Jr., Ann Arbor, MI (US)

(73) Assignees: Board of Trustees of Michigan State University, East Lansing, MI (US); University of Florida Research Foundation, Inc., Gainesville, FL (US)

(*) Notice: Subject to any disclaimer, the term of this patent is extended or adjusted under 35 U.S.C. 154(b) by 467 days.

(21) Appl. No.: 15/143,519

(22) Filed: Apr. 30, 2016

(65) Prior Publication Data

US 2016/0350474 A1    Dec. 1, 2016

Related U.S. Application Data

(63) Continuation-in-part of application No. PCT/US2014/063328, filed on Oct. 31, 2014.

(Continued)

(51) Int. Cl.
*G06F 7/60* (2006.01)
*G16B 5/00* (2019.01)
(Continued)

(52) U.S. Cl.
CPC ............... *G16B 5/00* (2019.02); *G01N 33/68* (2013.01); *G06F 17/18* (2013.01);
(Continued)

(58) Field of Classification Search
CPC ...... G06F 19/706; G06F 19/708; G06F 19/16; G06F 17/5018
(Continued)

(56) References Cited

U.S. PATENT DOCUMENTS 6,178,384 B1 *    1/2001    Kolossváry ........... G06F 19/704
                                                                    702/27
2003/0215959 A1    11/2003    Jayaraman
(Continued)

FOREIGN PATENT DOCUMENTS

WO    WO-2015066415 A1    5/2015

OTHER PUBLICATIONS

D. L. Beveridge, Free Energy Via Molecular Simulation: Applications to Chemical and Biomolecular Systems, (Year: 1989).*

(Continued)

*Primary Examiner* — Lechi Truong
(74) *Attorney, Agent, or Firm* — Schwegman Lundberg & Woessner, P.A.

(57) ABSTRACT

Disclosed herein is a method of estimating the pose of a ligand in a receptor comprising identifying all possible atom pairs of protein-ligand complexes in a given configuration space for a system that comprises proteins; creating a first database and a second database; where the first database comprises associated pairwise distant dependent energies and where the second database comprises all probabilities that include how the atom pairs can combine; combining the first database with the second database via statistical mechanics to accurately estimate binding free energies as well as a pose of a ligand in a receptor; and selecting a protein-ligand complex for further study.

26 Claims, 27 Drawing Sheets

Related U.S. Application Data

(60) Provisional application No. 61/898,718, filed on Nov. 1, 2013.

(51) Int. Cl.
*G06F 17/50* (2006.01)
*G16B 15/00* (2019.01)
*G16C 20/50* (2019.01)
*G01N 33/68* (2006.01)
*G06F 17/18* (2006.01)
*G16C 20/90* (2019.01)

(52) U.S. Cl.
CPC ......... *G06F 17/5018* (2013.01); *G16B 15/00* (2019.02); *G16C 20/50* (2019.02); *G16C 20/90* (2019.02)

(58) Field of Classification Search
USPC .......................................................... 703/2
See application file for complete search history.

(56) References Cited

U.S. PATENT DOCUMENTS

2008/0243452 A1* 10/2008 Bowers ................ G06F 19/701
703/2
2010/0112724 A1  5/2010 Tovbin et al.

OTHER PUBLICATIONS

"International Application Serial No. PCT/US2014/063328, International Search Report dated Feb. 5, 2015", 3 pgs.
"International Application Serial No. PCT/US2014/063328, Written Opinion dated Feb. 5, 2015", 7 pgs.
Gallicchio, et al., "Advances in all atom sampling methods for modeling protein-ligand binding affinities", Current Opinion in Structural Biology, vol. 21, No. 2,, (2011), 161-166.
Gilson, et al., "Calculation of protein-ligand binding affinities", The Annual Review of Biophysics and Biomolecular Structure, vol. 36, (2007), 21-42.
Zheng, et al., "The movable type method applied to protein-ligand binding", Journal of Chemical Theory and Computation, vol. 9, No. 12, (Oct. 28, 2013), 5526-5538.

* cited by examiner

MOVABLE TYPE METHOD APPLIED TO PROTEIN-LIGAND BINDING

CROSS-REFERENCE TO RELATED APPLICATIONS

This application is a continuation-in-part under 35 U.S.C. § 1.111 (a) of PCT application No. PCT/US2014/063328, filed Oct. 31, 2014, which claims the benefit of the priority to U.S. Provisional Application No. 61/898,718 filed on Nov. 1, 2013, the entire contents of which applications are incorporated herein by reference.

STATEMENT REGARDING FEDERALLY SPONSORED RESEARCH

This invention was made with government support GM044974, under GM066859, and under GM0112406 awarded by the National Institutes of Health. The government has certain rights in the invention.

COPYRIGHT NOTICE

A portion of the disclosure of this patent document contains material that is subject to copyright protection. The copyright owners have no objection to the facsimile reproduction by anyone of the patent document or the patent disclosure, as it appears in the United States Patent and Trademark Office patent files or records, but otherwise reserves all copyright rights whatsoever. The following notice applies to the software, pseudocode, and data as described below and in the drawings that form a part of this document: Copyright University of Florida and Michigan State University. 2016, All Rights Reserved.

BACKGROUND

This disclosure relates to movable type method applied to protein-ligand binding.

Accurately computing the free energy for biological processes like protein folding or protein-ligand association remains a challenging problem. Both describing the complex intermolecular forces involved and sampling the requisite configuration space make understanding these processes innately difficult. It is therefore desirable to address the sampling problem so as to accurately and efficiently estimate binding free energies as well as the pose of a ligand in a receptor.

SUMMARY

Disclosed herein is a method of estimating the pose of a ligand in a receptor comprising identifying all possible atom pairs of protein-ligand complexes in a given configuration space for a system that comprises proteins; creating a first database and a second database; where the first database comprises associated pairwise distant dependent energies and where the second database comprises all probabilities that include how the atom pairs can combine; combining the first database with the second database via statistical mechanics to accurately estimate binding free energies as well as a pose of a ligand in a receptor; and selecting a protein-ligand complex for further study.

Disclosed herein too is a system comprising a device; where the device is effective to estimate a pose of a ligand in a receptor comprising identifying all possible atom pairs of protein-ligand complexes in a given configuration space for a system that comprises proteins; creating a first database and a second database; where the first database comprises associated pairwise distant dependent energies and where the second database comprises all probabilities that include how the atom pairs can combine; combining the first database with the second database via statistical mechanics to accurately estimate binding free energies as well as the pose of the ligand in the receptor; and selecting a protein-ligand complex for further study.

Also disclosed herein is a method for verifying the binding characteristics of a protein and a ligand using a computer, comprising the steps of: collecting and maintaining a database containing atom pairwise energy data, assembling said atom pairwise data in a printing forme, introducing a fixed-size Z-matrix which represents a Boltzmann-weighted energy ensemble in association with said printing forme, and further assembling atom pairwise energies at different distances using said printing forme so as simultaneously to represent both ensemble and free energies of said protein and said ligand, and rendering said ensemble and free energies as an output to a user to verify binding characteristics of said protein and said ligand.

Also disclosed herein is (i) a computer-implemented method of simulating free energy change with respect to one or a series of molecules that can include the following; (ii) one or more computer-readable hardware storage device having embedded therein a set of instructions which, when executed by one or more processors of a computer, causes the computer to execute operations that can include the following; and (iii) a system comprising one or more hardware computer processor configured to do the following:

determining, using at least one hardware computer processor, atom pairwise contacts between a first molecule structure and a second molecule structure;

sampling atom energy for the two-molecule system and constructing an atom energy matrix for the first molecule and an atom-energy matrix for the second molecule;

converting the atom energy matrix for the first molecule into a molecular energy matrix for the first molecule;

converting the atom energy matrix for the second molecule into a molecular energy matrix for the second molecule;

converting energy values of the molecular energy matrix for the first molecule to Boltzman factors under room temperature;

converting energy values of the molecular energy matrix for the second molecule to Boltzman factors under room temperature;

using the Boltzman factors, calculating Boltzmann free energy $$A = -RT \ln[Z_M] = -RT \ln\left[\int_D e^{-\beta E_M(\tau)} d\tau\right] \approx -RT \ln\left[V \frac{\sum_i^N e^{-\beta E_i(r)}}{N}\right]$$

where:
R is the gas constant;
T is temperature in degrees Kelvin (optionally 298.15 K);
Z is the partition function, which is the sum of the Boltzman factors;
D is a defined volume quantity representing the three dimensional space that particles under study should be contained;

M is a subscription meaning "molecular";
β is 1/(RT):
E is the energy;
V is the ensemble volume; and
N is the number of states that have been sampled;
using Monte Carlo Integration by a method that comprises calculating an estimate of the ensemble volume V according to the equation:

$$V = 2^{Y-4} \times (2\pi)^{Y-3} \times (4\pi)^{Y-2} C^{Y-1}$$

where:
C a constant represent ing a predetermined boundary of the particle-particle distance in the ensemble, and
Y is the number of atoms in the ensemble.

BRIEF DESCRIPTION OF THE FIGURES

FIG. 16A shows KMTISM calculated solvation free energies (kcal/mol) vs. experimental data for hydrocarbon test sets. FIG. 16B shows MM-GBSA calculated solvation free energies (kcal/mol) vs. experimental data for hydrocarbon test sets. FIG. 16C shows MM-PBSA calculated solvation free energies (kcal/mol) vs. experimental data for hydrocarbon test sets. FIG. 16D shows KMTISM calculated solvation free energies (kcal/mol) vs. experimental data for oxygen-bearing test sets. FIG. 16E shows MM-GBSA calculated solvation free energies (kcal/mol) vs. experimental data for oxygen-bearing test sets. FIG. 16F shows MM-PBSA calculated solvation free energies (kcal/mol) vs. experimental data for oxygen-bearing test sets. FIG. 16G shows KMTISM calculated solvation free energies (kcal/mol) vs. experimental data for halocarbon test sets. FIG. 16H shows MM-GBSA calculated solvation free energies (kcal/mol) vs. experimental data for halocarbon test sets. FIG. 16I shows MM-PBSA calculated solvation free energies (kcal/mol) vs. experimental data for halocarbon test sets;

FIG. 17A shows KMTISM calculated solvation free energies (kcal/mol) vs. experimental data for amide test sets. FIG. 17B shows MM-GBSA calculated solvation free energies (kcal/mol) vs. experimental data for amide test sets. FIG. 17C shows MM-PBSA calculated solvation free energies (kcal/mol) vs. experimental data for amide test sets. FIG. 17D shows KMTISM calculated solvation free energies (kcal/mol) vs. experimental data for organosulfur and organophosphorus test sets. FIG. 17E shows MM-GBSA calculated solvation free energies (kcal/mol) vs. experimental data for organosulfur and organophosphorus test sets. FIG. 17F shows MM-PBSA calculated solvation free energies (kcal/mol) vs. experimental data for organosulfur and organophosphorus test sets. FIG. 17G shows KMTISM calculated solvation free energies (kcal/mol) vs. experimental data for polyfunctional test sets. FIG. 17H shows MM-GBSA calculated solvation free energies (kcal/mol) vs. experimental data for polyfunctional test sets. FIG. 17I shows MM-PBSA calculated solvation free energies (kcal/mol) vs. experimental data for polyfunctional test sets;

FIG. 18A shows KMTISM calculated solvation free energies (kcal/mol) vs. experimental data for carboxylate and charged amine test sets. FIG. 18B shows MM-GBSA calculated solvation free energies (kcal/mol) vs. experimental data for carboxylate and charged amine test sets. FIG. 18C shows MM-PBSA calculated solvation free energies (kcal/mol) vs. experimental data for carboxylate and charged amine test sets.

DETAILED DESCRIPTION

Figure 1:
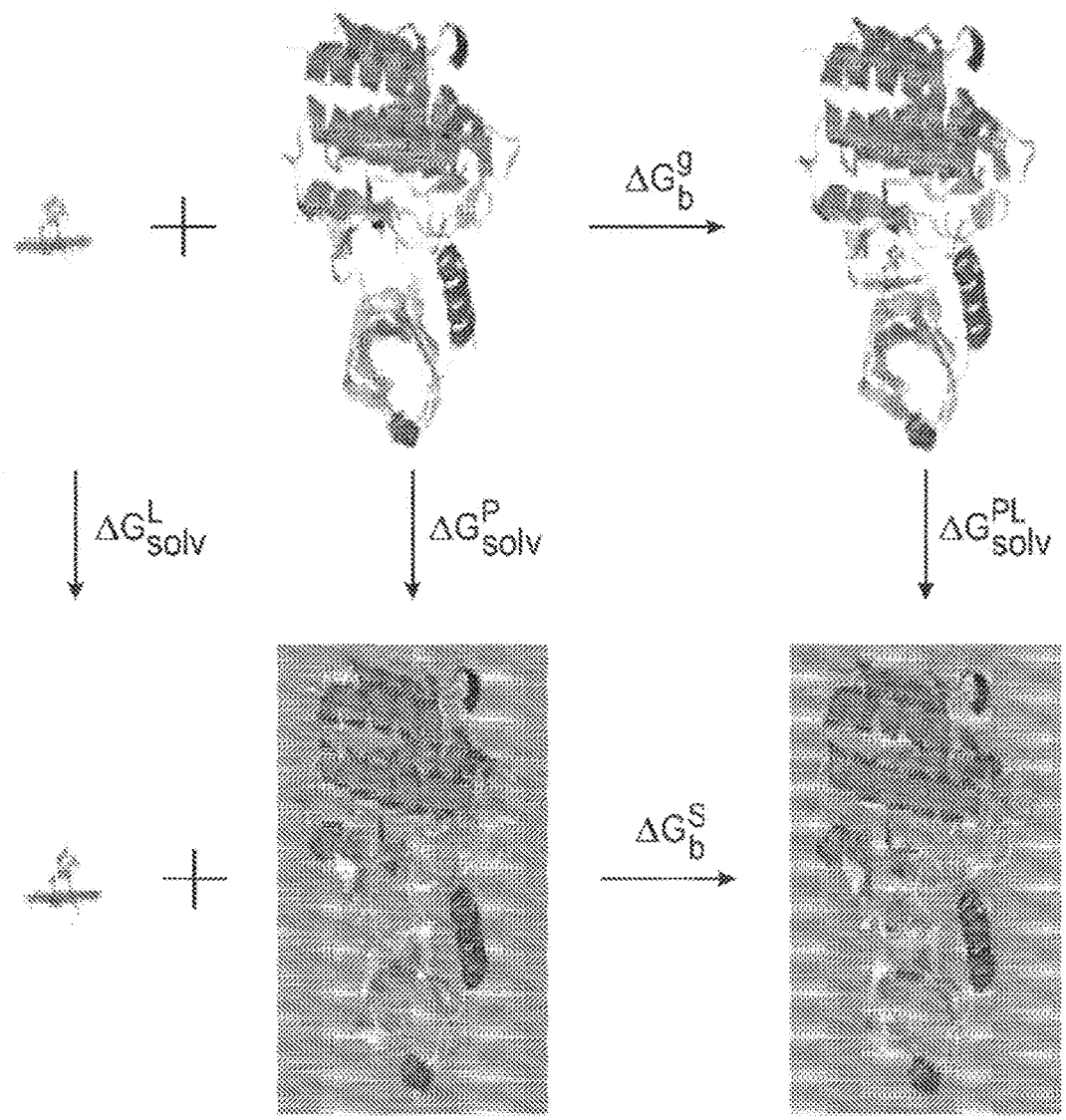
FIG. 1 depicts the thermodynamic cycle used to formulate the free energy of protein-ligand binding in solution, according to some example embodiments.

Disclosed herein is a method for addressing the sampling problem using a novel methodology called "movable type". Conceptually it can be understood by analogy with the evolution of printing and, hence, the name movable type. For example, a common approach to the study of protein-ligand complexation involves taking a database of intact drug-like molecules and exhaustively docking them into a binding pocket. This is reminiscent of early woodblock printing where each page had to be laboriously created prior to printing a book. However, printing evolved to an approach where a database of symbols (letters, numerals, and the like) was created and then assembled using a movable type system, which allowed for the creation of all possible combinations of symbols on a given page, thereby, revolutionizing the dissemination of knowledge.

The movable type (MT) method involves an identification of all atom pairs seen in protein-ligand complexes and then creating two databases: one with their associated pairwise distant dependent energies and another associated with the probability of how these pairs can combine in terms of bonds, angles, dihedrals and non-bonded interactions. Combining these two databases coupled with the principles of statistical mechanics allows us to accurately estimate binding free energies as well as the pose of a ligand in a receptor. This method, by its mathematical construction, samples all of configuration space of a selected region in a single effort without resorting to brute force sampling schemes involving Monte Carlo, genetic algorithms or molecular dynamics simulations making the methodology extremely efficient. Importantly, this method explores the free energy surface eliminating the need to estimate the enthalpy and entropy components individually. Finally, low free energy structures can be obtained via a free energy minimization procedure yielding all low free energy poses on a given free energy surface. Besides revolutionizing the protein-ligand docking and scoring problem this approach can be utilized in a wide range of applications in computational biology which involves the computation of free energies for systems with extensive phase spaces including protein folding, protein-protein docking and protein design. The method permits the selection of particular proteins and ligands for use in experiments, in manufacturing, in therapy, in drugs, in drug trials, in artificial parts, or a combination thereof. In other words, the determination of free energies between proteins and ligands permits the selection of protein-ligand pairs that can effectively function for various desired purposes. The computations disclosed below can be conducted on a computer or a microprocessor, with the most probable protein-ligand pairs being detailed on a computer screen, a paper print-out, a hard drive, a flash drive, and the like.

Sampling the configuration space of complex biomolecules is a major hurdle impeding the ability to advance the understanding of a diverse range of processes including protein folding and the accurate prediction of ligand binding to a biological receptor. Major advances have been made in computer hardware, which has allowed molecular dynamics (MD) simulations to reach the millisecond barrier, but this method is brute force in nature and uses highly sophisticated hardware and software. Moreover, a major hurdle in the modeling of biological systems is associated with how the inter and intra-molecular energies are modeled. Modern force fields are highly evolved, but still need to be further refined to reach chemical accuracy in many applications.

Predicting how a ligand (drug) binds to its receptor and predicting its associated binding affinity is a highly challenging problem, which if solved, would singularly advance modern structure-based drug design. This approach has largely employed so-called end-point methods that dock (place) a candidate molecule into a receptor and compute the binding free energy using a range of physics-based or empirical "scoring" functions. From an analysis of the error propagation properties in the statistical mechanics based prediction of protein-ligand binding affinities it was shown that the end-point class of approaches maximizes energy function uncertainties. This can be alleviated through the use of sampling approaches including MD methods or methods that exhaustively sample the configuration space associated with protein-ligand binding. These methods have shown that they can be successful, but are brute force in nature, which lead to the consideration of ways in which ideas more akin to the end-point methods, but incorporating sampling at the same time can be used. The concept being that this approach would provide a solution to the problem detailed above, while mitigating the effects of energy function deficiencies.

Using MD or exhaustive sampling procedures to evaluate protein-ligand binding is conceptually similar to woodblock printing technology where all the words (molecules) are carefully placed on a board (receptor site) and the whole book can be printed (binding free energy determined). While a more advanced printing technology, movable type printing, (which was invented in China in the 11th century and introduced by Gutenberg into the alphabetic language system) uses a "database" of letters that is pre-constructed and then the printing of any word involves a database search followed by the appropriate combination from the movable type system. Using a typical pairwise potential the molecular energy of a system can be decomposed into atom pairwise interaction energies including bond, angle, torsion, and long-range non-covalent forces (van der Waals and electrostatic forces), which by analogy to the MT systems is our database of "letters". Each interaction has a different intensity and probability of occurrence along an atom pairwise coordinate axis. Herein, is described the mathematics that can be used to bring end-point methods up to the "movable type printing level", via building a database of energy intensities and probabilities for all atom type pair interactions found in protein-ligand complexes. Using this information it can be demonstrated that the MT approach facilitates the ability to predict protein-ligand binding free energies and also allows the extracting of the associated low energy "poses" all at a fraction of the cost associated with "brute" force sampling methods. A pose- is a (one of many in practice) unique 3-D positioning of a ligand in a receptor pocket.

Moreover, the docking and scoring problem is an example of a broad class of problems in computational biology that involve both the computation of the free energy and structure of a biological system, which includes challenges like the prediction of protein folds, protein-protein interactions and protein design all of which the MT method can address.

The Movable Type Method Applied to Protein-Ligand Binding

A thermodynamic cycle modeling the binding free energy $\Delta G_b^s$ in solution (shown in FIG. 1) is typically employed in end-point methods:

$$\Delta G_b^s = \Delta G_b^g + \Delta G_{solv}^{PL} - \Delta G_{solv}^L - \Delta G_{solv}^P \quad (1)$$

where P and L indicate the protein and ligand, s and g represent the behavior in solution and the gas-phase, respectively, $\Delta G_{solv}$ is the solvation free energy, and $\Delta G_b$ is the binding free energy in gas (g) and solution (s), respectively.

Using $\Delta\Delta G_{solv} = \Delta G_{solv}^{PL} - \Delta G_{solv}^L - \Delta G_{solv}^P$, Equation 1 becomes:

$$\Delta G_b^s = \Delta G_b^g - \Delta\Delta G_{solv} \quad (2)$$

The binding free energy in solution is now separated into two terms: The binding free energy in the gas-phase and the change in the solvation free energy during the complexation process. At this point the moveable type algorithm is introduced to model both terms each with their own designs.

The binding free energy ($\Delta G_b^g$) in the gas-phase is one of the terms to evaluate in order to predict the protein-ligand binding affinity because it contains all interactions between the protein and ligand. When approximated as the Helmholtz free energy (NVT), the Gibbs (the canonical ensemble is used throughout, but the $\Delta G$ notation is predominantly used) binding free energy in the gas-phase can be generated using the ratio of the partition functions describing the protein-ligand complex, the protein, and the ligand.

$$\Delta G_b^g \approx \Delta A_b^g = -RT \ln\left[\frac{Z_{PL}}{Z_P Z_L}\right] = -RT \ln\left[\frac{\int e^{-\beta E_{PL}(r)} dr}{\int e^{-\beta E_P(r)} dr \int e^{-\beta E_L(r)} dr}\right] \quad (3)$$

where Z represents the canonical ensemble partition function, $E_{PL}$ is the energy of the protein-ligand interactions as a function of distance r, $E_P$ is the protein energy, $E_L$ is the ligand energy (both as a function of distance r) and $\beta$ is the reciprocal of the thermodynamic temperature $k_B T$. Partition functions are integrals over all possible coordinates of the protein-ligand complex, the protein, and the ligand. Equation 3 can be manipulated into the following form:

$$\Delta G_b^g = -RT \ln\left[\frac{F_{PL}\langle e^{-\beta E_{PL}(r)}\rangle}{F_P \langle e^{-\beta E_P(r)}\rangle F_L \langle e^{-\beta E_L(r)}\rangle}\right] \quad (4)$$

where the partition functions are expressed as the Boltzmann-weighted average of the pose energies (shown in brackets) multiplied the volume of configuration space available to each state, shown as F in Equation 4. $F_P$ and $F_L$ are the number of external degrees of freedom for the unbound protein and the unbound ligand respectively, $F_{PL}$ is approximated as the product of the external degrees of freedom (DoFs) of the bound protein and ligand (including the rotational and translational DoFs), and the internal DoFs of the bound protein and ligand (including the relative-positional and vibrational DoFs), given as:

$$F_{PL} = F_{boundP}^{external} F_{boundL}^{external} F_{boundP}^{internal} F_{boundL}^{internal} \quad (5)$$

Similarly, the DoFs of the free protein and ligand molecules are also separated into the external and internal components. Internal DoFs are identical for bound and free protein/ligand structures and the bound and free proteins are also assumed to share the same internal and external DoFs. Only the external DoFs of the ligand are differentiated between the bound and free systems. The rotational DoF of a free ligand is $8\pi^2$ on a normalized unit sphere. However, because of the inaccessible volume present in protein-ligand systems, the rotational DoFs of bound ligands are designated as $\alpha\pi^2$ with a to-be-determined average volume factor a less than 8. The translational DoFs are treated as a constant C, which is assumed to be identical for all free ligands, while the translational DoF for bound ligands is the volume of the binding pocket $V_{pocket}$ in which the ligands' center of mass can translate. Thereby, in the protein-ligand binding process, changes in the DoFs can be modeled as a constant with respect to the different volumes of the binding pockets ($V_{pocket}$). Applying these approximations we obtain:

$$\frac{F_{PL}}{F_P F_L} = \frac{F_{boundP}^{external} F_{boundL}^{external} F_{boundP}^{internal} F_{boundL}^{internal}}{F_{freeP}^{external} F_{freeP}^{internal} \times F_{freeL}^{external} F_{freeL}^{internal}} = \quad (6)$$

$$\frac{F_{boundL}^{external}}{F_{freeL}^{external}} = \frac{\alpha\pi^2 V_{pocket}}{8\pi^2 C} = \frac{aV_{pocket}}{8C}$$

The gas-phase protein-ligand binding free energy can then be further manipulated into the following form:

$$\Delta G_b^g = -RT \ln\left[\frac{aV_{pocket}\langle e^{-\beta E_{PL}(r)}\rangle}{8C\langle e^{-\beta E_P(r)}\rangle\langle e^{-\beta E_L(r)}\rangle}\right] \quad (7)$$

Again using the Helmholtz free energy approximation (Equation 3), the solvation free energy can be correlated to the partition function of the solute (protein, ligand or protein-ligand complex) and solute-solvent bulk interactions. In this way, the solvation free energy, using $\Delta G_{solv}^L$, as an example, is modeled as in Equation 8, and the DoFs are approximated as being the same for the solute and the solute-solvent bulk terms.

$$\Delta G_{solv}^L \approx \Delta A_{solv}^L = \quad (8)$$

$$-RT\ln\left[\frac{Z_{LS}}{Z_L}\right] = -RT\ln\left[\frac{\int e^{-\beta E_{LS}(r)} dr}{\int e^{-\beta E_L(r)} dr}\right] = -RT\ln\left[\frac{\langle e^{-\beta E_{LS}(r)}\rangle}{\langle e^{-\beta E_L(r)}\rangle}\right]$$

Finally, the remaining solvation terms given in Equation 1 ($\Delta G_{solv}^P$ and $\Delta G_{solv}^{PL}$) can be modeled in an analogous manner yielding the change in the solvation free energy as ligand binding occurs which then can be used to evaluate the overall free energy of ligand binding in aqueous solution.

Construction of the "Movable Type" System: Atom Pairwise Interaction Energy and Probability Databases With pose energies sampled over all possible DoFs for the bound and free protein/ligand system, the gas-phase protein-ligand binding free energy can be generated using molecular dynamics, Monte Carlo, genetic algorithms, and the like, by sampling over a large number of poses of the protein, ligand and protein-ligand complex. Using the canonical ensemble, the Helmholtz free energy (A) can be obtained as the arithmetic mean (sum of the energies of all ligand poses divided by the total number of all poses along with an estimate of integration volume) of Boltzmann factors:

$$G \approx A = -RT\ln[Z] = -RT\ln[\langle e^{-\beta E}\rangle] = -RT\ln\left[\frac{\sum_i e^{-\beta E_i}}{N}\right] \quad (9)$$

However, the problem of pose-based energy sampling lies in the fact that pose selection and sample size significantly affect the final result, not to mention that calculating many unique poses is very time-consuming. Different ligand poses have different energy preferences for the binding site, which leads to a range of binding probabilities. When calculating the averaged partition functions in Equation 7, one can assign probabilities (Q) as weights to different Boltzmann factors in order to differentiate the binding pocket preferences against ligand poses, rather than just simply using an arithmetic mean of all Boltzmann factors.

$$Q_i = \frac{e^{-\beta E}}{\sum_i e^{-\beta E_i}} \quad (10)$$

$$G \approx A = -RT\ln[Z] = -RT\ln[\langle e^{-\beta E}\rangle] = -RT\ln\left[\sum_i Q_i e^{-\beta E_i}\right] \quad (11)$$

The challenge in deriving the canonical partition function (as the denominator in Equation 10) for a protein-ligand system is that it is difficult to include all relevant ligand pose energies within the binding pocket using brute force sampling schemes. However, the task becomes much easier when a protein-ligand system is reduced to the atom-pair level. In this way the "pose" sampling problem can then can be cast as a 1-D rather than a 3-D problem by deriving the canonical partition function as a sum of the Boltzmann factor products of all atom pairwise energies included in the system over all atom pairwise separation distance ranges.

$$Z = \sum_i^{All\ Poses} Q_i e^{-\beta E_i} \quad (12)$$

$$= \sum_p^{All\ Combinations} \prod_q^{All\ atom\ points} Q_{pq} e^{-\beta E_{pq}}$$

$$= \sum_\alpha^{Bond\ Distance\ Range} \prod_a^{No.\ of\ Bonds} Q_{a\alpha} e^{-\beta E_{a\alpha}} \times$$

$$\sum_\beta^{Angle\ Distance\ Range} \prod_b^{No.\ of\ Angles} Q_{b\beta} e^{-\beta E_{b\beta}} \times$$

$$\sum_\gamma^{Torsion\ Distance\ Range} \prod_c^{No.\ of\ Torsions} Q_{c\gamma} e^{-\beta E_{c\gamma}} \times$$

$$\sum_\delta^{vdw\text{-}elec\ Distance\ Range} \prod_d^{No.\ of\ vdw\text{-}elec\ interactions} Q_{d\delta} e^{-\beta E_{d\delta}}$$

The canonical partition function can be derived following Equation 12, where the index "i" refers to each ligand pose (microstate) in a "traditional" brute force sampling scheme. When the protein-ligand system is broken down to the atom-pair level, "q" indicates all atom pairs in the molecular system, and "p" indicates each possible combination of all atom pairs each of which is at a pre-chosen distance. a, b, c and d refer to each atom pair as a bond, angle, torsion or long-range (van der Waals or electrostatic) interaction in the canonical system, respectively, and α, β, γ and δ refers to each sampled separation distance between the corresponding atom pair. Probabilities of all the atom pairwise distributions on the right hand side of Equation 12 are normalized as $$\left(\sum_i Q_i = \sum_i \frac{e^{-\beta E_i}}{\sum_i e^{-\beta E_i}} = 1\right):$$

$$\sum_\alpha^{Bond\ Distance\ Range} \prod_a^{No.\ of\ Bonds} Q_{a\alpha} \times \sum_\beta^{Angle\ Distance\ Range} \prod_b^{No.\ of\ Angles} Q_{b\beta} \times \quad (13)$$

$$\sum_\gamma^{Torsion\ Distance\ Range} \prod_c^{No.\ of\ Torsions} Q_{c\gamma} \times$$

$$\sum_\delta^{vdw\text{-}elec\ Distance\ Range} \prod_d^{No.\ of\ vdw\text{-}elec\ interactions} Q_{d\delta} = 1$$

Hence the MT method is designed to decompose the molecular energy into atom pairwise energies, which then simplifies the energy sampling problem to the atom-pair level. The advantage of this idea lies in that (1) atom pairs can be categorized based on atom types and interaction types, e.g. bond, angle, torsion, and long-range non-covalent interactions; (2) Calculation of atom pairwise energies is extremely cheap. Thereby, it is easy to build an atomic pairwise interaction matrix of energy vs. distance for each interaction type and atom pair type i, j. Hence, the energy calculation for each molecule is no more than a combination of elements from different energy matrices. In addition, the MT method is a template by which any pairwise decomposable energy function can be used. In the current work, the energy for each interaction type between a certain atom type pair i, j is calculated using the Knowledge-based and Empirical Combined Scoring Algorithm (KECSA) potential function. In KECSA, the protein-ligand statistical potential is modified and equated to an atom pairwise energy in order to generate force field parameters for bond stretching, angle bending, dihedral torsion angles and long-range non-covalent interactions.

Along with the distance-based energy, each atom pair type also has a distance preference encoded in its distribution, resulting in different probabilities associated with Boltzmann factors for each sampled atom pairwise distance. Atom-pair radial distributions were collected from a protein-ligand structure training set (i.e., the PDBbind v2011 data set with 6019 protein-ligand structures) and utilized in the current model. The atom pairwise radial distribution function is modeled as:

$$g_{ij}(r) = \frac{n_{ij}(r)}{n_{ij}^*(r)} = \frac{n_{ij}(r)}{\frac{N_{ij}}{V} 4\pi r^a \Delta r} \quad (14)$$

where $n_{i,j}(r)$ is the number of protein-ligand pairwise interactions between a certain atom pair type i and j in the bin (r, r+Δr), with the volume $4\pi r^a \Delta r$ collected from the training set. $n_{ij}^*(r)$ in the denominator mimics the number of protein-ligand atom type pairs i and j in the same distance bin in an ideal gas state. This removes the "non-interacting" background distribution from the protein-ligand system. Δr is defined as 0.005 Å. $N_{ij}$ is the total number of atom pairs of type i and j. The average volume V of the protein-ligand binding sites is given as $$\frac{4}{a+1}\pi R^{a+1},$$

with the same to-be-determined parameter a as described above (Equations 7 and 14). A cutoff distance R is assigned to each atom type pair defining the distance at which the atom pairwise interaction energy can be regarded as zero. Both a and R can be derived using a previously introduced method. The radial distribution frequency is then normalized by dividing the sum of radial distributions of all the atom pairs in the system (Equation 15).

$$q_{ij}(r) = \frac{g_{ij}(r)}{\sum_i \prod_j g_{ij}(r)} = \frac{\frac{R^{a+1}n_{ij}(r)}{(a+1)N_{ij}r^a\Delta r}}{\sum_i \prod_j \frac{R^{a+1}n_{ij}(r)}{(a+1)N_{ij}r^a\Delta r}} \quad (15)$$

In this way, the energy and distribution frequency vs. distance is calculated for any interaction type, and atom pair type, thereby, forming our MT database for later use.

Binding Free Energies from the "Movable Type" Method

Based on Equation 4, the binding free energy is defined as a ratio of partition functions of the different molecules involved in the binding process, i.e., the protein, ligand and the protein-ligand complex. Instead of sampling over poses of one molecule, the MT method simplifies the partition function of each system into a collection of partition functions (c) over each observed atom pair, which are equal to the normalized distribution probability of the atom type pair along the distance (q), multiplied by the corresponding atom pairwise partition function (z):

$$c = q \cdot z \quad (16)$$

By combining the partition functions c over all atom pairs in one molecule the partition function of one molecule averaged over all possible conformations is derived (Equation 17).

$$\langle e^{-\beta E(r)} \rangle = \sum_j^M \prod_i^N c_{ij}(r) \quad (17)$$

where the averaged molecular partition function is given as a sum of atom pairwise partition functions c sampled over distance intervals (M) of all combination of N atom pairs at all possible distances.

Starting from the protein-ligand complex database, the partition function matrices for the MT algorithm are constructed. When converted into a partition function matrix, the atom pairwise energy multiplier sampled as a function of distance is the basic element needed to assemble the total energy, as shown in Equation 18, using the protein bond energy as an example.

$$\mathbf{z}_k^{bond} = \begin{bmatrix} z_k^{bond}(r_1) \\ z_k^{bond}(r_2) \\ \vdots \\ z_k^{bond}(r_a) \\ \vdots \\ z_k^{bond}(r_n) \end{bmatrix} = \begin{bmatrix} e^{-\beta E_k^{bond}(r_1)} \\ e^{-\beta E_k^{bond}(r_2)} \\ \vdots \\ e^{-\beta E_k^{bond}(r_a)} \\ \vdots \\ e^{-\beta E_k^{bond}(r_n)} \end{bmatrix} \quad (18)$$

where subscript k indicates a bonded atom pair i and j, and each distance increment between any $r_a$ and $r_{a+1}$ is 0.005 Å. Using this scheme the distance sampling size is given by:

$$n = \frac{r_n - r_1}{0.005\text{Å}},$$

where $r_1$ and $r_n$ are the lower and upper bounds for distance sampling, which varies depending on the each atom pair and interaction type. The product over all bond-linked atom pairs derives the total bond partition function in the protein:

$$Z_P^{bond} = \mathbf{z}_1^{bond} \otimes \mathbf{z}_2^{bond} \otimes \mathbf{z}_3^{bond} \otimes \ldots \otimes \mathbf{z}_m^{bond} = \mathbf{z}_1^{bond} \cdot (\mathbf{z}_2^{bond})^T \cdot (\mathbf{z}_3^{bond})^T \ldots (\mathbf{z}_m^{bond})^T \quad (19)$$

$$Z_P^{bond} = \begin{bmatrix} z_1^{bond}(r_1)z_2^{bond}(r_1) \ldots z_m^{bond}(r_1) & z_1^{bond}(r_1)z_2^{bond}(r_1) \ldots z_m^{bond}(r_2) & \ldots & z_1^{bond}(r_1)z_2^{bond}(r_n) \ldots z_m^{bond}(r_n) \\ z_1^{bond}(r_2)z_2^{bond}(r_1) \ldots z_m^{bond}(r_1) & z_1^{bond}(r_2)z_2^{bond}(r_1) \ldots z_m^{bond}(r_2) & \ldots & z_1^{bond}(r_2)z_2^{bond}(r_n) \ldots z_m^{bond}(r_n) \\ \vdots & \vdots & \ddots & \vdots \\ z_1^{bond}(r_n)z_2^{bond}(r_1) \ldots z_m^{bond}(r_1) & z_1^{bond}(r_n)z_2^{bond}(r_1) \ldots z_m^{bond}(r_n) & \ldots & z_1^{bond}(r_n)z_2^{bond}(r_n) \ldots z_m^{bond}(r_n) \end{bmatrix} \quad (20)$$

In Equations 19 and 20, m indicates the total number of atom pairs that need to have their bond stretch term computed (i.e., number of covalent bonds), and n is the distance sampling size. T indicates the transpose. Thus, the matrix $Z_P^{bond}$ has a total of $n^m$ elements, and includes all combinations of the sampled atom pairwise distances and atom pairs (see Equation 20). Energy matrices for other kinds of atom pairwise interactions are assembled in the same way (i.e., bond, angle, torsion, and long-range interactions). A simple example is given in Example No. 1 below (butane-methane interaction), which illustrates the method in more detail. Products over these matrices generate the entire protein partition function matrix (Equation 21), representing all possible combinations of the protein internal energies with different atom pairwise distances.

$$Z_P \Box_P = Z_P^{bond} \otimes Z_P^{angle} \otimes Z_P^{torsion}$$
$$\otimes Z_P^{long\text{-}range} \tag{21}$$

$$\text{where } Z_P^{long\text{-}range} = Z_P^{vdw\text{-}elec} \otimes Z_P^{H\text{-}bond} \tag{22}$$

The KECSA van der Waals-electrostatic interaction models and hydrogen bond models are applied to the protein, ligand and protein-ligand complex systems. Similarly, the ligand energy (Equation 23) and protein-ligand interaction energy matrices (Equation 24) can be obtained.

$$Z_L \sqsubset_L = Z_L^{bond} \otimes Z_L^{angle} \otimes Z_L^{torsion}$$
$$\otimes Z_L^{long\text{-}range} \tag{23}$$

$$Z_{PL} \sqsubset_{PL} = Z_P^{bond} \otimes Z_P^{angle} \otimes Z_P^{torsion}$$
$$\otimes Z_P^{long\text{-}range} \otimes Z_L^{bond} \otimes Z_L^{angle}$$
$$\otimes Z_L^{torsion} \otimes Z_L^{long\text{-}range} \otimes Z_{PL}^{long\text{-}range} \tag{24}$$

The distribution frequency matrix is built in the same way, with the $q_{ij}(r)$ derived from Equation 15 as elements in each multiplier (also using the protein bond term as an example):

$$\mathbf{q}_k^{bond} = \begin{bmatrix} \mathbf{q}_k^{bond}(r_1) \\ \mathbf{q}_k^{bond}(r_2) \\ \mathbf{q}_k^{bond}(r_3) \\ \vdots \\ \mathbf{q}_k^{bond}(r_n) \end{bmatrix} \tag{25}$$

$$\mathcal{Q}_P^{bond} = \mathbf{q}_1^{bond} \otimes \mathbf{q}_2^{bond} \otimes \mathbf{q}_3^{bond} \otimes \ldots \otimes \mathbf{q}_k^{bond} \otimes \ldots \otimes \mathbf{q}_m^{bond} \tag{26}$$

$$Q_P \Box_P = \mathcal{Q}_P^{bond} \otimes \mathcal{Q}_P^{angle} \otimes \mathcal{Q}_P^{torsion} \otimes \mathcal{Q}_P^{long\text{-}range} \tag{27}$$

$$\text{where } \mathcal{Q}_P^{long\text{-}range} = \mathcal{Q}_P^{vdw\text{-}elec} \otimes \mathcal{Q}_P^{H\text{-}bond} \tag{28}$$

The distribution frequency matrix for the protein is derived using Equations 26 through 28, and the distribution frequency matrices of the ligand and protein-ligand intermolecular interactions are analogously derived as in Equations 29 and 30.

$$\mathbb{Q}\sqcap_L = \mathcal{Q}_L^{bond} \otimes \mathcal{Q}_L^{angle} \otimes \mathcal{Q}_L^{torsion}$$
$$\otimes \mathcal{Q}_L^{long\text{-}range}$$

$$\mathbb{Q}\sqsubset_{PL} = \mathcal{Q}_{PL}^{long\text{-}range} = \mathcal{Q}_{PL}^{vdw\text{-}elec} \otimes \mathcal{Q}_{PL}^{H\text{-}bond} \tag{29}$$

$$\mathbb{Q}^-_{PL} = \mathcal{Q}_P^{bond} \otimes \mathcal{Q}_P^{angle} \otimes \mathcal{Q}_P^{torsion}$$
$$\otimes \mathcal{Q}_P^{long\text{-}range} \otimes \mathcal{Q}_L^{bond} \otimes \mathcal{Q}_L^{angle}$$
$$\otimes \mathcal{Q}_L^{torsion} \otimes \mathcal{Q}_L^{long\text{-}range} \otimes \mathcal{Q}_{PL}^{long\text{-}range} \tag{30}$$

By choosing the same range and distance increment in both the energy and distribution frequency calculations it can be demonstrated that any $r_x$ ($x=1, 2, 3 \ldots$) in Equation 18 is the same as corresponding $r_x$ in Equation 25. Thus, the corresponding elements in all energy and distribution frequency matrices correlate with each other. The pointwise product over all matrices ensures that the energies and distribution frequencies with the same range and distance increment are combined into one element in the final matrix of the probability-weighted partition function of the protein-ligand complex ($\mathbb{C}_{PL}$ in Equation 31).

$$\mathbb{C}_{PL} = \mathbb{Q} \cdot \mathbb{Z} = \mathbb{Q}_{PL} \cdot \mathbb{Z}_{PL} \tag{31}$$

In the final matrix each element of $\mathbb{C}_{PL}$ is a value of the partition function of the protein-ligand complex multiplied by its probability based on its radial distribution forming the ensemble average. Finally, the sum of all elements of the matrix $\mathbb{C}_{PL}$ gives us the averaged partition function of the protein-ligand complex:

$$\therefore \text{Sum}(\mathbb{Q}) = 1;$$

$$\therefore \text{Sum}(\mathbb{C}_{PL}) = \text{Sum}(\mathbb{Q} \cdot \mathbb{Z}) = \langle e^{-\beta E_{PL}(r)} \rangle \tag{32}$$

where the first equation is the normalization statement for the probabilities. In this manner, the normalized averaged partition function of the protein-ligand complex is derived in Equation 32.

Following the same procedure, the averaged partition functions for the protein and ligand are generated as well:

$$\langle e^{-\beta E_P(r)} \rangle = \text{Sum}(\mathbb{C}_P) \tag{33}$$

$$\langle e^{-\beta E_P(r)} \rangle = \text{Sum}(\mathbb{C}_L) \tag{34}$$

Expanding the matrices, the protein-ligand binding free energy in the gas-phase is defined as in Equation 35, using the averaged partition functions of all three systems (protein, ligand, protein-ligand complex) derived above.

$$\Delta G_b^g = -RT\ln\left[\frac{aV_{pocket}\langle e^{-\beta E_{PL}(r)} \rangle}{8C\langle e^{-\beta E_P(r)}\rangle\langle e^{-\beta E_L(r)}\rangle}\right] \tag{35}$$

$$= -RT\left(\ln\left[\frac{aV_{pocket}}{8C}\right] + \ln\left[\frac{\sum_{ijk}^{I+J+K}(\tilde{Q}_i^P \tilde{Q}_j^L \tilde{Q}_k^{PL} \exp[-\beta(E_i^P + E_j^L + E_k^{PL})])}{\left(\sum_i^I Q_i^P \exp[-\beta E_i^P]\right)\left(\sum_j^J Q_j^L \exp[-\beta E_j^L]\right)}\right]\right)$$

In Equation 35, Q is the radial distribution frequency and E is the energy. i, j, k are the indices of the protein, ligand and protein-ligand complex, while I, J, K are the total number of protein, ligand and protein-ligand complex samples, respectively.

$$\sum_i^I Q_i^P = \sum_j^J Q_j^L = \sum_j^K Q_j^{PL} = 1 \cdot \tilde{Q}_i^P, \tilde{Q}_j^L,$$

and $\tilde{Q}_k^{PL}$ are standard distribution frequency matrices normalized over all three systems, in order to satisfy $$\sum_{ijk}^{I+J+K} \tilde{Q}_i^P \tilde{Q}_j^L \tilde{Q}_k^{PL} = 1.$$

In this way the protein-ligand binding free energy in the gas-phase is derived using our MT algorithm.

Determination of the change in the solvation energy as a function of the binding process is computed in a similar manner. To illustrate this we describe how we obtain the solvation free energy of the ligand, which is one component of $\Delta\Delta G_{solv}$ and by extension the other terms can be derived.

The ligand solvation free energy is obtained by decomposing the ligand-solvent bulk energy into the free ligand energy $E_L(r)$, the ligand-solvent polar interaction energy $E_{psol}(r)$, and the ligand-solvent non-polar interaction energy $E_{npsol}(r)$:

$$E_{LS}(r) = E_L(r) + E_{psol}(r) + E_{npsol}(r) \tag{36}$$

Solvent was approximated as a shell of even thickness around the ligand, in which the water molecules are evenly distributed. The solvent shell thickness was 6 Å, and the inner surface of the shell was 1.6 Å away from the ligand surface, which approximates the radius of a water molecule. Herein, for simplicity, the ligand-solvent polar interaction was considered as a surface (solvent accessible polar surface of the ligand)—surface (solvent bulk layer surface at a certain distance away from ligand) interaction, instead of a point-point interaction, i.e. atom pairwise interaction.

Using this model, the ligand polar atom-solvent interaction energy was modeled as a solvent accessible buried area (SABA) of the ligand polar atoms multiplied by the polar atom—oxygen interaction energy terms taken from KECSA, to simulate the ligand-solvent surface interaction energy. All SABA-weighted interaction energies along the solvent shell thickness, with a 0.005 Å increment were collected and stored. The ligand-solvent polar interaction Boltzmann factor multiplier was modeled using Equation 37, with k indicating each polar atom in the ligand, $r_1=1.6$ Å, which is the inner layer of the solvent shell and $r_n=6$ Å+1.6 Å=7.6 Å, which is the outer boundary layer of the solvent shell.

$$\mathbf{z}_k^{psol} = \begin{bmatrix} z_k^{psol}(r_1) \\ z_k^{psol}(r_2) \\ z_k^{psol}(r_3) \\ \vdots \\ z_k^{psol}(r_n) \end{bmatrix} = \begin{bmatrix} e^{-\beta(SABA)_k E_k^{psol}(r_1)} \\ e^{-\beta(SABA)_k E_k^{psol}(r_2)} \\ e^{-\beta(SABA)_k E_k^{psol}(r_3)} \\ \vdots \\ e^{-\beta(SABA)_k E_k^{psol}(r_n)} \end{bmatrix} \quad (37)$$

Figure 2:
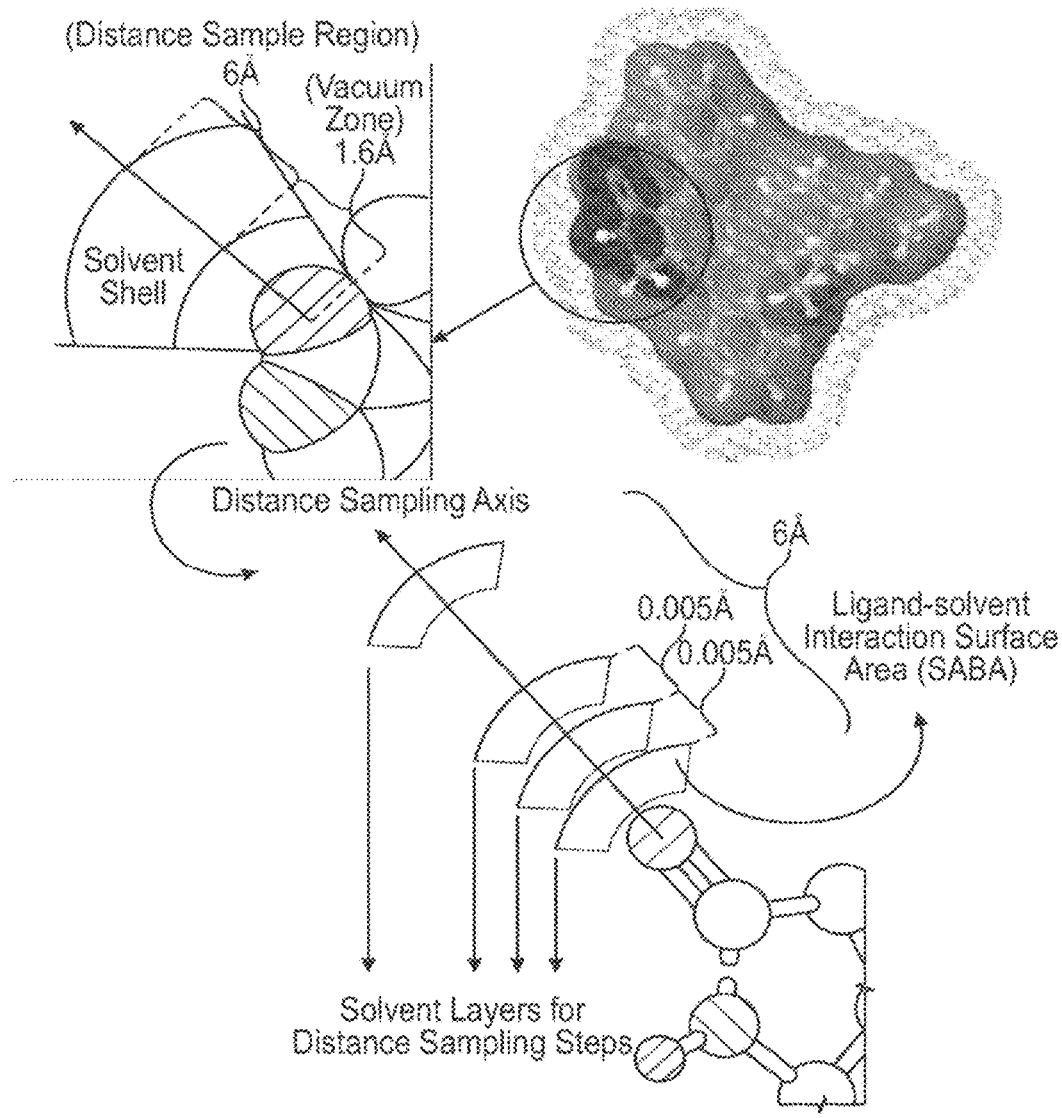
FIG. 2 shows modeling of ligand-solvent polar interaction using a Boltzmann factor multiplier, according to some example embodiments.

The ligand-solvent polar interaction Boltzmann factor matrix is then derived using Equation 38, covering all ligand polar atoms up to m. The distribution frequency matrices were not included in ligand-solvent energy calculation because the radial distribution function is approximated as being identical along all ligand-solvent distances (i.e. a featureless continuum). FIG. 2 further illustrates the modeling of the ligand-solvent polar interaction.

$$\mathbb{Z}\square_{psol} = \mathbf{z}_1^{psol} \cdot \left(\mathbf{z}_2^{psol}\right)_T \cdot \left(\mathbf{z}_3^{psol}\right)_T \ldots \left(\mathbf{z}_k^{psol}\right)_T \ldots \left(\mathbf{z}_m^{psol}\right)_T \quad (38)$$

FIG. 2 depicts the modelling of ligand-solvent polar interaction using a Boltzmann factor multiplier. A carbonyl oxygen atom is used and an example here. 1) The green surface shows the solvent accessible surface of the ligand (inner layer of the solvent shell). The surface consisting of blue dots represents the outer boundary surface of the solvent shell. 2) A close-up view of a selected polar atom (carbonyl oxygen) with its solvent shell. 3) Monte Carlo sampling along carbonyl oxygen—solvent shell layer distance.

The non-polar atom buried area (NABA) is used to simulate the interactions between the non-polar atoms and aqueous solvent, because the interaction energy between non-polar atoms and water molecules has a weaker response to changes in distance.

$$\mathbb{Z}_{npsol} = \left[ e^{-\beta NABA} \right] \quad (39)$$

The ligand energy is the same as was introduced in the gas-phase protein-ligand binding free energy calculation. So, the matrix for the ligand-solvent interaction energy is:

$$\mathbb{C}_{solv}^L = \mathbb{Z}_L \cdot \mathbb{Z}_{psol} \cdot \mathbb{Z}_{npsol} \quad (40)$$

$$\text{SUM}(\mathbb{C}_{solv}^L) = \text{SUM}\left(\mathbb{Z}_L \cdot \mathbb{Z}_{psol} \cdot \mathbb{Z}_{npsol}\right) = \left\langle e^{-\beta ELS(r)} \right\rangle \quad (41)$$

The solvation free energy was not fit to experimental solvation free energies and was found to have a small influence of the final binding free energies for the protein-ligand complexes. Nonetheless, future work will fit these models to small molecule solvation free energies, but for the present application the solvation model was used as formulated above.

With all necessary components constructed, the binding free energy in solution can be generated using:

$$\Delta G_b^s = \Delta G_b^g - \Delta \Delta G_{solv} \quad (42)$$

$$\Delta G_b^s = \Delta G_b^g + \Delta G_{solv}^{PL} - \Delta G_{solv}^P - \Delta G_{solv}^L$$

$$= -RT\ln\left[\frac{aV_{pocket}\langle e^{-\beta E_{PL}(r)}\rangle}{8C\langle e^{-\beta E_P(r)}\rangle\langle e^{-\beta E_L(r)}\rangle}\right] - RT\ln\left[\frac{\langle e^{-\beta E_{PLS}(r)}\rangle}{\langle e^{-\beta E_{PL}(r)}\rangle}\right] +$$

$$RT\ln\left[\frac{\langle e^{-\beta E_{PS}(r)}\rangle}{\langle e^{-\beta E_P(r)}\rangle}\right] + RT\ln\left[\frac{\langle e^{-\beta E_{LS}(r)}\rangle}{\langle e^{-\beta E_L(r)}\rangle}\right]$$

$$= -RT\ln\left[\frac{aV_{pocket}\langle e^{-\beta E_{PLS}(r)}\rangle}{8C\langle e^{-\beta E_{PS}(r)}\rangle\langle e^{-\beta E_{LS}(r)}\rangle}\right]$$

$$= -RT\left(\ln\left[\frac{aV_{pocket}}{8C}\right] + \ln\left[\frac{\sum_{ijk}^{I+J+K}\left(\tilde{Q}_i^P \tilde{Q}_j^L \tilde{Q}_k^{PL}\exp\left[-\beta\left(\begin{array}{c}E_i^P + E_j^L + E_k^{PL} + \\ E_s^{PLpsol} + NABA^{PL}\end{array}\right)\right]\right)}{\left(\sum_i^I Q_i^P \exp\left[-\beta E_i^P + E_s^{Ppsol} + NABA^P\right]\right)\left(\sum_{js}^{J+S} Q_j^L \exp\left[-\beta(E_j^L + E_s^{Lpsol} + NABA^L)\right]\right)}\right]\right)$$

Performance of MT KECSA as a Scoring Function for Protein-Ligand Binding Affinity Prediction Using the MT method we performed binding free energy calculations with the KECSA model and its associated parameters. This validation study was performed to illustrate (1) the general performance of MT method when used to predict protein-ligand binding affinities and (2) whether sampling along atom pairwise distance improves scoring performance, as done in MT KECSA, improves the prediction over the original KECSA method.

A test set containing 795 protein-ligand complexes was chosen from the PDBbind v2011 refined dataset based on the following criteria:
  (1) Crystal structures of all selected complexes had X-ray resolutions of <2.5 Å.
  (2) Complexes with molecular weights (MWs) distributed from 100 to 900 were selected, to avoid ligand size-dependent prediction results.
  (3) Complexes with ligands who have more than 20 hydrogen donors and acceptors, more than one phosphorus atom, and complexes with metalloproteins were excluded.

MT KECSA calculations show improvements in Pearson's r, Kendall τ and RMSE (Root-Mean-Square Error) when compared to the original KECSA model (Table 1). Importantly, judging from the slope and intercept of both calculations versus experimental data, MT KECSA (with slope of 0.85 and intercept of 0.14) better reproduces the binding affinities in the low and high affinity regions than the original KECSA model (with slope of 0.27 and intercept of 3.57). In the original KECSA approach, the entropy terms were empirically trained, thus, its test results demonstrate training-set dependence to some degree. Because complexes with medium binding affinities are more commonly seen in the PDB database when compared to complexes with high or low binding affinities, they become the majority in a large training set (1982 protein-ligand complexes were used to fit the original KECSA entropy terms). This causes the trained scoring functions to overestimate the binding affinity of the low-binding complexes while underestimating that of the high-binding complexes. On the other hand, MT KECSA, using canonical partition functions to compute the binding free energies, bypasses the difficulty of empirically building the entropy term, and, thereby, better reproduces the binding affinity in low and high binding free energy regions.

TABLE 1

Statistical results for MT KECSA and original KECSA correlated with experimental binding affinities.

|  | Pearson's r | RMSE(p$K_d$) | Kendall τ |
|---|---|---|---|
| MT KECSA | 0.72 | 1.88 | 0.53 |
| original KECSA | 0.62 | 2.03 | 0.46 |

Figure 3:
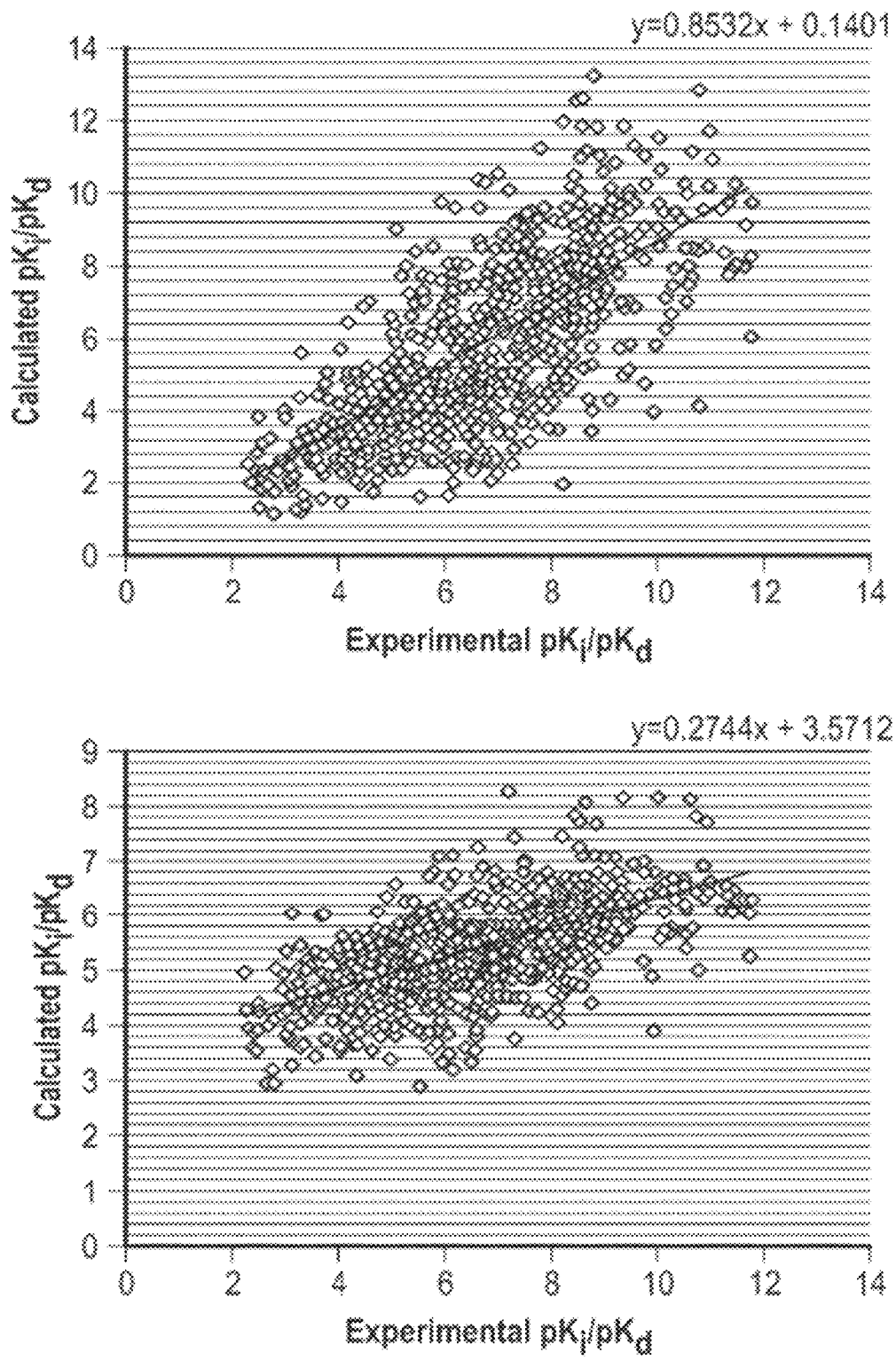
FIG. 3 depicts a plot of a movable type (MT) Knowledge-based and Empirical Combined Scoring Algorithm (KE-CSA; upper panel) model and the original KECSA model (lower panel) calculated pKd or pKi vales vs. Experimental pKd or pKi values, according to some example embodiments.

FIG. 3 depicts plots of MT KECSA (left) and the original KECSA model (right) calculated p$K_d$ or p$K_i$ vales vs. experimental p$K_d$ or p$K_i$ values.

Extracting Heat Maps from the Movable Type Method

Grid based methods and their graphical representation have had a long tradition in computer-aided drug design. For example COMFA creates a field describing the chemical nature of the active site pocket and the GRID algorithm uses a grid based approach to aid in molecular docking and has been adopted by other docking programs (e.g., GLIDE).

The very nature of the MT method permits the ready generation of "heat maps" describing the chemical nature of the grid points created in the MT method. These can be used to describe pairwise interactions between the grid-point and the protein environment (e.g., amide hydrogen with a carbonyl oxygen) or interactions can be lumped into nonpolar or polar interactions describing the aggregate collection of polar and non-polar pairwise interactions. Not only does this describe the nature of the grid points it also indicates regions where specific atoms should be placed to optimize binding affinity.

In contrast to energy heat maps, the MT heat maps represent the probability-weighted interaction energy on each grid point. Knowledge-based data (i.e., the probability distribution along the interacting distance) will affect the location of both unfavorable and favorable interactions depending on the nature of the system. Moreover, energy gradient maps can be generated based on heat map energy calculations, which facilitates ligand docking as described below.

Extracting Structure from the "Movable Type" Method

The advantage of the MT method is that the energy and the free energy (when introducing the partition function) can be derived using only atomic linkage information coupled with the databases of atom pairwise distance distributions along with their corresponding energies. This offers us a new approach for protein-ligand docking without resorting to exhaustive pose sampling. Our initial efforts utilized the frozen receptor model, but the incorporation of receptor flexibility is, in principle, straightforward and will be explored in the future.

In a docking exercise, the best-docked pose for the ligand is usually obtained based on the highest binding affinity, which can be regarded as an optimization problem. With the frozen binding pocket approximation, generation of the "best" docking pose is a gradient optimization of the ligand atoms within the binding pocket, subject to the constraints of the ligand topology.

Molecular internal linkages including bond lengths and angles only slightly deviate from their optimized values, making them constraints in the ligand energy optimization within the binding pocket. These ligand atom connectivities reduce the dimensionality of the problem in that atomic collections that do not have the correct connectivity are eliminated from further consideration. On the other hand, energies of the torsions and long-range interactions between ligands and proteins vary over comparatively large distance ranges and, thereby, are regarded as the objective functions. Hence, in order to do the optimization it is desirable to obtain the first and second derivatives of the ligand torsion and the protein-ligand long-range interaction partition functions (shown in Equation 43 and 44), which can be readily seen in the gradient maps of the individual atom type pairs.

$$\frac{dc(r)}{dr} = \frac{d(q(r) \cdot z(r))}{dr} = \frac{d(q(r))}{dr} \cdot z(r) + q(r) \cdot \frac{d(z(r))}{dr} = 0 \quad (43)$$

$$\frac{d^2c(r)}{dr^2} = \frac{d^2(q(r) \cdot z(r))}{dr^2} = \frac{d^2(q(r))}{dr^2} \cdot z(r) + 2\left(\frac{d(q(r))}{dr} \cdot \frac{d(z(r))}{dr}\right) + z(r) \cdot \frac{d^2(q(r))}{dr^2} > 0 \quad (44)$$

Optimum ligand atom locations are obtained when the calculation satisfies the minimum values for all the objective functions (ligand torsions and protein-ligand long range interactions) and all ligand bonds and angle constraints.

In the optimization algorithm numerical derivatives of the probability distribution and analytical derivatives for the energy expression via pairwise partial derivatives of the modified Lennard-Jones potentials used in KECSA is obtained. With the ligand topology and first and second derivatives a Newton-Raphson algorithm to optimize the ligand in the pocket is used. A nice feature of this method is that both the lowest free energy binding mode along with all other possible local minima with higher free energies can be identified. Moreover, one can extract saddle-point and higher-order transitions describing the connectivity between the local minima.

Figure 4:
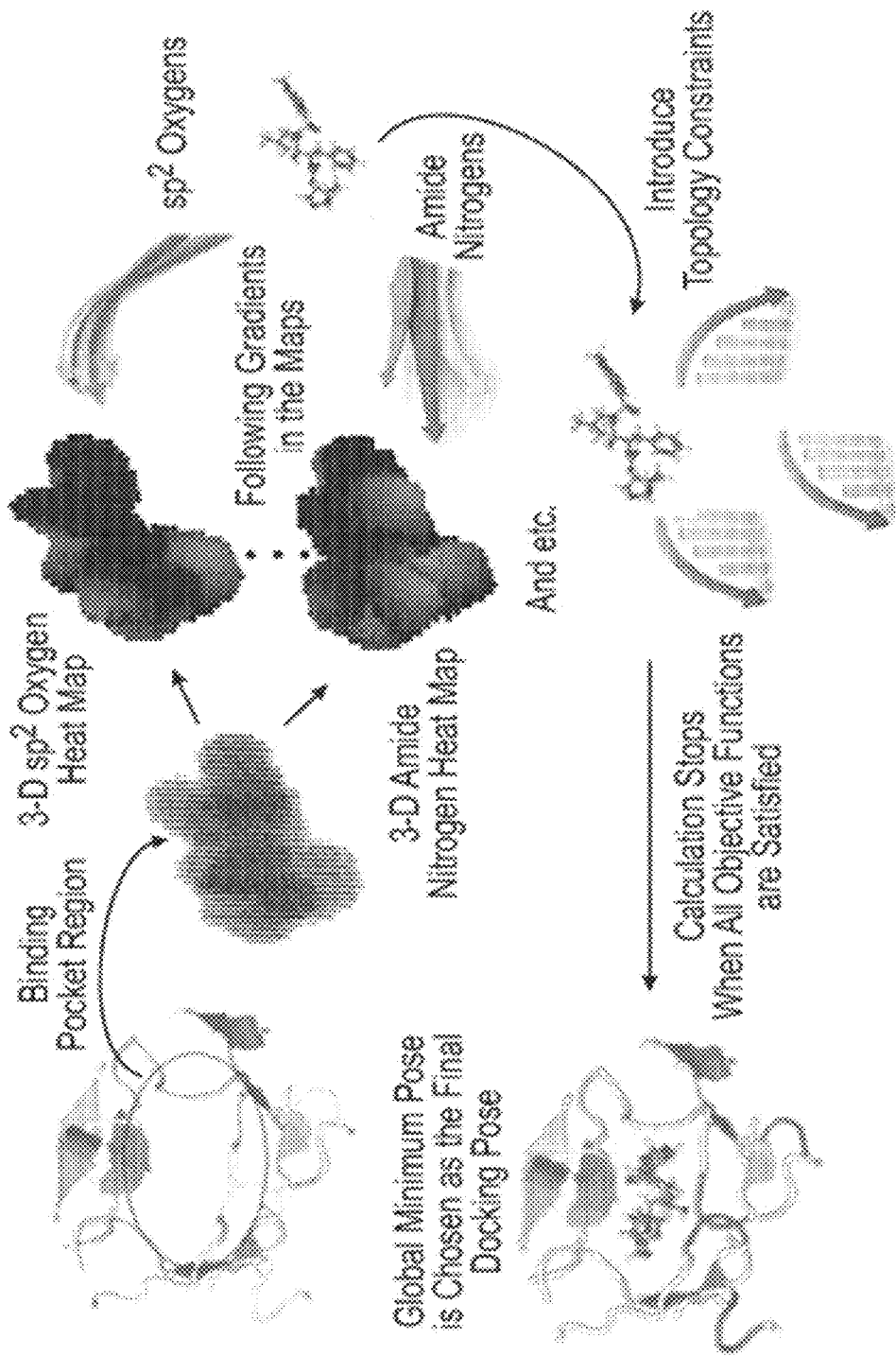
FIG. 4 depicts MT energy maps optimization mechanism to derive the final docking pose in one protein ligand complex, according to some example embodiments.

FIG. 4 introduces the process of the heatmap docking. To illustrate the method in detail one example whose structure is 1LI2 will be discussed. Heatmap docking against the previously introduced test set of 795 protein ligand complexes has also been conducted and this will be summarized below. FIG. 4 depicts MT energy maps optimization mechanism to derive the final docking pose in one protein ligand complex.

The protein-ligand complex with PDB ID 1LI2 is used as an example to illustrate in detail the process of heatmap docking. 1LI2 is a T4 Lysozyme mutant bound to phenol with a modest binding affinity of 4.04 (p$K_d$). The binding pocket region is larger than the small phenol ligand structure (see FIG. 5), potentially allowing several ligand poses that represent local minima. On the other hand, phenol, as the ligand, has a simple enough structure to clearly show the differences in protein-ligand contacts between low energy poses.

Figure 5:
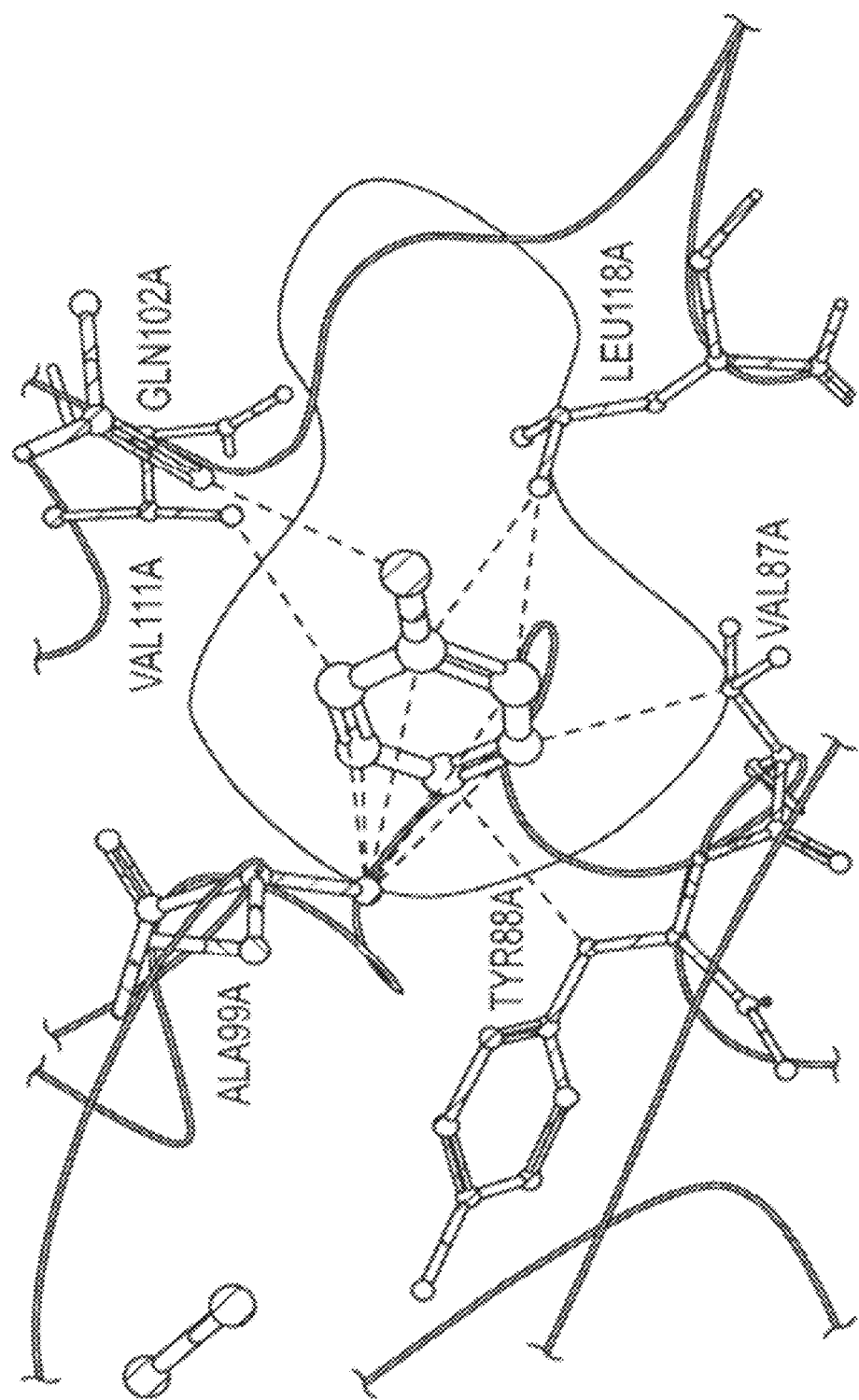
FIG. 5 depicts a contact map of the 1LI2 protein-ligand complex binding region, according to some example embodiments. Hydrophobic contacts are shown as dashed lines and the one hydrogen bond is shown extending between the phenol oxygen atom (central striped atom) and the GLN102A residue as another dashed line. The binding pocket cavity encircled with a solid line.

Judging from the crystal structure, phenol forms a hydrogen bond with GLN102A, and several hydrophobic contacts with VAL87A, TYR88A, ALA99A, VAL111A and LEU118A in the binding pocket (shown in FIG. 5).

FIG. 5 depicts a contact map of the 1LI2 protein-ligand complex binding region. Hydrophobic contacts are shown as dashed lines and the one hydrogen bond is shown between the phenol oxygen atom (central striped atom) and the GLN102A residue as another dashed line. The binding pocket cavity is encircles in a solid line.

There are two atom types ($sp^3$ oxygen and aromatic carbon atoms) in phenol. Based on the MT KECSA calculation, heat maps for both of the atom types within the binding pocket can be generated (FIG. 6).

Figure 6:
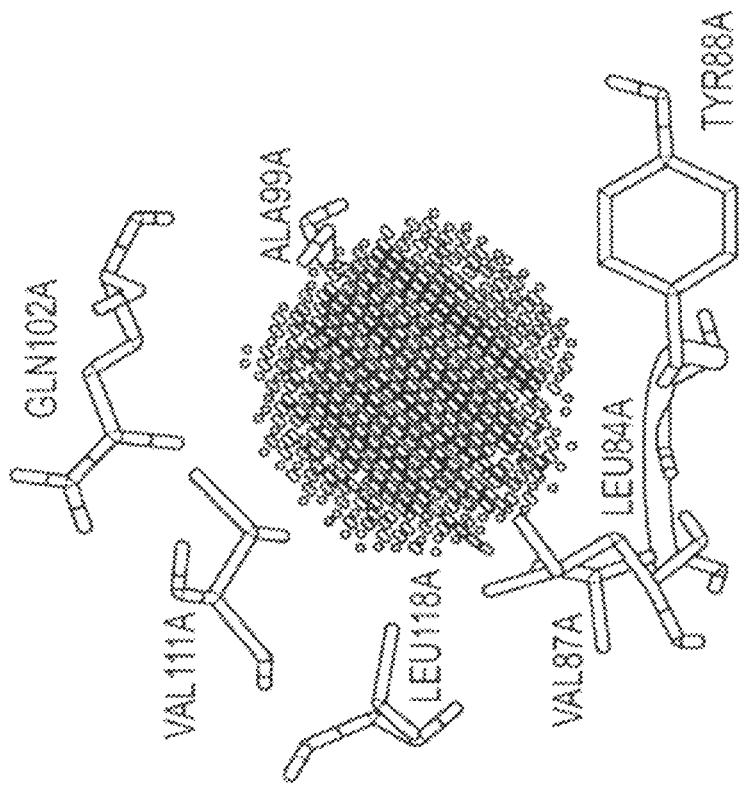
FIG. 6 depicts heat maps for $sp^3$ oxygen (left) and aromatic carbon (right), according to some example embodiments. Grid points with lighter color indicate energetically favorable locations for certain atom types within the binding pocket.
Figure 6:
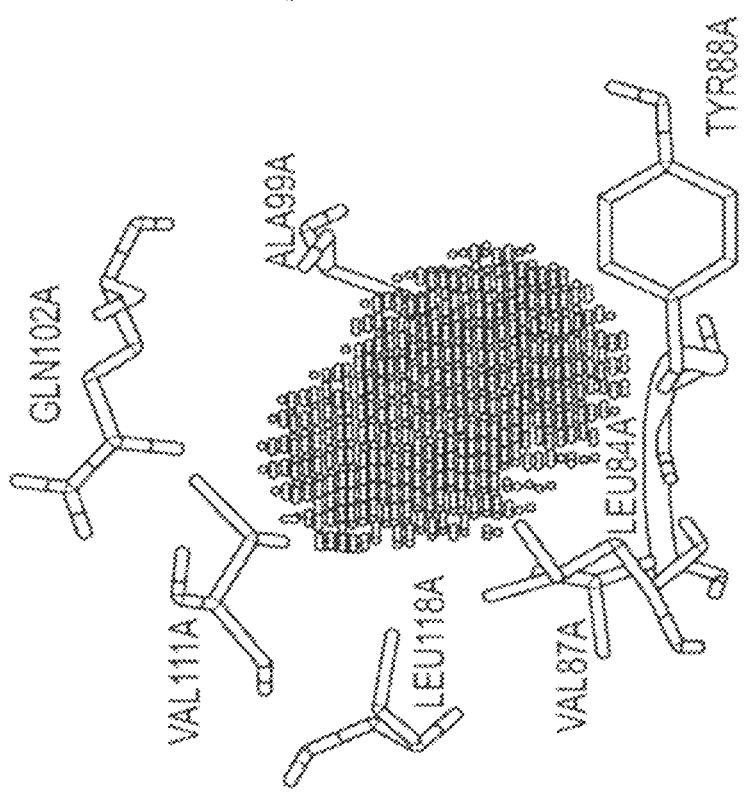

FIG. 6 depicts heat maps for $sp^3$ oxygen (left) and aromatic carbon (right). Grid points with lighter color indicate energetically favorable locations for certain atom types within the binding pocket.

The heatmap docking program then generated one $sp^3$ oxygen and six aromatic carbons to their optimized position following the gradients on their corresponding energy heatmaps while satisfying the linkage constraints of phenol. As a result, together with the energetic global minimum ligand pose (GM), three more local minimum poses (pose a, b and c) were generated using the heatmap docking method. RMSD values (Å) and binding scores ($pK_d$) are shown in Table 2.

TABLE 2

RMSD values (Å) and binding scores ($pK_d$) of the global and local minima

|  | RMSD (Å) | Binding Affinity ($pK_d$) |
| --- | --- | --- |
| Global Minimum | 0.937 | 3.329 |
| Local Minimum a | 2.667 | 2.255 |
| Local Minimum b | 2.839 | 2.975 |
| Local Minimum c | 2.342 | 3.299 |

Figure 7:
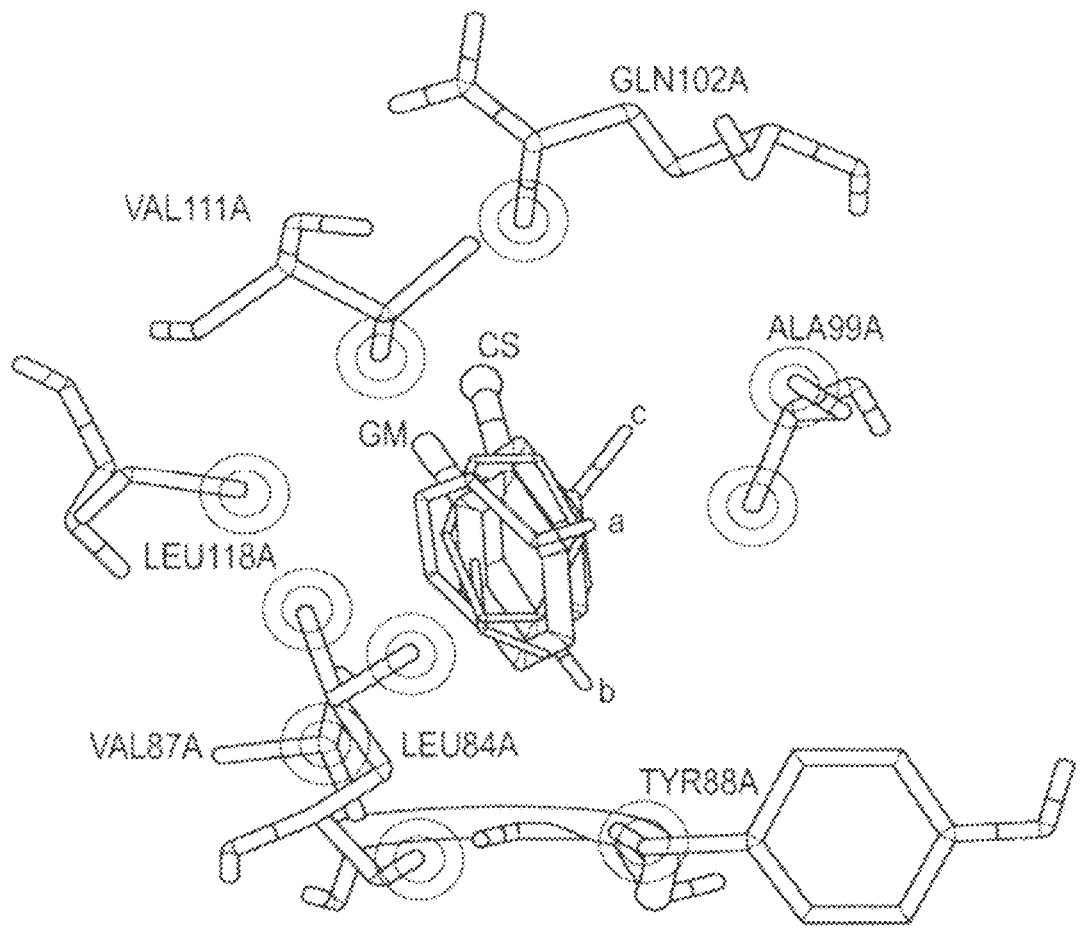
FIG. 7 shows the binding pocket of protein-ligand complex 1L12, ligand crystal structure (marked as CS) is shown as a stick & ball structure, the global minimum pose (marked as GM) is shown as a stick structure along with the three other identified local minimum (marked as a, b, and c), according to some example embodiments. Bubbles (red in the original) on the protein atoms indicate potential contacts with the ligand $sp^3$ oxygen. Other bubbles (grey in the original) on the protein atoms indicate potential contacts with aromatic carbons.

As can be seen in FIG. 7, the GM pose slightly deviates from the crystal structure (CS) because of the adjustment of the hydrogen bond distance between the phenol oxygen and the $sp^2$ oxygen on GLN102A in the MT KECSA calculation. The phenol benzene ring balances the contacts with ALA99A and TYR88A on one side and the contacts with LEU118A, VAL87A and LEU84A on the other. The local minimum pose c and b have close binding scores when compared to the GM pose. They form hydrogen bonds with different hydrogen acceptors (ALA99A backbone oxygen for pose c and LEU84A backbone oxygen for pose b) while maintaining very similar benzene ring locations. The local minimum pose a is trying to form a hydrogen bond with ALA99A backbone oxygen. However, the benzene ring of local minimum pose a is tilted towards the LEU118A, VAL87A and LEU84A side chain carbons, weakening the hydrogen bond with the ALA99A backbone oxygen with the net result being a reduction in binding affinity.

FIG. 7 shows the binding pocket of protein-ligand complex 1LI2, ligand crystal structure (marked as CS) is shown as a stick & ball, the global minimum pose (marked as GM) is shown as a stick along with the three other identified local minimum (marked as a, b, and c). Red bubbles on the protein atoms indicate potential contacts with the ligand $sp^3$ oxygen. Grey bubbles on the protein atoms indicate potential contacts with aromatic carbons.

Using this procedure a docking study was applied to the test set of 795 protein-ligand complexes. The heatmap docking generated an average RMSD of 1.97 Å with 1.27 Å standard deviation compared to the ligand crystal structure. The result for each individual system studied is given in the supplementary information.

The prediction of the free energies associated with a wide range of biological problems remains a very daunting task. Balancing the sampling of the relevant degrees of freedom with accurate energy computation makes this a very difficult problem. The new approach detailed in this disclosure is one that in one-shot samples all the relevant degrees of freedom in a defined region directly affording a free energy without resorting to ad hoc modeling of the entropy associated with a given process. This is accomplished by converting ensemble assembly from a 3-D to a 1-D problem by using pairwise energies of all relevant interactions in a system coupled with their probabilities. This approach is termed the moveable type (MT) method and in conjunction with the Knowledge-based and Empirical Combined Scoring Algorithm (KECSA) potential function the application of this approach to protein ligand pose and binding free energy prediction has been demonstrated. The resultant MT-KECSA model out-performs the original KECSA model showing the power of this approach. Importantly, the present MT model can be applied to any pairwise decomposable potential which will allow us to attack a wide range of problems in biology including the validation of potential functions.

The Movable Type (MT) method numerically simulates the local partition functions utilizing the Monte Carlo integration (MCI) given the initial structures from a canonical ensemble. The MCI method is a widely used numerical approach for free energy calculation. By simulating the integral of the canonical partition function instead of generating enthalpy and entropy values separately, The MCI method allows for the avoidance of expensive and poorly converging entropy calculations.

In one example, the simulation comprises calculation of the following equation:

$$A = -RT\ln[Z_M] = -RT\ln\left[\int_D e^{-\beta E_M(\tau)} d\tau\right] \approx -RT\ln\left[V \frac{\sum_i^N e^{-\beta E_i(r)}}{N}\right] \quad (45)$$

where:
R is the gas constant;
T is temperature, normally 298.15K;
Z is the partition function, which is the sum of the Boltzman factors;
D is a defined volume quantity representing the three dimensional space that particles under study should be contained;
M is a subscription meaning "molecular";
β is a commonly used term representing 1/(RT);
E is the energy;
V is the ensemble volume; and
N is the number of states that have been sampled.

The development of the MT algorithm is inspired by the idea of the MCI approach expressed in equation 45, where the Helmholtz free energy is simulated using the average of the sampled energy states multiplied by the actual sampling volume. The distinctive feature of the MT method is that it numerically simulates the average of the local partition function given a defined sampling volume centered around an initial structure, instead of searching among actual physical structures within that defined volume. In our first MT algorithm publication, a matrix-based random sampling strategy combining every atom pairwise potentials was introduced against each target molecular system, in which all pairwise potentials are regarded as orthogonal and the totally random combinations among atom pairwise distances were performed within a small range of sampling (in one embodiment, ±0.5 Å for every atom pairwise distances). The so-generated hyper-dimensional energy states were associated with pre-modeled structural weighting factors and averaged over their sampling magnitude CN, where C is the defined sampling range (for example, ±0.5 Å) and N is the pairwise contact number. This approach is to simulate the average of the actual physical energy states using the more easily constructible virtual states.

Given an N-particle physical space, a quantitative description of the ensemble volume is written as:

$$V = \int \ldots \int_D d\tau_1 \ldots d\tau_N \quad (46)$$

where $\tau_1$ to $\tau_N$ are the coordinates of all the particles, and D as the domain of definition for all of the particle coordinates.

The ensemble volume is under an exponential growth as the number of dimensions increases. The MT algorithm uses a distance-based coordinate system in order to better estimate the ensemble volume. With all the geometric parameters of the molecules converted into a distance-based representation, the ensemble volume can be expressed using equation 3 which shows the exponential growth of the state volume with the number of energy components.

$$V = 2^{N-4} \times (2\pi)^{N-3} \times (4\pi)^{N-2} C^{N-1} \quad (47)$$

where:

C a constant representing a predetermined boundary of the particle-particle distance in the ensemble, and
N is the number of atoms in the ensemble.

In one embodiment C was selected as 6 Å.

Pseudocode that illustrates the above calculation is set forth in Appendix A.

Figure 19:
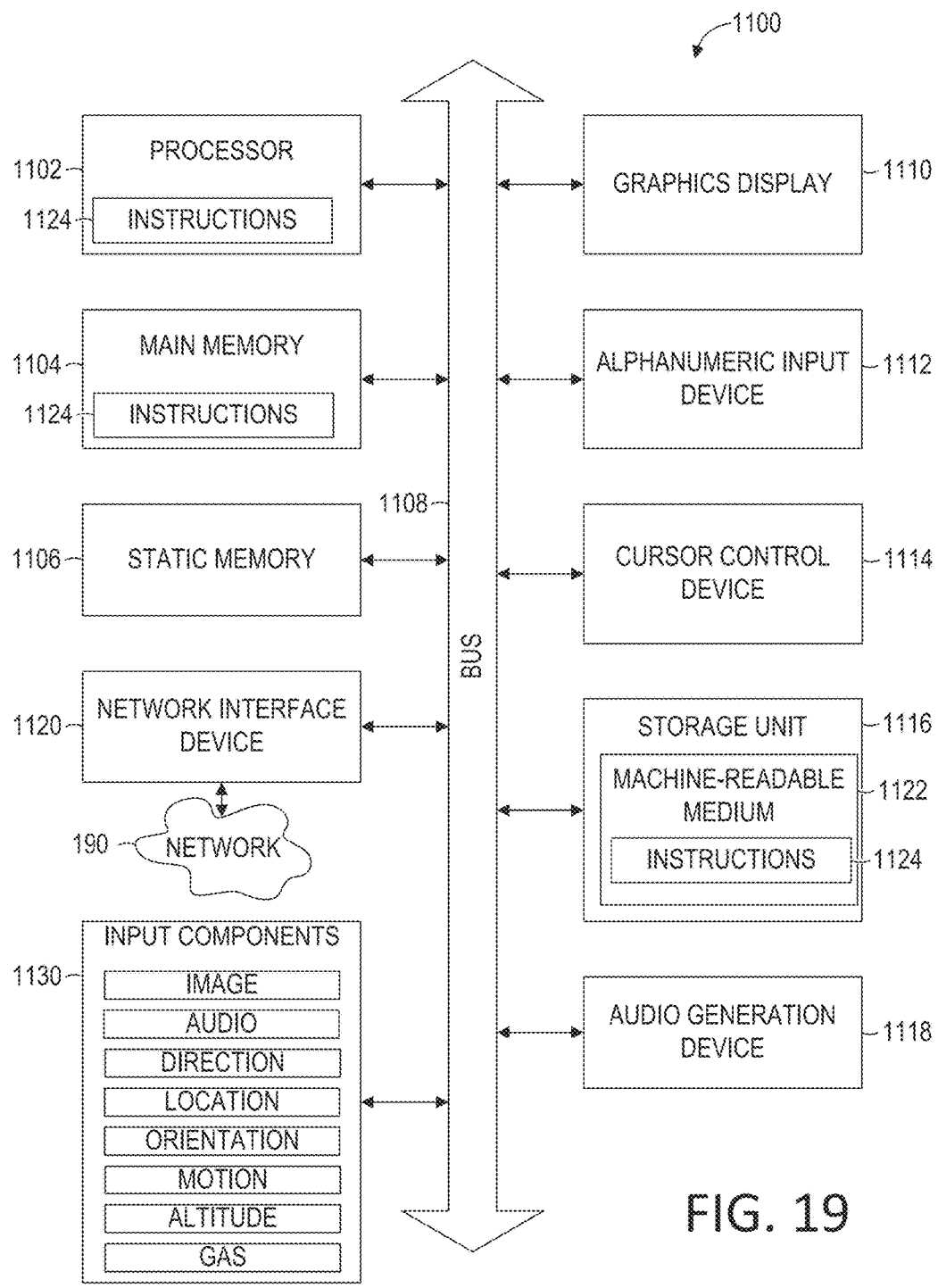
FIG. 19 is a block diagram illustrating components of a machine, according to some example embodiments, able to read instructions from a machine-readable medium and perform any one or more of the methodologies discussed herein.

FIG. 19 is a block diagram illustrating components of a machine, according to some example embodiments, able to read instructions from a machine-readable medium and perform any one or more of the methodologies discussed herein.

Any of the machines, databases, or devices shown or discussed herein may be implemented in a general-purpose computer modified (e.g., configured or programmed) by software (e.g., one or more software modules) to be a special-purpose computer to perform one or more of the functions described herein for that machine, database, or device. For example, a computer system able to implement any one or more of the methodologies described herein is discussed below with respect to FIG. 19. As used herein, a "database" is a data storage resource and may store data structured as a text file, a table, a spreadsheet, a relational database (e.g., an object-relational database), a triple store, a hierarchical data store, or any suitable combination thereof. Moreover, any two or more of the machines, databases, or devices illustrated in FIG. 19 may be combined into a single machine, and the functions described herein for any single machine, database, or device may be subdivided among multiple machines, databases, or devices.

FIG. 19 is a block diagram illustrating components of a machine 1100, according to some example embodiments, able to read instructions 1124 from a machine-readable medium 1122 (e.g., a non-transitory machine-readable medium, a machine-readable storage medium, a computer-readable storage medium, or any suitable combination thereof) and perform any one or more of the methodologies discussed herein, in whole or in part. Specifically, FIG. 19 shows the machine 1100 in the example form of a computer system (e.g., a computer) within which the instructions 1124 (e.g., software, a program, an application, an applet, an app, or other executable code) for causing the machine 1100 to perform any one or more of the methodologies discussed herein may be executed, in whole or in part.

In alternative embodiments, the machine 1100 operates as a standalone device or may be connected (e.g., networked) to other machines. In a networked deployment, the machine 1100 may operate in the capacity of a server machine or a client machine in a server-client network environment, or as a peer machine in a distributed (e.g., peer-to-peer) network environment. The machine 1100 may be a server computer, a client computer, a personal computer (PC), a tablet computer, a laptop computer, a netbook, a cellular telephone, a smartphone, a set-top box (STB), a personal digital assistant (PDA), a web appliance, a network router, a network switch, a network bridge, or any machine capable of executing the instructions 1124, sequentially or otherwise, that specify actions to be taken by that machine. Further, while only a single machine is illustrated, the term "machine" shall also be taken to include any collection of machines that individually or jointly execute the instructions 1124 to perform all or part of any one or more of the methodologies discussed herein.

The machine 1100 includes a processor 1102 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 1104, and a static memory 1106, which are configured to communicate with each other via a bus 1108. The processor 1102 may contain microcircuits that are configurable, temporarily or permanently, by some or all of the instructions 1124 such that the processor 1102 is configurable to perform any one or more of the methodologies described herein, in whole or in part. For example, a set of one or more microcircuits of the processor 1102 may be configurable to execute one or more modules (e.g., software modules) described herein.

The machine 1100 may further include a graphics display 1110 (e.g., a plasma display panel (PDP), a light emitting diode (LED) display, a liquid crystal display (LCD), a projector, a cathode ray tube (CRT), or any other display capable of displaying graphics or video). The machine 1100 may also include an alphanumeric input device 1112 (e.g., a keyboard or keypad), a cursor control device 1114 (e.g., a mouse, a touchpad, a trackball, a joystick, a motion sensor, an eye tracking device, or other pointing instrument), a storage unit 1116, an audio generation device 1118 (e.g., a sound card, an amplifier, a speaker, a headphone jack, or any suitable combination thereof), and a network interface device 1120.

The storage unit 1116 includes the machine-readable medium 1122 (e.g., a tangible and non-transitory machine-readable storage medium) on which are stored the instructions 1124 embodying any one or more of the methodologies or functions described herein. The instructions 1124 may also reside, completely or at least partially, within the main memory 1104, within the processor 1102 (e.g., within the processor's cache memory), or both, before or during execution thereof by the machine 1100. Accordingly, the main memory 1104 and the processor 1102 may be considered machine-readable media (e.g., tangible and non-transitory machine-readable media). The instructions 1124 may be transmitted or received over the network 190 via the network interface device 1120. For example, the network interface device 1120 may communicate the instructions 1124 using any one or more transfer protocols (e.g., hypertext transfer protocol (HTTP)).

The network 190 may be any network that enables communication between or among machines, databases, and devices (e.g., the server machine 110 and the device 130). Accordingly, the network 190 may be a wired network, a wireless network (e.g., a mobile or cellular network), or any suitable combination thereof. The network 190 may include one or more portions that constitute a private network, a public network (e.g., the Internet), or any suitable combination thereof. Accordingly, the network 190 may include one or more portions that incorporate a local area network (LAN), a wide area network (WAN), the Internet, a mobile telephone network (e.g., a cellular network), a wired telephone network (e.g., a plain old telephone system (POTS) network), a wireless data network (e.g., WiFi network or WiMax network), or any suitable combination thereof. Any one or more portions of the network 190 may communicate information via a transmission medium. As used herein, "transmission medium" refers to any intangible (e.g., transitory) medium that is capable of communicating (e.g., transmitting) instructions for execution by a machine (e.g., by one or more processors of such a machine), and includes digital or analog communication signals or other intangible media to facilitate communication of such software.

In some example embodiments, the machine 1100 may be a portable computing device, such as a smart phone or tablet computer, and have one or more additional input components 1130 (e.g., sensors or gauges). Examples of such input components 1130 include an image input component (e.g., one or more cameras), an audio input component (e.g., a microphone), a direction input component (e.g., a compass), a location input component (e.g., a global positioning system (GPS) receiver), an orientation component (e.g., a gyroscope), a motion detection component (e.g., one or more accelerometers), an altitude detection component (e.g., an altimeter), and a gas detection component (e.g., a gas sensor). Inputs harvested by any one or more of these input components may be accessible and available for use by any of the modules described herein.

As used herein, the term "memory" refers to a machine-readable medium able to store data temporarily or permanently and may be taken to include, but not be limited to, random-access memory (RAM), read-only memory (ROM), buffer memory, flash memory, and cache memory. While the machine-readable medium 1122 is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing the instructions 1124 for execution by the machine 1100, such that the instructions 1124, when executed by one or more processors of the machine 1100 (e.g., processor 1102), cause the machine 1100 to perform any one or more of the methodologies described herein, in whole or in part. Accordingly, a "machine-readable medium" refers to a single storage apparatus or device, as well as cloud-based storage systems or storage networks that include multiple storage apparatus or devices. The term "machine-readable medium" shall accordingly be taken to include, but not be limited to, one or more tangible (e.g., non-transitory) data repositories in the form of a solid-state memory, an optical medium, a magnetic medium, or any suitable combination thereof.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute software modules (e.g., code stored or otherwise embodied on a machine-readable medium or in a transmission medium), hardware modules, or any suitable combination thereof. A "hardware module" is a tangible (e.g., non-transitory) unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, and such a tangible entity may be physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software (e.g., a software module) may accordingly configure one or more processors, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules. As used herein, "processor-implemented module" refers to a hardware module in which the hardware includes one or more processors. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an application program interface (API)).

The performance of certain operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

The method described herein is depicted without limitation in the following examples.

Example No. 1

Here we describe a very simple methane-butane two-body system as an example that illustrates, in detail, the binding free energy calculation using the "movable type" (MT) method with the KECSA energy function. The binding of two-molecules in solution can be written as:

$$\Delta G_b^s = \Delta G_b^g + \Delta G_{solv}^{1-2} - \Delta G_{solv}^1 - \Delta G_{solv}^2 \tag{1i}$$

where methane and butane are indicated as molecule 1 and 2, respectively.

Using $\Delta\Delta G_{solv} = \Delta G_{solv}^{1-2} - \Delta G_{solv}^1 - \Delta G_{solv}^2$, Equation 1i simplifies to:

$$\Delta G_b^s = \Delta G_b^g - \Delta\Delta G_{solv} \tag{2i}$$

The canonical ensemble is used in computing Helmholtz free energies in Equation 2i. Because both methane and butane have no polar atoms, and their accessible surface areas have a negligible change after association, we can ignore computing $\Delta\Delta G_{solv}$ further simplifying this example. For the gas-phase binding free energy calculation, which is the core of the problem, the binding free energy is given as a ratio of partition functions:

$$\Delta G_b^g \approx \Delta A_b^g = -RT\ln\left[\frac{Z_{1-2}}{Z_2 Z_1}\right] = -RT\ln\left[\frac{\int e^{-\beta E_{1-2}(r)} dr}{\int e^{-\beta E_2(r)} dr \int e^{-\beta E_1(r)} dr}\right] = \tag{3i}$$

-continued $$-RT\ln\left[\frac{F_{1-2}\langle e^{-\beta E_{1-2}(r)}\rangle}{F_2\langle e^{-\beta E_2(r)}\rangle F_1\langle e^{-\beta E_1(r)}\rangle}\right]$$

As is shown in Equations 5 and 6 in the article, the degrees of freedom (DoFs) for protein-ligand systems can be approximated as:

$$\frac{F_{PL}}{F_P F_L} = \frac{F_{boundP}^{external} F_{boundL}^{external} F_{boundP}^{internal} F_{boundL}^{internal}}{F_{freeP}^{extended} F_{freeP}^{internal} \times F_{freeL}^{extended} F_{freeL}^{internal}} = \quad (4i)$$

$$\frac{F_{boundL}^{extended}}{F_{freeL}^{extended}} = \frac{a\pi^2 V_{pocket}}{8\pi^2 C} = \frac{aV_{pocket}}{8C}$$

For small-molecule systems, like the methane-butane case in our current example, if butane is treated as the "receptor" and methane as the "ligand", then $V_{pocket}$ (translational DoF for the bound ligands) is approximately equal to C (translational DoF of the free ligand), because the smaller the "receptor" is, the weaker the constraints on the "ligand". A small "receptor" like butane, when compared to any protein molecule, has a greatly reduced constraint on the translational movement of a "ligand" like methane, making $V_{pocket} \approx C$. Moreover, for the rotational DoF, the volume factor "a" is also approximately equal to 8, for small molecules because the small receptor affords more accessible volume than found in protein-ligand systems. Hence for two-body small molecule systems:

$$\frac{F_{1-2}}{F_2 F_1} \approx 1 \quad (5i)$$

yielding $$\Delta G_b^g \approx -RT\ln\left[\frac{\langle e^{-\beta E_{1-2}(r)}\rangle}{\langle e^{-\beta E_2(r)}\rangle\langle e^{-\beta E_1(r)}\rangle}\right] \quad (6i)$$

Using the MT method, molecular energies are decomposed into atom pair interaction energies, including bond, angle, torsion and long-range interactions sampled along atom pairwise distances multiplied by the corresponding probabilities, as shown in Equation 7i:

$$\langle e^{-\beta E}\rangle = \sum_i \prod_j Q_{ij} e^{-\beta E_{ij}} \quad (7i)$$

On the left hand side of Equation 7i, E is the microstate energy within an ensemble average, and on the right hand side each "j" indicates each atom pair in the molecule.

In the KECSA implementation of the MT method, only heavy atoms are utilized in the calculation, making methane molecule one of the simplest cases:

$$E_{methane} = E_{sp^3 Carbon} \quad (8i)$$

$$\left\langle e^{E_{methane}}\right\rangle = e^{E_{sp^3 Carbon}} \quad (9i)$$

The atom pairwise energy is zero in methane, making the energy of methane equal to the energy of a single $sp^3$ carbon atom. In the MT method, it is not desirable to carry out a single atom energy calculation, because they cancel out when using Equation 6i for the free energy calculation.

Butane has four $sp^3$ carbon atoms in a chain, making three $sp^3$ carbon-$sp^3$ carbon bonds, two $sp^3$ carbon-$sp^3$ carbon angles, and one $sp^3$ carbon-$sp^3$ carbon torsion. Sampling along the distance for all interactions and gathering all possible combinations generates all the desirable energy terms in Equation 10i.

$$\langle e^{E_{butane}}\rangle = \quad (10i)$$

$$\sum_\alpha^{Bond\ Distance\ Range} \prod_a^3 Q_{a\alpha} e^{-\beta E_{a\alpha}} \times \sum_\beta^{Angle\ Distance\ Range} \prod_b^2 Q_{b\beta}$$

$$e^{-\beta E_{b\beta}} \times \sum_\gamma^{Torsion\ Distance\ Range} \prod_c^1 Q_{c\gamma} e^{-\beta E_{c\gamma}}$$

Using bond energy terms as an example (as used in the article) each of the three $sp^3$ carbon-$sp^3$ carbon bond partition functions can be modeled as $$\mathbf{z}_k^{bond} = \begin{bmatrix} z_k^{bond}(r_1) \\ z_k^{bond}(r_2) \\ \vdots \\ z_k^{bond}(r_a) \\ \vdots \\ z_k^{bond}(r_n) \end{bmatrix} = \begin{bmatrix} e^{-\beta E_k^{bond}(r_1)} \\ e^{-\beta E_k^{bond}(r_2)} \\ \vdots \\ e^{-\beta E_k^{bond}(r_a)} \\ \vdots \\ e^{-\beta E_k^{bond}(r_n)} \end{bmatrix} \quad (11i)$$

k indicates each $sp^3$ carbon-$sp^3$ carbon bond and 1 through n are the distance increments. Each increment is set to 0.005 Å. The bond energy is modeled as a harmonic oscillator:

$$z_k^{bond}(r_a) = e^{-79.98(r_a - 1.53)^2 + 4.195} \quad (12i)$$

Figure 8:
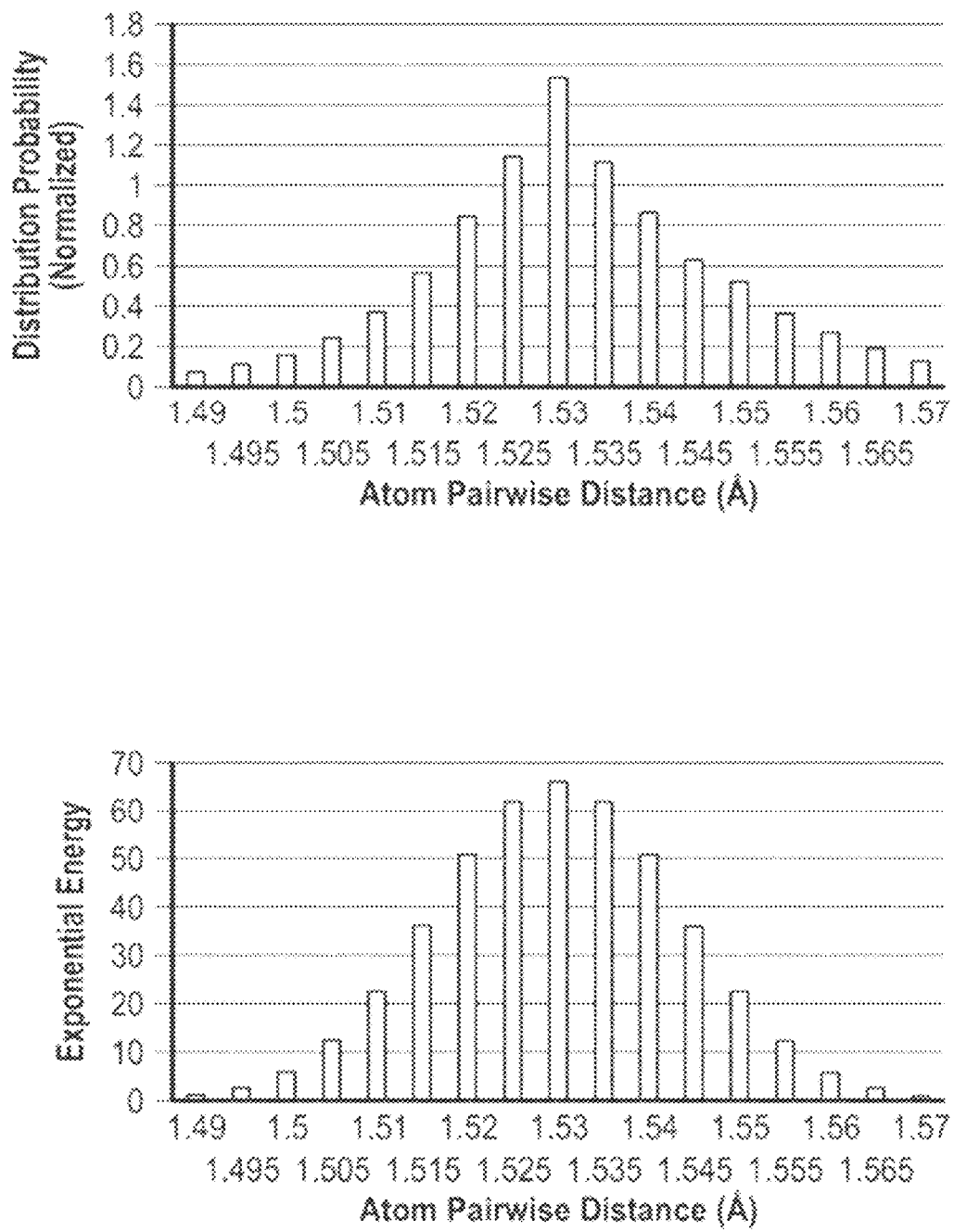
FIG. 8 shows sp3 carbon-sp3 carbon bond probability distribution (top) and exponential energy vs. atom pairwise distance (bottom), according to some example embodiments.
Figure 9:
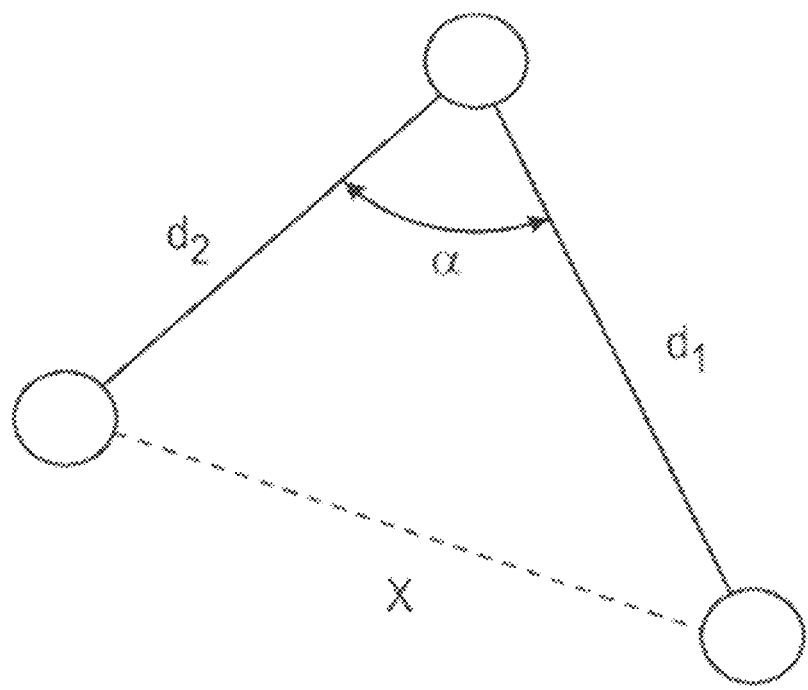
FIG. 9 shows a representation of the torsion angle a using the pairwise distance x, according to some example embodiments.
Figure 10:
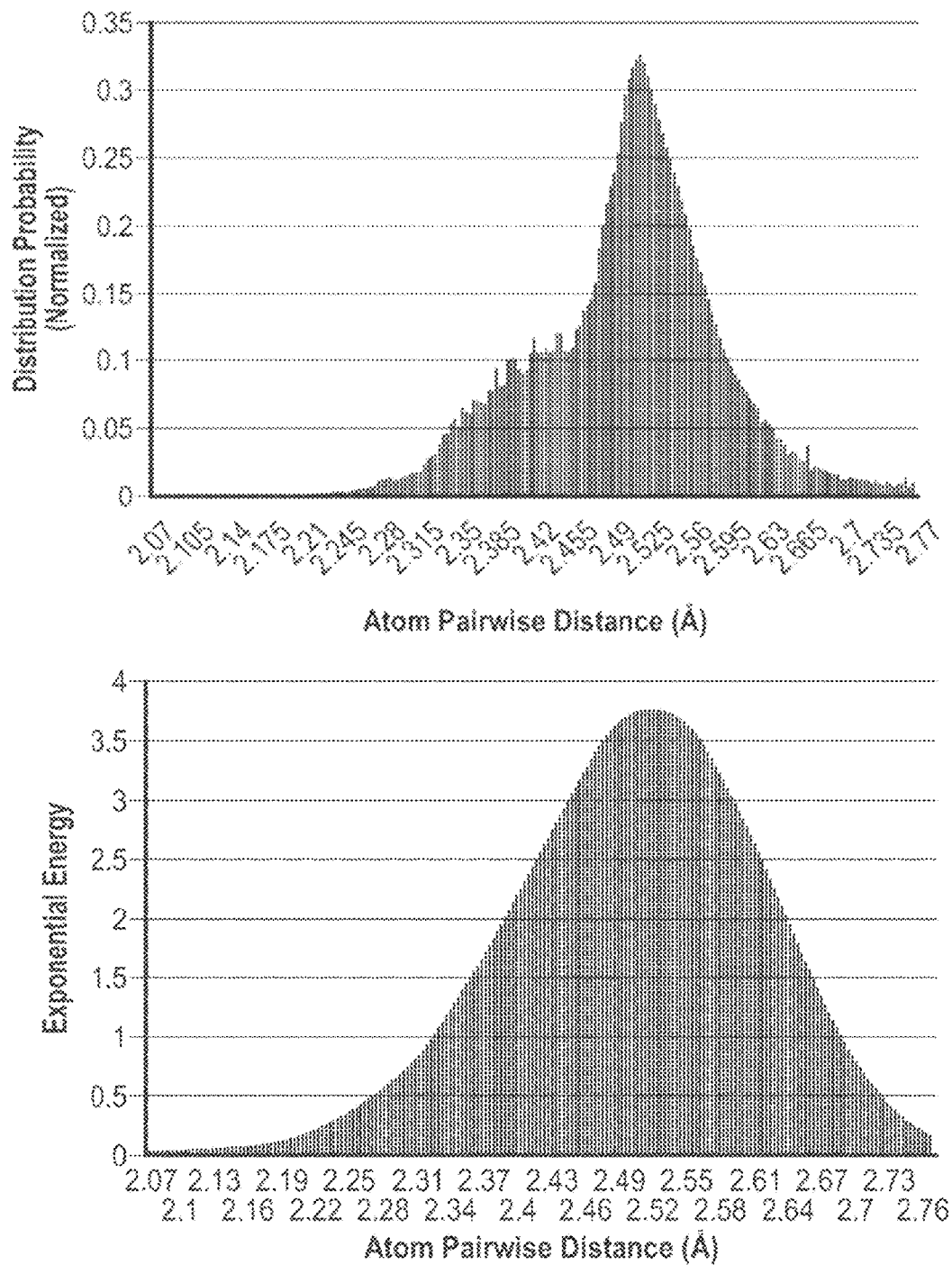
FIG. 10 shows $sp^3$ carbon-($sp^3$ carbon)-$sp^3$ carbon angle probability distribution (top) and the exponential energy vs. atom pairwise distance (bottom), according to some example embodiments.

−79.98 is the energy unit used in KECSA and will be ultimately converted into kcal/mol. 1.53 Å is the distance at which the $sp^3$ carbon-$sp^3$ carbon bond energy reaches its minimum and 4.195 is a constant that adjusts the energy baseline to zero. The FIG. 8 shows $sp^3$ carbon-$sp^3$ carbon bond probability distribution and exponential energy vs. atom pairwise distance.

Sampling of bond energies includes all distances that derive non-zero partition function values, which range from 1.72 Å to 1.99 Å in the $sp^3$ carbon-$sp^3$ carbon bond interaction case. The product over all three bond-linked $sp^3$ carbon-$sp^3$ carbon pairs derives the total bond partition function in butane (Equation 13i).

$$Z_{butane}^{bond} = \mathcal{Z}_1^{bond} \otimes \mathcal{Z}_2^{bond} \otimes \qquad (13i)$$

$$\mathcal{Z}_3^{bond} = \begin{bmatrix} e^{-\beta E_1^{bond}(r_1)} \\ \vdots \\ e^{-\beta E_1^{bond}(r_a)} \\ \vdots \\ e^{-\beta E_1^{bond}(r_n)} \end{bmatrix} \begin{bmatrix} e^{-\beta E_2^{bond}(r_1)} & \cdots & e^{-\beta E_2^{bond}(r_a)} & \cdots & e^{-\beta E_2^{bond}(r_n)} \end{bmatrix} \begin{bmatrix} e^{-\beta E_3^{bond}(r_1)} & \cdots & e^{-\beta E_3^{bond}(r_a)} & \cdots & e^{-\beta E_3^{bond}(r_n)} \end{bmatrix} =$$

$$\begin{bmatrix} e^{-\beta E_1^{bond}(r_1)}e^{-\beta E_2^{bond}(r_1)}e^{-\beta E_3^{bond}(r_1)} & e^{-\beta E_1^{bond}(r_1)}e^{-\beta E_2^{bond}(r_1)}e^{-\beta E_3^{bond}(r_2)} & \cdots & e^{-\beta E_1^{bond}(r_1)}e^{-\beta E_2^{bond}(r_n)}e^{-\beta E_3^{bond}(r_n)} \\ e^{-\beta E_1^{bond}(r_2)}e^{-\beta E_2^{bond}(r_1)}e^{-\beta E_3^{bond}(r_1)} & e^{-\beta E_1^{bond}(r_2)}e^{-\beta E_2^{bond}(r_1)}e^{-\beta E_3^{bond}(r_2)} & \cdots & e^{-\beta E_1^{bond}(r_2)}e^{-\beta E_2^{bond}(r_n)}e^{-\beta E_3^{bond}(r_n)} \\ \vdots & \vdots & \ddots & \vdots \\ e^{-\beta E_1^{bond}(r_n)}e^{-\beta E_2^{bond}(r_1)}e^{-\beta E_3^{bond}(r_1)} & e^{-\beta E_1^{bond}(r_n)}e^{-\beta E_2^{bond}(r_1)}e^{-\beta E_3^{bond}(r_2)} & \cdots & e^{-\beta E_1^{bond}(r_n)}e^{-\beta E_2^{bond}(r_n)}e^{-\beta E_3^{bond}(r_n)} \end{bmatrix}$$

$r_1$ through $r_n$ in Equation 13i indicates the $sp^3$ carbon-$sp^3$ carbon bond distance range from 1.72 Å to 1.99 Å

The angle and torsion partition functions can be built in a similar fashion:

$$Z_{butane}^{angle} = \mathcal{Z}_1^{angle} \otimes \mathcal{Z}_2^{angle} \qquad (14i)$$

$$= \begin{bmatrix} e^{-\beta E_1^{angle}(r_1)} \\ \vdots \\ e^{-\beta E_1^{angle}(r_a)} \\ \vdots \\ e^{-\beta E_1^{angle}(r_n)} \end{bmatrix} \begin{bmatrix} e^{-\beta E_2^{angle}(r_1)} & \cdots & e^{-\beta E_2^{angle}(r_a)} & \cdots & e^{-\beta E_1^{angle}(r_n)} \end{bmatrix}$$

$$= \begin{bmatrix} e^{-\beta E_1^{angle}(r_1)}e^{-\beta E_2^{angle}(r_1)} & e^{-\beta E_1^{angle}(r_1)}e^{-\beta E_2^{angle}(r_2)} & \cdots & e^{-\beta E_1^{angle}(r_1)}e^{-\beta E_2^{angle}(r_n)} \\ e^{-\beta E_1^{angle}(r_2)}e^{-\beta E_2^{angle}(r_1)} & e^{-\beta E_1^{angle}(r_2)}e^{-\beta E_2^{angle}(r_2)} & \cdots & e^{-\beta E_1^{angle}(r_2)}e^{-\beta E_2^{angle}(r_n)} \\ \vdots & \vdots & \ddots & \vdots \\ e^{-\beta E_1^{angle}(r_n)}e^{-\beta E_2^{angle}(r_1)} & e^{-\beta E_1^{angle}(r_n)}e^{-\beta E_2^{angle}(r_2)} & \cdots & e^{-\beta E_1^{angle}(r_n)}e^{-\beta E_2^{angle}(r_n)} \end{bmatrix}$$

$$Z_{butane}^{torsion} = \mathcal{Z}_1^{torsion} \qquad (15i)$$

$$= \begin{bmatrix} e^{-\beta E_1^{torsion}(r_1)} \\ \vdots \\ e^{-\beta E_1^{torsion}(r_a)} \\ \vdots \\ e^{-\beta E_1^{torsion}(r_n)} \end{bmatrix}$$

In the model, bonds, angles, torsions and long-range interactions are all formulated using the atom pairwise distance, because (1) the units of the variables all agree with each other in the matrix calculation and (2) databases with the lowest dimension, i.e. one dimension for an atom pairwise distance based database, is much easier to manipulate than databases with unmatched dimensions, e.g. an angle-based database contains two dimensions with three atoms, and the torsion-based database has three dimensions with four atoms. To avoid this all angles and torsions are all represented by atom pairwise distances, which is described below.

Angles are converted into distances using the law of cosines. In FIG. 2, the angle $\alpha$ can be described using the distance x together with $d_1$ and $d_2$ using Equation 16i:

$$\alpha = \arccos\left(\frac{d_1^2 + d_2^2 - x^2}{2d_1 d_2}\right) \qquad (16i)$$

and the angle energy terms are formulated as:

$$E^{angle}(\alpha) = \varepsilon(\alpha - \theta_0)^2 = E^{angle}(r) = \varepsilon\left(\arccos\left(\frac{d_1^2 + d_2^2 - x^2}{2d_1 d_2}\right) - \theta_0\right)^2 \qquad (17i)$$

Depending on the center atoms that connect the two atoms having an angle interaction, different parameters are assigned to $\varepsilon$, $d_1$, $d_2$ and $\theta_0$. In butane, the $sp^3$ carbon-($sp^3$ carbon)-$sp^3$ carbon angle partition function is modeled as:

$$e^{E^{angle}(r)} = e^{-29.90\left(arccos\left(\frac{4.68-x^2}{4.68}\right)-1.935\right)^2 - 1.327} \quad (18i)$$

Figure 11:
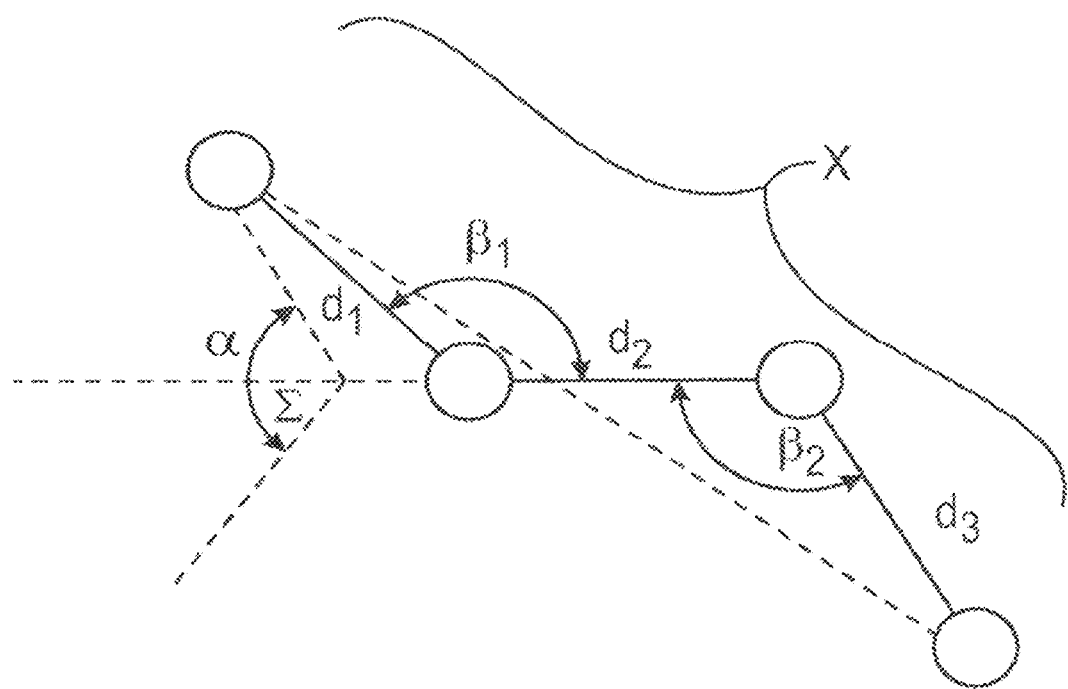
FIG. 11 depicts the torsion angle a with the atom pairwise distance x, according to some example embodiments.

As shown in FIG. 11, the torsion angle α is modeled using an atom pairwise distance x with the help of bond lengths $d_1$ $d_2$ $d_3$ and angles $\beta_1$ and $\beta_2$.

$$\alpha = arccos\left(\frac{d_1^2 \cdot \sin^2(\pi-\beta_1) + d_3^2\cos^2(\pi-\beta_2) + (d_3\cos(\pi-\beta_2)+d_2+d_1\cos(\pi-\beta_1))^2 - x^2}{2d_1\sin(\pi-\beta_1)\sqrt{d_3^2 - d_3^2\cos^2(\pi-\beta_2)}}\right) \quad (19i)$$

and the torsion partition function is modeled as:

$$e^{E^{Torsion}(\alpha)} = \varepsilon_1(1+\sin(p_1\alpha)) + \varepsilon_2(1+\sin(p_2\alpha)) \quad (20i)$$

When used in the $sp^3$ carbon-($sp^3$ carbon- $sp^3$ carbon)-$sp^3$ carbon torsion case, the parameters are given in Equation 21i:
and the torsion partition function is modeled as:

$$e^{E^{Torsion}(\alpha)} = e^{-0.0841(1+\sin(6.07\alpha))+0.0945(1+\sin(-4.61\alpha))} \quad (21i)$$

Figure 12:
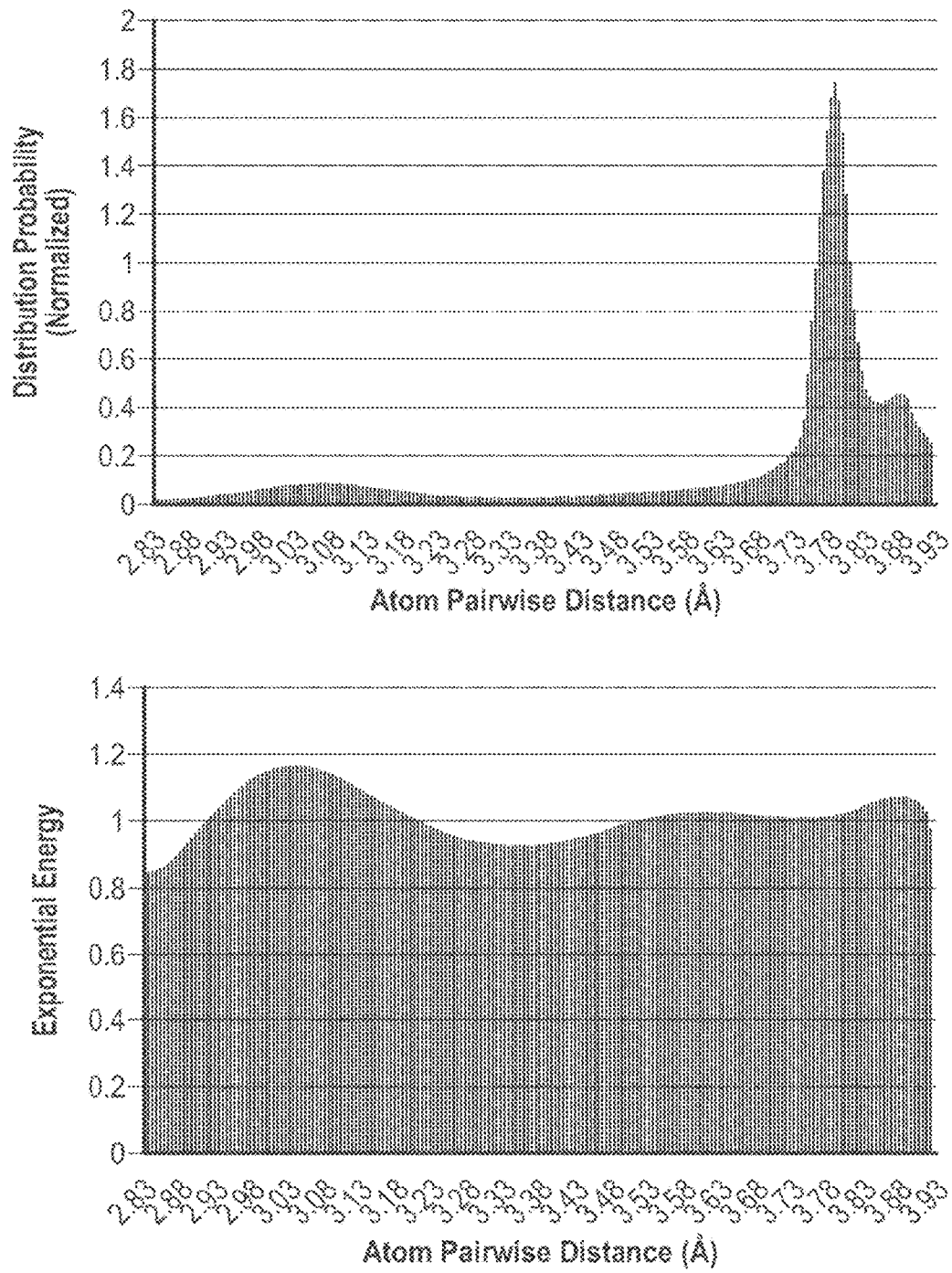
FIG. 12 shows sp3 carbon-(sp3 carbon- sp3 carbon)-sp3 carbon torsion probability distribution (top) and exponential energy vs. atom pairwise distance (bottom), according to some example embodiments.

The probability distribution and exponential energy vs. atom pairwise distance for the $sp^3$ carbon-($sp^3$ carbon- $sp^3$ carbon)-$sp^3$ carbon torsion are shown in FIG. 12.

Hence, the partition functions representing 3 bonds, 2 angles and 1 torsion can be calculated using Equation 13i through 15i.

$$Z_{butane} = Z_{butane}^{bond} \otimes Z_{butane}^{angle} \otimes Z_{butane}^{torsion} \quad (22i)$$

Probability matrixes are modeled similarly using:

$$Q_{butane} = Q_{butane}^{bond} \otimes Q_{butane}^{angle} \otimes Q_{butane}^{torsion} \otimes Q_{butane}^{long-range} \quad (23i)$$

with probability values gathered from available structural data. The ensemble averaged partition function of butane can then be derived with Equation 24i, including all interaction matrices defined by $\square_{butane} \cdot \square_{butane}$ together with four $sp^3$ carbon single atom energies.

$$\langle e^{E_{butane}} \rangle = Q_{butane} \cdot Z_{butane} \cdot e^{4E_{sp3Carbon}} \quad (24i)$$

The methane-butane complex partition function is, thereby, modeled as:

$$C_{1-2} = Q_{1-2} \cdot Z_{1-2} \cdot e^{E_{sp3Carbon}} \cdot e^{4E_{sp3Carbon}} \quad (25i)$$

Methane has only one $sp^3$ carbon single atom energy partition function and no interaction matrix, while butane has four $sp^3$ carbon single atom energy partition functions, probability matrix $Q_{butane}$ and an atom pairwise interaction partition function matrix $Z_{butane}$. The complex probability matrix $Q_{1-2}$ and atom pairwise interaction partition function matrix $Z_{1-2}$ are modeled as:

$$Z_{1-2} = Z_{butane}^{bond} \otimes Z_{butane}^{angle} \otimes Z_{butane}^{torsion} \otimes Z_{1-2}^{long-range} \quad (26i)$$

$$Q_{1-2} = Q_{butane}^{bond} \otimes Q_{butane}^{angle} \otimes Q_{butane}^{torsion} \otimes Q_{butane}^{long-range} \otimes Q_{1-2}^{long-range} \quad (27i)$$

Long-range interactions are separated into van der Waals-electrostatic terms and hydrogen bond terms, the details of how they are modeled and their parameterization are given in the relevant literature.[1]

(28i)

(29i)

With the desirable components assembled, the gas-phase binding free energy can be derived using Equation 30i.

$$\Delta G_b^g = -RT \ln\left[\frac{\langle e^{-\beta E_{1-2}(r)} \rangle}{\langle e^{-\beta E_{butane}(r)} \rangle \langle e^{-\beta E_{methane}(r)} \rangle}\right] \quad (30i)$$

$$= -RT \ln\left[\frac{Q_{1-2} \cdot Z_{1-2} \cdot e^{E_{sp3Carbon}} \cdot e^{4E_{sp3Carbon}}}{Q_{butane} \cdot Z_{butane} \cdot e^{4E_{sp3Carbon}} \cdot e^{E_{sp3Carbon}}}\right]$$

$$= -RT \ln\left[\frac{Q_{1-2} \cdot Z_{1-2} \cdot e^{E_{sp3Carbon}} \cdot e^{4E_{sp3Carbon}}}{Q_{butane} \cdot Z_{butane} \cdot e^{4E_{sp3Carbon}} \cdot e^{E_{sp3Carbon}}}\right]$$

$$= -RT \ln\left[\frac{Q_{1-2} \cdot Z_{1-2}}{Q_{butane} \cdot Z_{butane}}\right]$$

Example No. 2

Different approximate algorithms have been explored for the Movable Type (MT) matrix multiplication approach presented in the manuscript. In order for the algorithm to have good accuracy and computational performance it needs: (1) much smaller sub-matrices for computational convenience, (2) avoid creation of large matrices during MT computation, (3) inclusion of as many as possible of the significant Boltzmann factor and probability values in the respective sub-matrices. It is difficult to avoid a tensor product generating a large matrix for any large molecular system, thus we utilized a Hadamard (pointwise) product through fixed-size matrices for all atom pairs. This means the size of the final matrix is pre-determined at the beginning of the computation, and the Boltzmann factor and probability matrices for each atom pair should have the same size. These fixed-size matrices for all atom pairs are termed "Standard Matrices". Sizes of the original atom pair vectors with tens to hundreds of elements shown in Equation 1m below are far from enough for the final matrix size. Construction of the "Standard Matrices" relies on replication and tiling of the original atom pair vectors. Wherein, the vectors for each individual atom pairwise Boltzmann factor and probability are replicated in the "Standard Matrices" through all atom pairs. In order to perform the vector-to-matrix conversion, randomly scrambled permutations of the original vectors are needed. By introducing permutations to the original vector increases the diversity of atom pair combinations at different discrete distance values ($r_a$) in the MT computation, thereby increasing the sample size. We offer a detailed explanation in the latter paragraphs.

Using the bond probability vector as an example, permutations were made based on a vector with elements in order.

$$\mathbf{q}_k^{bond} = \begin{bmatrix} q_k^{bond}(r_1) \\ q_k^{bond}(r_2) \\ q_k^{bond}(r_3) \\ \vdots \\ q_k^{bond}(r_t) \end{bmatrix} \Rightarrow scram(\mathbf{q}_k^{bond})_i = \begin{bmatrix} q_k^{bond}(r_{t-2}) \\ q_k^{bond}(r_3) \\ q_k^{bond}(r_1) \\ \vdots \\ q_k^{bond}(r_2) \end{bmatrix} \quad (1m)$$

$\mathbf{q}_k^{bond}$ is the unscrambled probability vector of the kth atom pair with a bond constraint. t is the number of discrete probabilities with significant values. scram(X)$_i$ represents a randomly scrambled permutation of matrix X with i as the index number. The enlarged matrix of $\mathbf{q}_k^{bond}$ is represented as follow:

$$Q_k^{bond} = \begin{bmatrix} scram(q_k^{bond})_1 & scram(q_k^{bond})_{\alpha+1} & \cdots & scram(q_k^{bond})_{\beta-\alpha+1} \\ scram(q_k^{bond})_2 & scram(q_k^{bond})_{\alpha+2} & \cdots & scram(q_k^{bond})_{\beta-\alpha+2} \\ \vdots & \vdots & \ddots & \vdots \\ scram(q_k^{bond})_\alpha & scram(q_k^{bond})_{2\alpha} & \cdots & scram(q_k^{bond})_\beta \end{bmatrix} \quad (2m)$$

$Q_k^{bond}$ in Equation 2 is the "Standard Matrix" we built for the kth atom pair with a bond constraint. Although the sizes (the number t in Equation 1m) of different vectors $q_k$ vary under different constraints (i.e. $q_k^{bond}$, $q_k^{angle}$, $q_k^{torsion}$, $q_k^{long-range}$), $Q_k$ for all atom pairs was fixed to the same size with a predetermined permutation number $\alpha$ and $\beta$. The size of the Standard Matrix (SM) e.g. g rows ×h columns, must satisfy that the row number g is divisible by the sizes t of all the atom pair vectors $q_k$, so that each discrete probability $q_k(r_i)$ has an equal number of appearance in each SM $Q_k$. This definition is important to make sure the replication numbers for all Boltzmann factors and probabilities are identical in each SM, so that their relative probabilities are the same as in the original probability vector. Hadamard products of all the protein probability SMs (n as the total number of atom pairs) are then performed:

$$Q_P^{bond} = Q_1^{bond} \circ Q_2^{bond} \circ Q_3^{bond} \circ \cdots \circ Q_k^{bond} \circ \cdots \circ Q_n^{bond} \quad (3m)$$

$$Q_P^{final} = Q_P^{bond} \circ Q_P^{angle} \circ Q_P^{torsion} \circ Q_P^{long-range} \quad (4m)$$

Similarly, SMs for the ligand and the complex are given as:

$$Q_L^{final} = Q_L^{bond} \circ Q_L^{angle} \circ Q_L^{torsion} \circ Q_L^{long-range} \quad (5m)$$

$$Q_{PL}^{final} = Q_P^{bond} \circ Q_P^{angle} \circ Q_P^{torsion} \circ Q_P^{long-range} \circ Q_L^{bond} \circ Q_L^{angle} \circ Q_L^{torsion} \circ Q_L^{long-range} \circ Q_{PL}^{long-range} \quad (6m)$$

The Boltzmann factor SMs are obtained similarly:

$$Z_P^{bond} = Z_1^{bond} \circ Z_2^{bond} \circ Z_3^{bond} \circ \cdots \circ Z_k^{bond} \circ \cdots \circ Z_n^{bond} \quad (7m)$$

$$Z_P^{final} = Z_P^{bond} \circ Z_P^{angle} \circ Z_P^{torsion} \circ Z_P^{long-range} \quad (8m)$$

$$Z_L^{final} = Z_L^{bond} \circ Z_L^{angle} \circ Z_L^{torsion} \circ Z_L^{long-range} \quad (9m)$$

$$Z_{PL}^{final} = Z_P^{bond} \circ Z_P^{angle} \circ Z_P^{torsion} \circ Z_P^{long-range} \circ Z_L^{bond} \circ Z_L^{angle} \circ Z_L^{torsion} \circ Z_L^{long-range} \circ Z_{PL}^{long-range} \quad (10m)$$

From $Q_k^{bond}$, the bond probability matrix of one specific atom pair k, through $Q_P^{bond}$ the probability matrix of all protein atom pairs with bond constraints to $Q_{PL}^{final}$ the probability matrix of all atom pairs in the protein-ligand system, all the matrices have the same size such that the size of the SMs is the sample size of the atom pair combinations of the protein-ligand system. The advantage of using a pointwise product instead of a tensor product is that the size of the final matrix can be controlled at the beginning of the computation.

We use the two $sp^3$ carbon -$sp^3$ carbon bond terms in propane as an example to further explain the construction of the SMs using replication and tiling of the randomized vectors. The Boltzmann factor and probability vectors for each of the two bonds were modeled as unscrambled arrays:

$$Z_k^{bond} = \begin{bmatrix} z_k^{bond}(r_1) \\ z_k^{bond}(r_2) \\ \vdots \\ z_k^{bond}(r_a) \\ \vdots \\ z_k^{bond}(r_t) \end{bmatrix} = \begin{bmatrix} e^{-\beta E_k^{bond}(r_1)} \\ e^{-\beta E_k^{bond}(r_2)} \\ \vdots \\ e^{-\beta E_k^{bond}(r_a)} \\ \vdots \\ e^{-\beta E_k^{bond}(r_t)} \end{bmatrix} \quad (11m)$$

and $$q_k^{bond} = \begin{bmatrix} q_k^{bond}(r_1) \\ q_k^{bond}(r_2) \\ \vdots \\ q_k^{bond}(r_a) \\ \vdots \\ q_k^{bond}(r_t) \end{bmatrix} \quad (12m)$$

k indicates one $sp^3$ carbon-$sp^3$ carbon bond in propane and the discrete distance a goes from 1 through t and represent the distance increments. Disordered vectors are generated using random scrambling of the original vectors. An example of the randomly scrambled vector of the Boltzmann factor with the index number i is shown in Equation 13m. For a vector with t elements in it, the maximum number of permutation is t! (the maximum value of i). Each index number i in the scramble operation $scram(X)_i$ represents one certain arrangement order of elements in the vector.

$$scram(Z_k^{bond})_i = \begin{bmatrix} z_k^{bond}(r_3) \\ z_k^{bond}(r_{t-4}) \\ \vdots \\ z_k^{bond}(r_{t-1}) \\ \vdots \\ z_k^{bond}(r_5) \end{bmatrix} \quad (13m)$$

With $scram(Z_k^{bond})_i$ created, the SM for the kth $sp^3$ carbon-$sp^3$ carbon bond Boltzmann factor can be created by replication and tiling of the $scram(Z_k^{bond})_i$ s. For instance, to create a SM with 20 rows and 30 columns using a vector containing 5 Boltzmann factors (t=5), replication of the $scram(Z_k^{bond})_i$ in the SM would be generated as:

$$Z_k^{bond} = \begin{bmatrix} scram(Z_k^{bond})_1 & scram(Z_k^{bond})_5 & \cdots & scram(Z_k^{bond})_{117} \\ scram(Z_k^{bond})_2 & scram(Z_k^{bond})_6 & \cdots & scram(Z_k^{bond})_{118} \\ scram(Z_k^{bond})_3 & scram(Z_k^{bond})_7 & \ddots & scram(Z_k^{bond})_{119} \\ scram(Z_k^{bond})_4 & scram(Z_k^{bond})_8 & \cdots & scram(Z_k^{bond})_{120} \end{bmatrix} \quad (14m)$$

with $$scram(Z_k^{bond})_1 = \begin{bmatrix} z_k^{bond}(r_3) \\ z_k^{bond}(r_1) \\ z_k^{bond}(r_2) \\ z_k^{bond}(r_4) \\ z_k^{bond}(r_5) \end{bmatrix} \quad (15m)$$

as an example of one randomly scrambled vector.

Each vector $\boldsymbol{t}_k^{bond}$ is assumed to contain 5 elements thus 4 scrambled vectors tiled in a column makes 20 as the row number thus 120 scrambled vectors assemble the SM $\mathbf{Z}_k^{bond}$ with 600 elements.

For the probability SM, the same scramble and replication processes are performed. Furthermore, a probability value and a Boltzmann factor value corresponding to the same discrete distance ($r_a$) are mapped to each other in the probability and Boltzmann factor SMs. In other words, scrambled vectors of probabilities and Boltzmann factors scrambled in the same way (the same index number i) are in the same position in both the probability and Boltzmann factor SMs ($\mathcal{Q}_k^{bond}$ and $\mathbf{Z}_k^{bond}$). The mapping of probability and Boltzmann factor vectors in the SM $\mathcal{Q}_k^{bond}$ and SM $\mathbf{Z}_k^{bond}$ is illustrated in FIG. 13.

Figure 13:
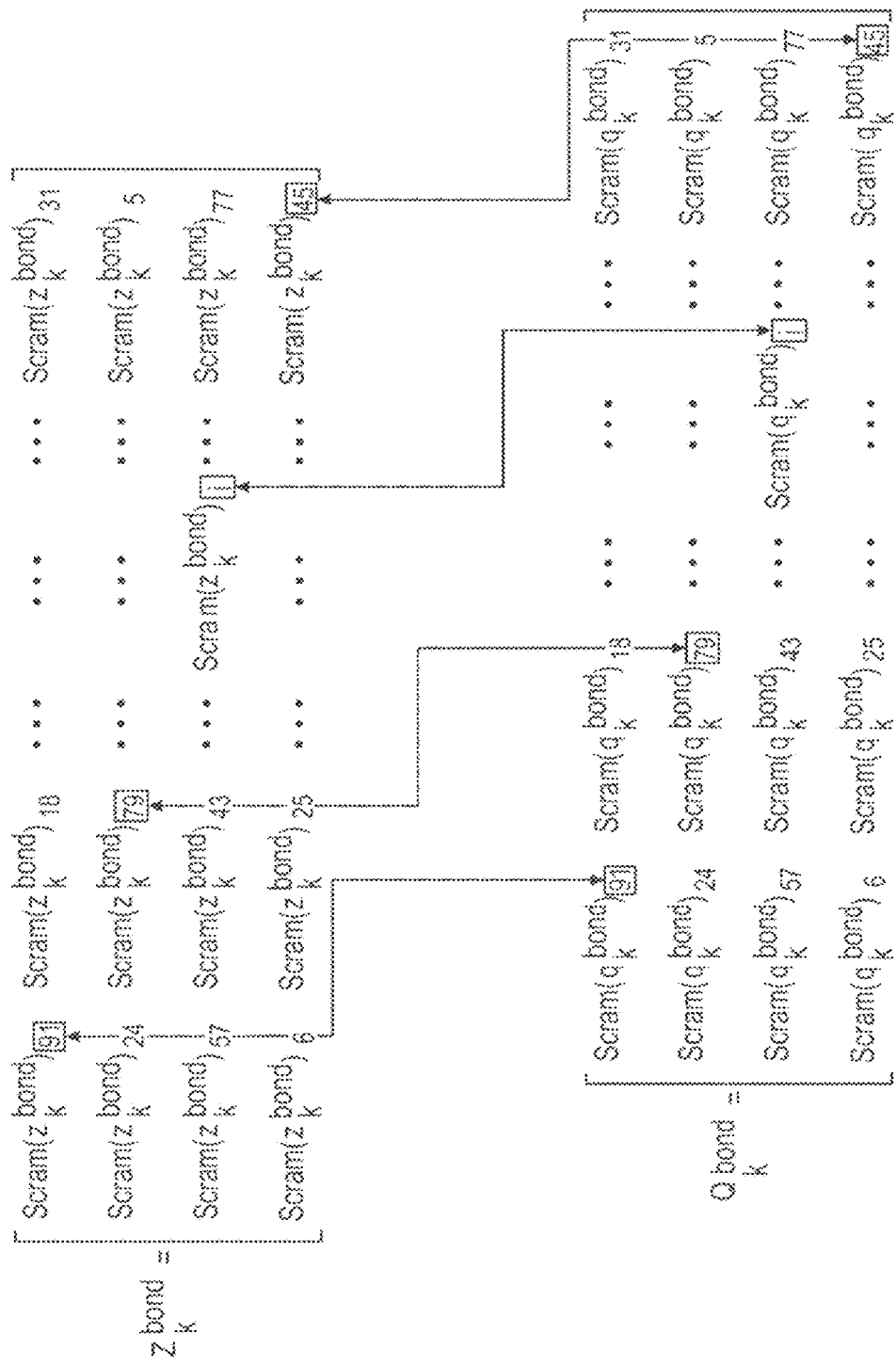
FIG. 13 depicts an example of the SM $\mathbf{Z}_k^{bond}$ and its corresponding SM $\mathcal{Q}_k^{bond}$, where SM refers to Standard Matrix, according to some example embodiments. The scramble operator index numbers with circles (red in the original) connected by arrows (blue in the original) indicate that scrambled vectors with the same scramble manner (the same index number i) in both $\mathbf{Z}_k^{bond}$ and $\mathcal{Q}_k^{bond}$ are tiled in the same position in both SMs.

FIG. 13 depicts an example of the SM $\mathbf{Z}_k^{bond}$ and its corresponding SM $\mathcal{Q}_k^{bond}$. The scramble operator index numbers with red circles connected by blue arrows indicate that scrambled vectors with the same scramble manner (the same index number i) in both $\mathbf{Z}_k^{bond}$ and $\mathcal{Q}_k^{bond}$ are tiled in the same position in both SMs.

$$\mathcal{Q}_l^{bond} = \begin{bmatrix} scram(\boldsymbol{q}_k^{bond})_{124} & scram(\boldsymbol{q}_k^{bond})_{240} & \cdots & scram(\boldsymbol{q}_k^{bond})_{157} \\ scram(\boldsymbol{q}_k^{bond})_{168} & scram(\boldsymbol{q}_k^{bond})_{231} & \cdots & scram(\boldsymbol{q}_k^{bond})_{216} \\ scram(\boldsymbol{q}_k^{bond})_{200} & scram(\boldsymbol{q}_k^{bond})_{197} & \ddots & scram(\boldsymbol{q}_k^{bond})_{178} \\ scram(\boldsymbol{q}_k^{bond})_{145} & scram(\boldsymbol{q}_k^{bond})_{135} & \cdots & scram(\boldsymbol{q}_k^{bond})_{132} \end{bmatrix} \quad (17m)$$

As we have mentioned, the maximum permutation number for a vector with t elements is t!. So there are around $10^{30}$ scrambled permutations with a bond vector containing about 30 elements, with which we could easily design thousands of $\mathbf{Z}_l^{bond}$ and $\mathcal{Q}_l^{bond}$ of a certain atom type pair using different tiling patterns. Using different tiling patterns for different atom type pairs increases the mix and match diversity of atom pairs at different discrete distance values ($r_a$) in the MT computation, and maximizes the degrees of freedom of the elements (shown in Equation 18m) in the pointwise product of the SMs of these two atom pairs (k and l).

$$\mathcal{Q}_k^{bond} \circ \mathcal{Q}_l^{bond} \circ Z_k^{bond} \circ Z_l^{bond} = \quad (18m)$$

$$\begin{bmatrix} q_k^{bond}(r_5)q_l^{bond}(r_3)z_k^{bond}(r_5)z_l^{bond}(r_3) & \cdots & q_k^{bond}(r_1)q_l^{bond}(r_4)z_k^{bond}(r_1)z_l^{bond}(r_4) \\ q_k^{bond}(r_2)q_l^{bond}(r_4)z_k^{bond}(r_2)z_l^{bond}(r_4) & \cdots & q_k^{bond}(r_3)q_l^{bond}(r_1)z_k^{bond}(r_3)z_l^{bond}(r_1) \\ \vdots & \ddots & \vdots \\ q_k^{bond}(r_3)q_l^{bond}(r_5)z_k^{bond}(r_3)z_l^{bond}(r_5) & \cdots & q_k^{bond}(r_4)q_l^{bond}(r_2)z_k^{bond}(r_4)z_l^{bond}(r_2) \end{bmatrix}$$

Due to the mapping of $scram(\boldsymbol{t}_k^{bond})_i$ and $scram(\boldsymbol{q}_k^{bond})_i$ in $\mathbf{Z}_k^{bond}$ and $\mathcal{Q}_k^{bond}$, probabilities and Boltzmann factors of the same discrete distance ($r_a$) encounter each other in the pointwise product, because each index number i in the $^{scram}(X)$ operation indicates a certain arrangement order of the elements in vector X. So that in the final SM, probabilities for each discrete distance ($r_a$) are assigned to the corresponding Boltzmann factors for the same ($r_a$).

Since the SM for the kth sp$^3$ carbon-sp$^3$ carbon bond Boltzmann factor is designed as in Equation 14, correspondingly, the probability SM is modeled as:

$$\mathcal{Q}_k^{bond} = \begin{bmatrix} scram(\boldsymbol{q}_k^{bond})_1 & scram(\boldsymbol{q}_k^{bond})_5 & \cdots & scram(\boldsymbol{q}_k^{bond})_{117} \\ scram(\boldsymbol{q}_k^{bond})_2 & scram(\boldsymbol{q}_k^{bond})_6 & \cdots & scram(\boldsymbol{q}_k^{bond})_{118} \\ scram(\boldsymbol{q}_k^{bond})_3 & scram(\boldsymbol{q}_k^{bond})_7 & \ddots & scram(\boldsymbol{q}_k^{bond})_{119} \\ scram(\boldsymbol{q}_k^{bond})_4 & scram(\boldsymbol{q}_k^{bond})_8 & \cdots & scram(\boldsymbol{q}_k^{bond})_{120} \end{bmatrix} \quad (16m)$$

Thus Boltzmann factor and probability SMs for the kth (one of the three) sp$^3$ carbon-sp$^3$ carbon bond in propane are modeled. In $\mathbf{Z}_k^{bond}$ and $\mathcal{Q}_k^{bond}$, 120 scrambled vectors represent 120 different scrambled permutations of vector $\boldsymbol{t}_k^{bond}$ and $\boldsymbol{q}_k^{bond}$ and tiled in a pattern from 1 through 120. SMs for lth ($1 \leq l \leq 2$, $l \in N$, $l \neq k$) are modeled in a similar way while with different tiling sequences for the $scram(X)_i$ vectors in both SMs. For and $\mathbf{Z}_l^{bond}$ and $\mathcal{Q}_l^{bond}$, tiling of the $scram(X)_i$ should use a different pattern. For instance a possible $\mathcal{Q}_l^{bond}$ with 120 scrambled vectors could be:

Using this replication and tiling scheme, the chance of element duplication in the final SM is extremely small due to the pointwise product of all atom pairwise SMs, thus maximizing the sampling size with a predetermined SM size. However, the size of the SMs is not arbitrary. Probability and Boltzmann factor vectors in each SM are randomly permutated and tiled, so that each element in the final matrices (i.e. $\mathcal{Q}_L^{final}$, $\mathcal{Q}_P^{final}$, $\mathcal{Q}_{PL}^{final}$, $\mathbf{Z}_L^{final}$, $\mathbf{Z}_P^{final}$, $\mathbf{Z}_{PL}^{final}$ in the equations above) is a probability or Boltzmann factor of one energy state in the protein-ligand system from a random combination of the chosen atom pairwise probabilities and Boltzmann factors. This indicates that with a fixed SM size, each time the pointwise product calculation is carried out it would generate different free energy values due to the random combination employed. Hence a SM size that ensures the convergence of the final free energy values is necessary for this pointwise approximation computation scheme to work effectively.

With the SM row number g fixed at 700 in order to be divisible by all vectors, 1, 1000, $10^8$, $10^{13}$ were selected as the SM column number h in order to generate 700, $7 \times 10^5$, $7 \times 10^{10}$ and $7 \times 10^{15}$ sampling sizes for the final SMs. In order to test the convergence of the free energy calculation using the SM pointwise product with different sizes, the binding free energy of one protein-ligand complex was calculated 100 times for each SM size, and RMSDs of the resultant binding free energies were collected for the four SM sizes. The protein-ligand complex with PDB ID 1LI2 was chosen for the test calculation. Binding affinity (pK$_d$) RMSDs for the four SM sizes are listed in Table 3.

TABLE 3 pK$_d$ RMSDs for 100 rounds binding affinity calculations against the protein-ligand complex 1LI2 using the SM pointwise product with four different SM sizes.

| SM sizes | 700 | 7 × 10$^5$ | 7 × 10$^{10}$ | 7 × 10$^{15}$ |
|---|---|---|---|---|
| PK$_d$ RMSD | 0.059 | 0.012 | 0.011 | 0.011 |

The test result shows that the pK$_d$ RMSD for SM sizes of 7×10$^5$, 7×10$^{10}$ and 7×10$^{15}$ only differ by 0.001 and they all generate very low RMSDs (0.012, 0.011 and 0.011). We concluded that MT calculations with sample sizes of 7×10$^5$ is sufficient to ensure free energy convergence.

Using the pointwise product approximation, a protein-ligand complex would create several thousand SMs on average. For a laptop with a Intel(R) Core(TM) i7 CPU with 8 cores at 1.73 GHz and 8 Gb of RAM, it takes 6 seconds to calculate the pose and binding affinity for the protein-ligand complex 1LI2 and on average less than a minute to calculate the pose and binding free energy of one of the 795 protein-ligand complexes studied herein. If the SM size is increased to 7×10$^{10}$, the computation time required for 1LI2 increases to 8 minutes and on average it increases to around 20 minutes using the same laptop. Hence, this approach is faster than using MD or MC simulations to collect the energies of 7×10$^5$ to 7×10$^{10}$ protein-ligand poses. Future speed-ups are clearly possible using state of the art CPUs and GPUs and this is work that is underway.

Example No. 3

Another important issue for statistical potentials is that their performance relies crucially on available structural data. Substantial protein and small molecule structural databases support the success of statistical potentials in many application areas e.g., protein folding and protein ligand binding. Structural databases with accurately positioned crystal waters including the Protein Databank (PDB) and the Cambridge Structural Database (CSD) are used herein to build pairwise models of solute-solvent interactions.

Statistical potentials, from the theoretical point of view build on the concept of the potential of mean force (PMF), are developed using structural information regarding structurally characterized molecular systems. A mean potential between specific atom pairs ($\omega^{(2)}(r_{12})$) is directly generated from the frequency of occurrence of the atom pairs contained in a large database of molecules:

$$\omega_{ij}^{(2)}(r_{12}) = -\frac{1}{\beta}\ln(g^{(2)}(r_{12})) = -\frac{1}{\beta}\ln\left(\frac{\rho_{ij}(r_{12})}{\rho_{ij}^*(r_{12})}\right) \quad (1n)$$

where g$^{(2)}$ is called a correlation function. $\beta=1/k_B T$ and k$_B$ is the Boltzmann constant and T is the temperature. $\rho_{ij}(r)$ is the number density for the atom pairs of types i and j observed in the known protein or ligand structures and $\rho^*_{ij}(r)$ is the number density of the corresponding pair in the background or reference state. A central problem for statistical potentials is to model specific atom pairwise interactions removed from the background energy. In protein-ligand complexes, geometric information, i.e. atom pairwise radial distributions, represents an averaged effect of all interactions in chemical space, including bond, angle, torsion, and long-range non-covalent forces. Converting these radial distributions into energy functions is a challenge.

Computing free energies requires the availability of accurate energy functions, but also requires extensive phase space sampling. In the NVT ensemble the Helmholtz solvation free energy is calculated using the ratio of partition functions given as:

$$\Delta G_{solv}^L \approx \Delta A_{solv}^L = -RT\ln\left[\frac{Z_{LS}}{Z_L}\right] = -RT\ln\left[\frac{\int e^{-\beta E_{LS}(r)}dr}{\int e^{-\beta E_L(r)}dr}\right] \quad (2n)$$

Equation 2 represents the free energy change of transferring a molecule (L) from vacuum to aqueous solution. Many sampling methods have proven effective, e.g. molecular dynamics (MD) and Monte Carlo (MC) methods; however, thoroughly sampling phase space is challenging for brute-force methods. A new sampling method, which we call the Movable Type (MT) method, was developed by our group in an attempt to avoid some of the pitfalls encountered by the more computationally intensive sampling methods. Via sampling of all atom pairwise energies, at all possible distances, using pre-built databases and then combining these energies for all atom pairs found in the molecular system of interest, the MT sampling method was able to accurately estimate binding free energies as well as protein-ligand poses.

In the following paragraphs, we discuss in detail the data selection process, atom type recognition and a novel reference state model that aided in the development of a new solute-solvent statistical potential method, which when combined with the MT sampling method predicts solvation free energies. To validate our model a curated set of 393 small molecule solvation free energies, collected in the MNSol database of Cramer and Truhlar, were used. Our computed results were then compared to those obtained using the MM-GBSA and MM-PBSA models available in AMBER against the same data set.

Movable Type (MT) method is a free energy method that generates the ensemble of the molecular system of interest using pairwise energies and probabilities. The term "Movable Type" originates from the printing technique where a database of symbols (letters, numerals, etc.) is created and then assembled using a movable type system. Similarly, MT free energy calculations start from the construction of a large database containing interaction energies between all classes of atom pairs found in the chemical space under investigation. An atom pairwise energy function is required to create the database and the modified KECSA model is employed herein.

With an atom pairwise energy database, molecular "printing" is then performed by assembling the pairwise energies using a "printing forme". A fixed-size matrix (Z-matrix) is introduced to represent the Boltzmann-weighted energy ensemble, in which atom pairwise energies at different distances are assembled to simultaneously represent the ensemble and free energies of the chemical space under investigation.

Creation of the Z-matrix starts from the first atom pair in the observed molecular system, with all elements in the matrix as Boltzmann-weighted energies of the observed atom pair at different distances, selected from the energy database.

$$Z_k^L = \begin{bmatrix} e^{-\beta E_k^L(r_1)} & e^{-\beta E_k^L(r_{i+1})} & \cdots & e^{-\beta E_k^L(r_{n-i+1})} \\ e^{-\beta E_k^L(r_2)} & e^{-\beta E_k^L(r_{i+2})} & \cdots & e^{-\beta E_k^L(r_{n-i+2})} \\ \vdots & \vdots & \ddots & \vdots \\ e^{-\beta E_k^L(r_j)} & e^{-\beta E_k^L(r_j)} & \cdots & e^{-\beta E_k^L(r_n)} \end{bmatrix} \quad (3n)$$

$Z_k^L$ (Z-matrix) in equation 3 represents a Boltzmann-weighted energy (Boltzmann factor) matrix for the kth atom pair in the $\mathbb{Z}$ observed molecule L containing energies ranging from distance $r_1$ to $r_n$. An inner product of Z-matrices results in the Boltzmann-weighted energy combinations between different atom pairs at different distances with a sampling size of n (matrix size), as is shown in equation 4n.

$$\mathcal{Z}_{12}^L = \mathcal{Z}_1^L \cdot \mathcal{Z}_2^L \quad (4n)$$

$$= \begin{bmatrix} e^{-\beta(E_1^L(r_1)+E_2^L(r_1))} & e^{-\beta\binom{E_1^L(r_{i+1})+}{E_2^L(r_{i+1})}} & \cdots & e^{-\beta\binom{E_1^L(r_{n-i+1})+}{E_2^L(r_{n-i+1})}} \\ e^{-\beta(E_1^L(r_2)+E_2^L(r_2))} & e^{-\beta\binom{E_1^L(r_{i+2})+}{E_2^L(r_{i+2})}} & \cdots & e^{-\beta\binom{E_1^L(r_{n-i+2})+}{E_2^L(r_{n-i+2})}} \\ \vdots & \vdots & \ddots & \vdots \\ e^{-\beta(E_1^L(r_i)+E_2^L(r_i))} & e^{-\beta\binom{E_1^L(r_j)+}{E_2^L(r_j)}} & \cdots & e^{-\beta(E_1^L(r_n)+E_2^L(r_n))} \end{bmatrix}$$

Performing random disordered permutations to the Z-matrices maximizes the variety of energy combinations at different distances. Based on the assumption that the molecular energy is separable into atom pairwise energies in the same molecular system, an inner product of disordered matrices over all atom pairs in the observed molecule derives the final Z-matrix representing the collection of Boltzmann-weighted energies with n configurations for the entire molecule L (equation 5).

$$\mathcal{Z}_{total}^L = \text{disorder}(\mathcal{Z}_1^L) \cdot \text{disorder}(\mathcal{Z}_2^L) \cdot \ldots \cdot \text{disorder}(\mathcal{Z}_k^L) = \quad (5n)$$

$$\begin{bmatrix} e^{-\beta(E_1^L(r_5)+E_2^L(r_3)+\ldots+E_k^L(r_i))} & e^{-\beta(E_1^L(r_i)+E_2^L(r_{n-1})+\ldots+E_k^L(r_{i+2}))} & \cdots & e^{-\beta(E_1^L(r_3)+E_2^L(r_{i-1})+\ldots+E_k^L(r_n))} \\ e^{-\beta(E_1^L(r_{i-1})+E_2^L(r_i)+\ldots+E_k^L(r_1))} & e^{-\beta(E_1^L(r_{i-1})+E_2^L(r_2)+\ldots+E_k^L(r_{i+1}))} & \cdots & e^{-\beta(E_1^L(r_{i-1})+E_2^L(r_{i-2})+\ldots+E_k^L(r_3))} \\ \vdots & \vdots & \ddots & \vdots \\ e^{-\beta(E_1^L(r_n)+E_2^L(r_i)+\ldots+E_k^L(r_i))} & e^{-\beta(E_1^L(r_i)+E_2^L(r_{i-1})+\ldots+E_k^L(r_2))} & \cdots & e^{-\beta(E_1^L(r_{i-2})+E_2^L(r_{n-2})+\ldots+E_k^L(r_i))} \end{bmatrix}$$

As the final Z-matrix may contain unreasonable distance combinations between different atom pairs, a Q-matrix of atom pairwise radial distribution probabilities is introduced in order to avoid physically unreasonable combinations between different atom pairs at certain bond lengths, angles and torsions. The elements in the Q-matrix were collected from a large structural database containing 8256 protein crystal structures from PDBBind v2013 database and 44766 small molecules from both PDBBind v2013 and the CSD small molecule database. Corresponding to each element in an atom pairwise Z-matrix, there is a distance-dependent probability value chosen from the radial distribution probability database of the same atom pair type. Q-matrices matching the composition of the corresponding Z-matrix are also assembled using inner products. The final Q-matrix for the molecule of interest is normalized before being multiplied by the final Z-matrix, assuring that the overall probability is 1. The sum of the final matrix ($\mathcal{C}_{total}^L$) gives the ensemble average of the Boltzmann factors with a sampling size o/n (m\trix size).

$$\langle e^{-\beta EL} \rangle = \text{sum}(\mathcal{C}_{total}^L) = \text{sum}(\mathcal{Q}_{total}^L \mathbf{Z}_{total}^L) \quad (6n)$$

Hence, with a pre-defined sampling size of n for the Z and Q matrices, the energies of different molecular conformations can be generated simultaneously via matrix products over all atom pairs. The solvation free energy is then calculated by incorporating the ensemble average of the Boltzmann factors into:

$$\Delta G_{solv}^L \approx -RT\ln\left[\frac{Z_{LS}}{Z_L}\right] = \quad (7n)$$

$$-RT\ln\left[\frac{\int e^{-\beta E_{LS}(r)}dr}{\int e^{-\beta E_L(r)}dr}\right] = -RT\ln\left[\frac{DOF_{LS}\langle e^{-\beta E_{LS}(r)}\rangle}{DOF_L\langle e^{-\beta E_L(r)}\rangle}\right]$$

where the energy of the molecule in solution ($E_{LS}$) is modeled as:

$$E_{LS}(r) = E_L(r) + E_{L-S\ interaction}(r) \quad (8n)$$

$DOF_{LS}$ and $DOF_L$ indicate the degrees of freedom of the molecule in solution and in the gas phase, which were assigned the same value in the current implicit water model for simplicity.

The free energy is computed directly from the NVT ensemble avoiding issues related to the additivity of the free energy. Theoretically and experimentally it can be shown that the energy can be decomposed, while the entropy and free energies cannot. Herein we assemble the interaction energies using Equation 8n and then place this into Equation 7n to directly compute the free energy, thereby, avoiding issues related to the decomposition of the free energy. This is a real advantage of the MT method and in future work we will describe using this approach to compute both entropies and energies using statistical mechanics.

The MT energy sampling method can incorporate both an explicit and implicit water model into a solvation free energy calculation. Our previous attempt utilized a simple continuum ligand-solvent interaction model. A new semi-continuum water model is developed herein, in which the solute-solvent interaction is calculated by placing water molecules around the solute.

Water molecules were modeled as isotropic rigid balls with van der Waals radii of 1.6 Å. Water molecules were placed into isometric solute-surrounding solvent layers, starting from the solute's water accessible surface until 8 Å away from the solute's van der Waals surface with an increment of 0.005 Å per layer. The number of water molecules was limited by comparing their maximum cross-sectional areas with the solvent accessible surface area at each solvent layer for each atom in the solute molecules. The number of water molecules ($N_w$) accessible to each atom at distance R away from the atomic center of mass is rounded down via filtering using the maximum cross-sectional area ($S_w$) of water with the atomic solvent accessible surface area ($S_a$) in the solvent layer at distance R.

$$N_w(r) = \text{floor}\left(\frac{S_a(r)}{S_w}\right) \tag{9n}$$

According to FIG. 1, the maximum cross-sectional areas ($S_w$) of a water molecule is calculated as:

$$S_w = \int_{\frac{\pi}{2}-\theta}^{\frac{\pi}{2}} 2\pi(R_a + R_w)R_w \sin\left(\frac{\pi-\theta}{2}\right) d\left(\frac{\pi}{2} - \theta\right) \tag{10n}$$

$$= 2\pi(R_a + R_w)R_w \cos\left(\frac{\pi-\theta}{2}\right)$$

where $R_w$ and $R_a$ are the van der Waals radii for water and the atom in the solute molecule respectively.

The Boltzmann factor matrix for the $k^{th}$ solute atom-water ($\mathbf{Z}_k^{A-S}$) interaction is defined as a Boltzmann weighted solute atom-water energy multiplied by the number of accessible water molecules at the different distances. Multiplication of the Z-matrices for all solute atom-water interactions composes the final solute molecule-water Z-matrix ($\mathbf{Z}_{total}^{L-S}$) which when multiplied by the Z-matrix for the intra-solute molecular interactions ($\mathbf{Z}_{total}^{L}$) derives the final Z-matrix for the solute-solvent complex system ($\mathbf{Z}_{total}^{LS}$). Multiplication of the final Z-matrix with its corresponding normalized Q-matrix generates the Boltzmann-weighted energy ensemble ($\mathcal{C}_{total}^{LS}$). With the energy ensembles for the solute molecule ($\mathcal{C}_{total}^{L}$) and solute-solvent complex ($\mathcal{C}_{total}^{LS}$), the solvation free energy is calculated using equation 14n.

Figure 14:
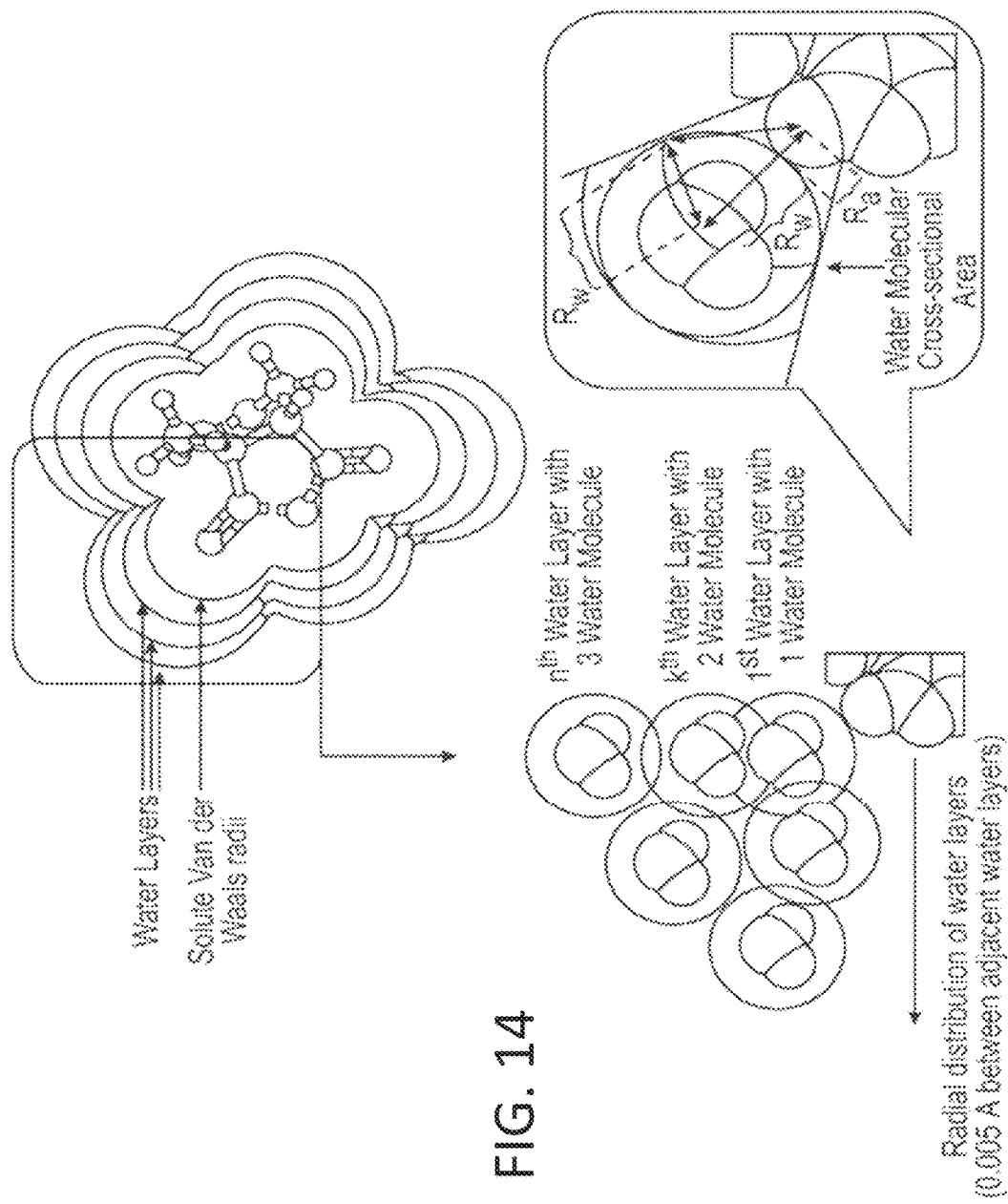
FIG. 14 depicts factors involved in the implicit-solvent model in the (KECSA-Movable Type Implicit Solvation Model) KMTISM method, according to some example embodiments.

FIG. 14 depicts the factors involved in the implicit-solvent model in the KMTISM method.

KECSA Energy Function (Data Collection)

A collection of structural information is the first requirement to assemble a statistical potential. Many crystal structures in the Cambridge Structural Database (CSD) represent small molecules co-crystalized with water molecules. Moreover, the Protein Data Bank (PDB) also contains a large number of protein-ligand complexes with water molecules at the interface between binding pockets and ligand molecules albeit the resolution of these structures are poorer than typically encountered in the CSD. Since our goal was to construct a solvation energy model focusing on small molecules, the CSD small molecule database became our primary resource for structural data. In order to data mine the CSD we only examined structures with (1) an R factor less than 0.1 and (2) all polymer structures and molecules with ions were excluded. The resulting data set selected contained 7281 small molecules surrounded by crystal water molecules.

Atom Type Recognition

Statistical potentials are derived by converting the number density distributions between two atoms or residues to energies; hence, they are "fixed-charge" models for the selected atom or residue pairs. In order to differentiate atoms of the same type but with different electron densities, a detailed atom type categorization has been employed where 21 atom types (shown in Table 1) were chosen from the database as having statistically relevant water molecule contact information contained within the CSD.

$$\mathcal{Z}_k^{A-S} = \begin{bmatrix} e^{-\beta E_k^{A-S}(r_1)N_w(r_1)} & e^{-\beta E_k^{A-S}(r_{i+1})N_w(r_{i+1})} & \cdots & e^{-\beta E_k^{A-S}(r_{n-i-1})N_w(r_{n-i+1})} \\ e^{-\beta E_k^{A-S}(r_2)N_w(r_2)} & e^{-\beta E_k^{A-S}(r_{i+2})N_w(r_{i+2})} & \cdots & e^{-\beta E_k^{A-S}(r_{n-i-2})N_w(r_{n-i+2})} \\ \vdots & \vdots & \ddots & \vdots \\ e^{-\beta E_k^{A-S}(r_i)N_w(r_i)} & e^{-\beta E_k^{A-S}(r_j)N_w(r_j)} & \cdots & e^{-\beta E_k^{A-S}(r_n)N_w(r_n)} \end{bmatrix} \tag{11n}$$

$$\mathcal{Z}_{total}^{L-S} = \text{disorder}(\mathcal{Z}_1^{A-S}) \cdot \text{disorder}(\mathcal{Z}_2^{A-S}) \cdot \ldots \cdot \text{disorder}(\mathcal{Z}_n^{A-S}) \tag{12n}$$

$$\mathcal{C}_{total}^{LS} = \overline{\mathcal{Q}}_{total}^{LS} \square \mathcal{Z}_{total}^{LS} = \overline{\mathcal{Q}}_{total}^{L-S} \square (\mathcal{Q}'')_{total}^{L} \square \mathcal{Z}_{total}^{L-S} \square \mathcal{Z}_{total}^{L} \tag{13n}$$

$$\mathcal{C}_{total}^{LS} = \overline{Q}_{total}^{LS} \cdot Z_{total}^{LS} = \overline{Q}_{total}^{L-S} \cdot \overline{Q}_{total}^{L} \cdot Z_{total}^{L-S} \cdot Z_{total}^{L}$$

$$\Delta G_{solv}^L \approx -RT \ln\left[\frac{Z_{LS}}{Z_L}\right] \tag{14n}$$

$$= -RT \ln\left[\frac{\langle e^{-\beta E_{LS}(r)} \rangle}{\langle e^{-\beta E_L(r)} \rangle}\right]$$

$$= -RT \ln\left[\frac{\text{sum}(\mathcal{C}_{total}^{LS})}{\text{sum}(\mathcal{C}_{total}^{L})}\right]$$

$$= -RT \ln\left[\frac{\text{sum}(\overline{\mathcal{Q}}_{total}^{LS} \square \mathcal{Z}_{total}^{LS})}{\text{sum}(\overline{\mathcal{Q}}_{total}^{L} \square \mathcal{Z}_{total}^{L})}\right]$$

TABLE 4

List of 21 atom types in the current solvation model

| Atom Type | Description |
|---|---|
| C1 | sp1 carbon |
| C2 | sp2 carbon |
| C3 | sp3 carbon |
| Car | aromatic carbon |
| N2 | sp2 nitrogen |
| N3 | sp3 nitrogen |
| N4 | positively charged nitrogen |
| Nam | amide nitrogen |
| Nar | aromatic nitrogen |
| Npl3 | trigonal planar nitrogen |
| Ow | water oxygen |
| O2 | sp2 oxygen |
| O3 | hydroxyl oxygen |
| OE | ether and ester sp3 oxygen |
| Oco2 | carboxylate, sulfate and phosphate oxygen |
| S2 | sp2 sulfur |
| S3 | sp3 sulfur |
| P3 | sp3 phosphorous |
| F | Fluorine |
| Cl | Chlorine |
| Br | Bromine |

Energy Function Modeling

The pairwise radial distribution is a mixed consequence of direct pairwise contacts and indirect environmental effects. Intrinsically, statistical potentials have difficulty in separating out various chemical environment effects on the observed atoms, thereby generating a major source of error in this class of models. As noted by Thomas and Dill, over-represented contacts in a structural database could mask the presence of other contacts. With the reference state pre-supposing a uniform availability of all contacts, quantitatively minor contacts are always underestimated in statistical potentials. A new statistical potential energy function called KECSA developed in our group defines a new reference state attempting to eliminate the contact masking due to quantitative preferences.

Unlike traditional statistical potentials using a reference state mimicking the ideal gas state, KECSA defines a reference state energy or background energy as the energy contributed by all atoms surrounding the observed atom pairs. It introduces a reference state number distribution modeled by a linear combination of the number distribution under mean force ($n_{ij}(r)$) and the number distribution of an ideal gas state $$\left(\frac{N_{ij}}{V} 4\pi r^2 \Delta r\right):$$

$$n_{ij}^{**}(r) = \left(\frac{N_{ij}}{V} 4\pi r^2 \Delta r\right)x + (n_{ij}(r))(1-x) \quad (15n)$$

where x indicates the intensity of the observed atom pairwise interaction in the chemical space V. This definition puts the number distribution of one certain observed atom pair in the reference state somewhere between the ideal gas state and the "mean force" state, depending on its relative strength. Stronger interactions have background energies closer to an ideal gas state while weaker interactions have background energies approaching the mean force state energy contributed by all atoms in the chemical space.

To build a KECSA energy function modeling solvent, solute and solvent-solute interactions requires us to define an "x term" for each atom pairwise interaction. Several approaches have been used to model x in our knowledge-based energy function. In the original KECSA, we simply used the number ratio of the chosen atom pair i and j over the total atom pairs in the chemical space to represent the intensity x. Meanwhile, based on the fact that all contacts are uniformly available in the chemical space given by the selected database, we assigned an identical x for every atom pair found in the given chemical space.

$$n_{ij}^{**}(r) = \left(\frac{N_{ij}}{V} 4\pi r^2 \Delta r\right)x + (n_{ij}(r))(1-x) = \quad (16n)$$

$$\left(\frac{N_{ij}}{V} 4\pi r^2 \Delta r\right)\frac{1}{N_t} + (n_{ij}(r))\left(1 - \frac{1}{N_t}\right)$$

where $N_t$ is the total atom type number in the chemical space.

The original model of $n_{ij}^{**}(r)$ is based on the notion that every atom pair has an equal contact opportunity in a background energy contributed by the other atom pairs, while neglecting the fact that the background energies have different effects on atom pairwise distributions with different interaction strengths (say atom i and j under a covalent bond constraint compared to atom k and l under a non-bond interaction constraint).

A more accurate nij**(r) model is introduced herein that takes every atom pairwise contact as a energy state distributed between an ideal gas state energy and mean force state energy following a Boltzmann distribution in the reference state. In this way the x factor is defined as:

$$x = \frac{N_{ij}(r)e^{-\beta E_{ij}(r)}}{\sum_i^n \sum_j^n N_{ij}(r)e^{-\beta E_{ij}(r)}} \quad (17n)$$

where $e^{-\beta E_{ij}(r)}$ is the Boltzmann factor and $N_{ij}(r)$ is the degeneracy factor (contact number) for atom type pair i and j.

With the x term built up as a probability of all contacts, the number distribution of the observed atom pair in the background state $n_{ij}^{**}(r)$ is modeled as:

$$n_{ij}^{**}(r) = \left(\frac{N_{ij}}{V} 4\pi r^2 \Delta r\right)\frac{N_{ij}(r)e^{-\beta E_{ij}(r)}}{\sum_i^n \sum_j^n N_{ij}(r)e^{-\beta E_{ij}(r)}} + \quad (18n)$$

$$(n_{ij}(r))\left(1 - \frac{N_{ij}(r)e^{-\beta E_{ij}(r)}}{\sum_i^n \sum_j^n N_{ij}(r)e^{-\beta E_{ij}(r)}}\right)$$

Hence we can build the energy function for each atom type pair as:

$$E_{ij}(r) = -\frac{1}{\beta}\ln\left(\frac{n_{ij}(r)}{n_{ij}^*(r)}\right) \quad (19n)$$

-continued $$= -\frac{1}{\beta}\ln\left[\frac{n_{ij}(r)}{\left(\frac{N_{ij}}{V}4\pi r^2 \Delta r\right)x + (n_{ij}(r))(1-x)}\right]$$

$$= \frac{1}{\beta}\ln\left[x\left(\frac{N_{ij}3r^2\Delta r}{R^3 n_{ij}(r)}\right) + (1-x)\right]$$

$$= \frac{1}{\beta}\ln\left[\begin{array}{c}\frac{N_{ij}(r)e^{-\beta E_{ij}(r)}}{\sum_i^n \sum_j^n N_{ij}(r)e^{-\beta E_{ij}(r)}}\left(\frac{N_{ij}3r^2\Delta r}{R^3 n_{ij}(r)}\right) + \\ \left(1 - \frac{N_{ij}(r)e^{-\beta E_{ij}(r)}}{\sum_i^n \sum_j^n N_{ij}(r)e^{-\beta E_{ij}(r)}}\right)\end{array}\right]$$

In equation 19n, with the energy functions built up in the chosen chemical space, each $E_{ij}(r)$ can be derived iteratively at discrete distance points. Using this model every $E_{ij}(r)$ derived using the KECSA energy function is never a mean force potential between atom pair i and j as found in traditional statistical potentials. Instead, $E_{ij}(r)$ represents a pure atom pairwise interaction energy between i and j because the reference state energy defined in KECSA is a background energy contributed by all other atom pairs, and not just the ideal gas state energy.

Test Set Selection

Two major differences between (KECSA-Movable Type Implicit Solvation Model) KMTISM and other continuum solvation models are (1) the MT method calculates the free energy change using a ratio of partition functions in the NVT ensemble, while traditional continuum solvation models separate the Gibbs free energies into linear components with enthalpy and entropy components. (2) Electrostatic interactions are implicit via the categorization of pairwise atom-types in the KECSA model while they are calculated explicitly using classical or QM based energy calculation approaches. In this manner, KMTISM can be viewed as the null hypothesis for the addition of explicit electrostatic interactions. If electrostatic interactions are added to a model it should outperform the knowledge-based approach, if not, the explicit electrostatic model is not an improvement over the implicit inclusion of this key interaction. A key concern for the KMTISM method is the validity of using pre-constructed atom-type pairwise energy data in free energy calculations for molecules with similar atoms, which differ in their chemical environments. Hence, KMTISM was examined with test compounds containing C, O, N, S, P, and halogen atoms within different functional groups. Given that the KECSA energy function was parameterized using organic structural data, validation focused on reproducing the aqueous solvation free energy for drug-like molecules. The Minnesota Solvation Database is a well-constructed data set, including aqueous solvation free energies for 391 neutral molecules and 144 ions. This data set was filtered down to 372 neutral molecules and 21 ions in our test set via the exclusion of (1) inorganic molecules, and (2) molecules with atom types not represented in the KECSA potential. This test set, including various hydrocarbons, mono- and polyfunctional molecules with solvation free energies ranging from −85 to 4 kcal/mol, was further classified into different subsets based on the functional groups within the molecules. Some molecules were included in several subsets due to their polyfunctional nature.

Carbon, nitrogen and oxygen are essential elements in organic molecules. More than one half of the compounds in the neutral test set (219 out of 372 compounds) were composed exclusively of C, N and O atoms. From the Minnesota Solvation Database we created 4 subsets from these 219 molecules: 41 hydrocarbons, 91 molecules with oxygen based functional groups, 44 molecules with nitrogen based functional groups and 43 molecules with mixed N and O functional groups. Validation also focused on molecules with sulfur, phosphorus, and halogen atoms, which play important roles in organic molecules. A test set with only halocarbons was created for the purpose of avoiding interference from other polar atoms. Sulfur and phosphorus, on the other hand, are often contained in oxyacid groups in organic molecules. Collected from the neutral data set, a test set with sulfur or phosphorus-containing molecules was composed. Heterocycles, amides and their analogs are pervasive in drug-like molecules and are well represented in the Minnesota Solvation Database. 37 heterocyclic compounds and 33 amides and their analogs were categorized into two subsets. In addition, 28 molecules containing three or more different functional groups were selected to provide a challenging test with complex and highly polar molecules. The ion test set was limited to biologically relevant ions herein resulting in positively charged nitrogen and negatively charged carboxylate oxygen subsets. In this way 21 ions were chosen from Minnesota Solvation Database (11 cations and 10 anions). Alkoxide ions among others present in the Minnesota Solvation Dataset will be examined in the future with the aid of molecular dynamics simulation of ion-water interactions for these ions, but were excluded herein. Calculation results using KMTISM, MM-GBSA and MM-PBSA for all test sets are contained in the Supporting Information. Only statistical data are given in Table 5 and Table 6 in this manuscript.

Comparison with MM-GBSA and MM-PBSA results

Data analysis covered solvation free energy calculations for all subsets using KMTISM along with the corresponding MM-GBSA and MM-PBSA results. Both MM-GBSA and MM-PBSA calculation were performed using AMBER with the General AMBER force field (GAFF). GB parameters were set as: igb=2 and saltcon=0.100. In the PB calculation, istrng=0.100.

Against the neutral molecule test set, KMTISM and MM-PBSA gave comparable correlation coefficients ($R^2$) and both were better than MM-GBSA. According to Kendall's tau values, MM-PBSA outperformed the other two methods in ranking ability, with KMTISM as the second best. In terms of accuracy of the models, KMTISM has the lowest root-mean-square error (RMSE), while the RMSE values for MM-GBSA and MM-PBSA were almost twice as large. A plot of the experimental data vs. calculated data is given in FIG. 2 while the statistical results are summarized in Tables 5 and 6.

For the purpose of a more thorough analysis, a linear scaling model was applied to all three methods using equation 20 in order to bring their respective regression lines closer to y=x. Linear scaling, due to its dataset dependence, did not improve the performance of the methods, but instead, it provided a way to examine the deviation of the calculated results from their regression lines.

$$y_{corrected} = \frac{(y_{raw} - b)}{a} \tag{20n}$$

Here a and b are the slope and the intercept of the regression line between experimental data and computed data, respectively.

The MM-GBSA and MM-PBSA results suggested a biased regression against the experimental solvation energies (y=1.3186x−1.2902 for MM-GBSA and y=1.5095x−0.1556 for MM-PBSA, where x and y represent the experimental and calculated solvation free energies). The slopes of their regression lines indicated an overestimation of the solvation free energies using these two methods. The significant improvement in RMSE values for MM-GBSA and MM-PBSA after the linear scaling as well as their correlation coefficient ($R^2$ and Kendall's tau) values indicate that they have a better ranking ability than free energy prediction. On the other hand, KMTISM's regression function (y=1.1078x−0.0811) affected the RMSE to a lesser extent.

Among all datasets, the hydrocarbon set was reproduced with the lowest RMSE value for all of the models, while unsaturated hydrocarbons proved more difficult for KMTISM than the other two methods. The drop in $R^2$ for KMTISM was due to overestimation of the solvation free energies of unsaturated hydrocarbons, e.g. the two compounds with the largest error (~2 kcal/mol) were ethene and s-trans-1,3-butadiene, where all heavy atoms were $sp^2$ hybridized. In the KECSA training set, which includes mostly drug-like molecules, different adjacent polar functional groups significantly altered the electron densities of adjacent unsaturated carbon atoms (via delocalization, for example) and this varies the electrostatic characteristics of these carbon atoms more than that seen in the case of $sp^3$ hybridized carbon.

TABLE 5

Performance of KMTISM, MM-GBSA and MM-PBSA for the prediction of the solvation free energies of neutral molecules.

|  | KMTISM | MM-GBSA | MM-PBSA | KMTISM | MM-GBSA | MM-PBSA |
|---|---|---|---|---|---|---|
|  | Total Neutral Molecule Set | | | Amide Set | | |
| $R^2$ | 0.792 | 0.734 | 0.804 | 0.660 | 0.493 | 0.509 |
| Kendall's tau | 0.755 | 0.708 | 0.793 | 0.568 | 0.484 | 0.465 |
| Raw RMSE (kcal/mol) | 2.597 | 4.629 | 4.647 | 4.368 | 8.666 | 9.717 |
| Scaled RMSE (kcal/mol) | 2.248 | 2.634 | 2.160 | 3.852 | 4.885 | 4.663 |
|  | Hydrocarbon Set | | | Halocarbon Set | | |
| $R^2$ | 0.699 | 0.906 | 0.954 | 0.648 | 0.004 | 0.594 |
| Kendall's tau | 0.663 | 0.748 | 0.887 | 0.656 | 0.091 | 0.625 |
| Raw RMSE (kcal/mol) | 0.858 | 1.179 | 0.925 | 1.052 | 2.768 | 1.148 |
| Scaled RMSE (kcal/mol) | 0.845 | 0.498 | 0.332 | 1.030 | 2.063 | 1.109 |
|  | Oxygenated Molecule Set | | | Organosulfur & Organophosphorus Set | | |
| $R^2$ | 0.829 | 0.881 | 0.916 | 0.762 | 0.751 | 0.777 |
| Kendall's tau | 0.657 | 0.723 | 0.754 | 0.680 | 0.626 | 0.618 |
| Raw RMSE (kcal/mol) | 2.104 | 4.232 | 3.868 | 4.337 | 8.297 | 9.179 |
| Scaled RMSE (kcal/mol) | 1.578 | 1.613 | 1.186 | 3.500 | 4.316 | 3.992 |
|  | Nitrogenous Molecule Set | | | Heterocycle Set | | |
| $R^2$ | 0.615 | 0.485 | 0.795 | 0.604 | 0.528 | 0.552 |
| Kendall's tau | 0.420 | 0.412 | 0.592 | 0.652 | 0.622 | 0.646 |
| Raw RMSE (kcal/mol) | 2.384 | 2.416 | 1.690 | 4.314 | 7.584 | 8.722 |
| Scaled RMSE (kcal/mol) | 2.276 | 2.555 | 1.797 | 3.721 | 4.413 | 4.217 |
|  | Oxygenated & Nitrogenous Molecule Set | | | Polyfunctional Molecule Set | | |
| $R^2$ | 0.545 | 0.747 | 0.694 | 0.736 | 0.615 | 0.650 |
| Kendall's tau | 0.565 | 0.663 | 0.621 | 0.726 | 0.577 | 0.609 |
| Raw RMSE (kcal/mol) | 3.259 | 4.282 | 5.043 | 4.688 | 10.138 | 11.132 |
| Scaled RMSE (kcal/mol) | 2.991 | 2.794 | 2.484 | 3.597 | 5.335 | 4.804 |

Results for different test sets classified by functional groups provides deeper insights into the prediction abilities of the three computational models. For all three approaches, errors increased with the complexity of the functional groups. Solvation free energies of hydrocarbons, halocarbons, oxygen and nitrogen containing molecules were better reproduced than molecules with other functional groups, while amides and mixed polyfunctional groups resulted in the largest RMSEs.

Figure 15:
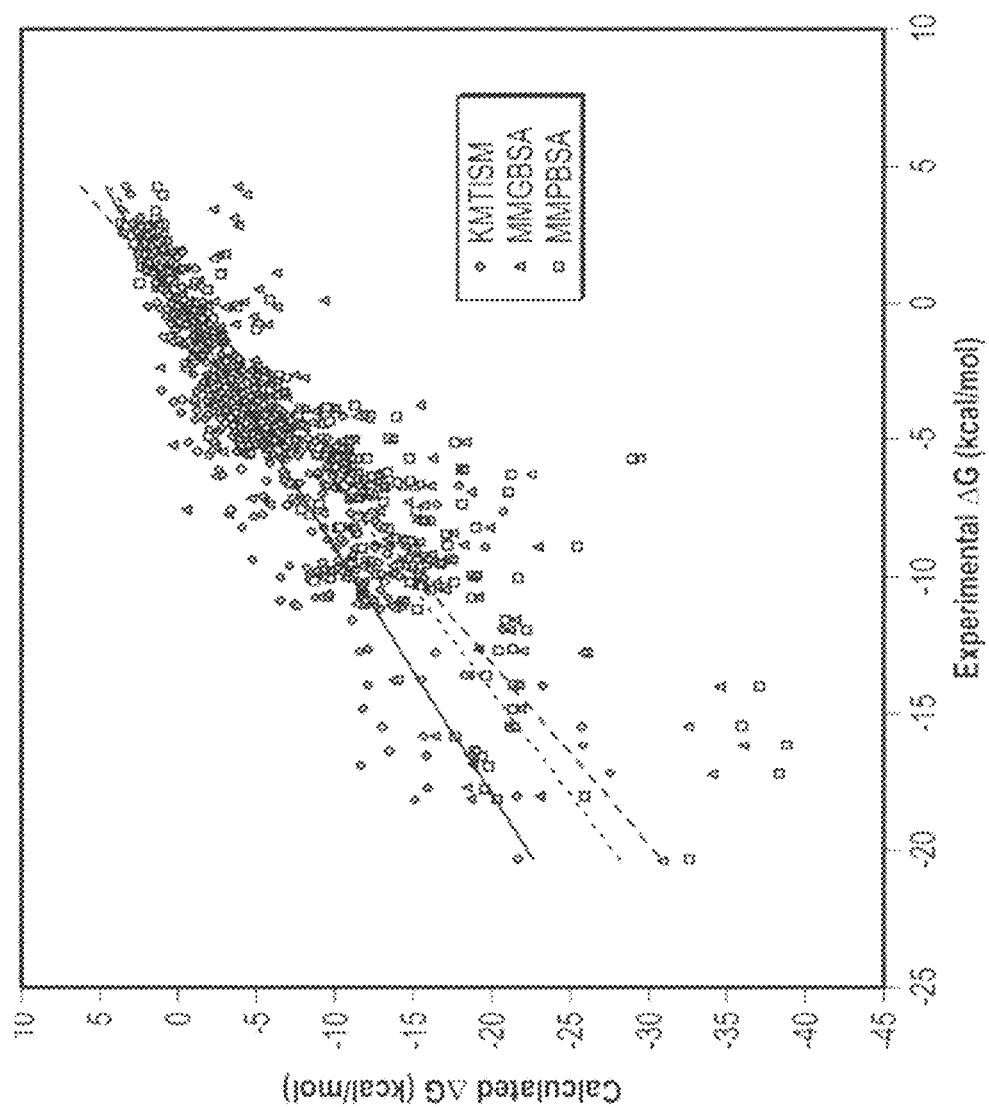
FIG. 15 is a graph showing KMTISM, MM-GBSA and MM-PBSA calculated vs. experimental solvation free energies (kcal/mol) for 372 neutral molecules (kcal/mol), according to some example embodiments.
Figure 16A:
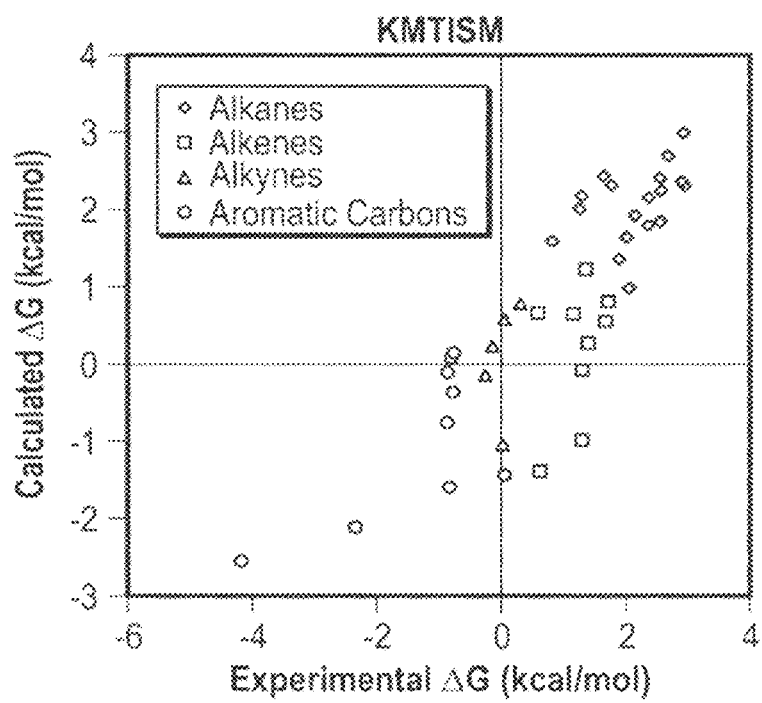
FIGS. 16A-16I graphically illustrate KMTISM's top three performing test sets according to RMSE (Root-Mean-Square Error), according to some example embodiments. KMTISM, MM-GBSA and MM-PBSA calculated solvation free energies (kcal/mol) vs. experimental data are shown.
Figure 16B:
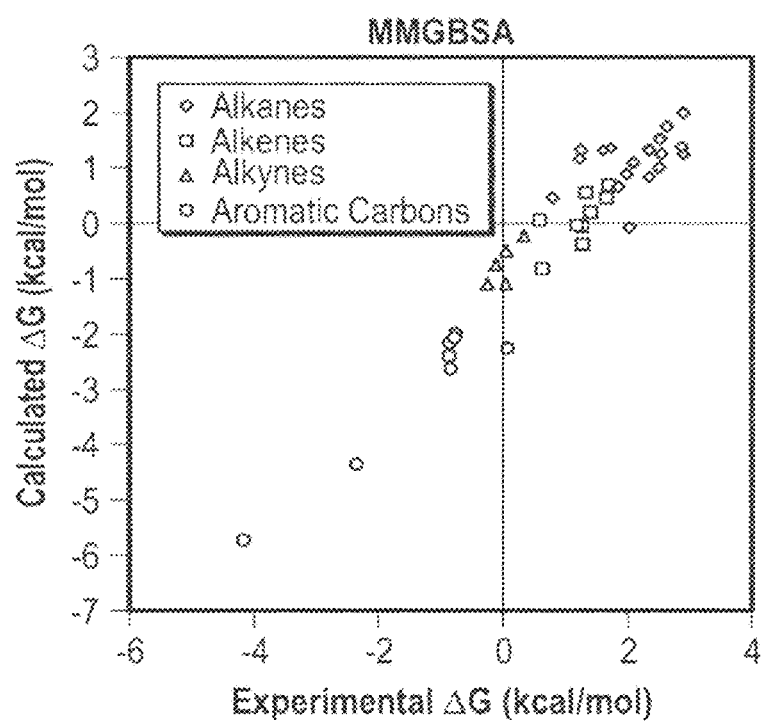
Figure 16C:
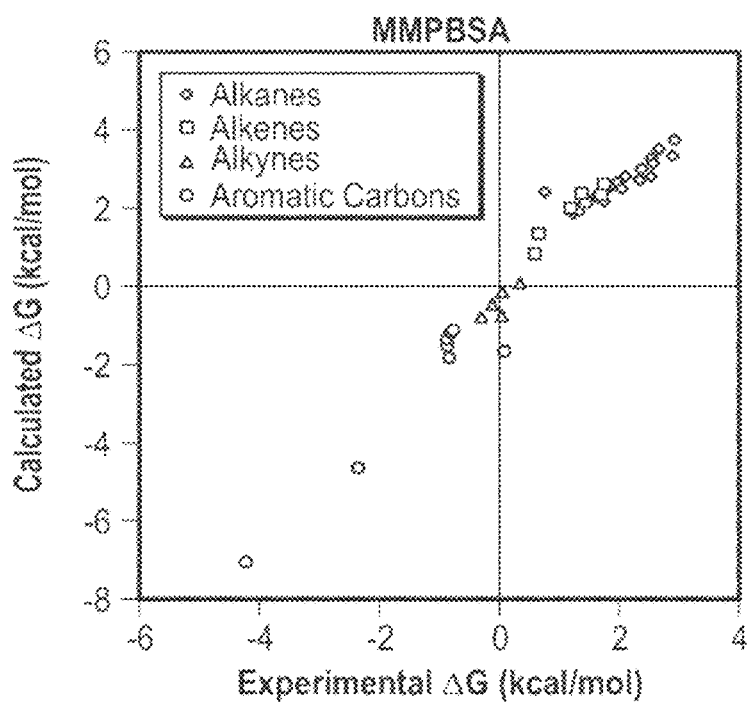
Figure 16D:
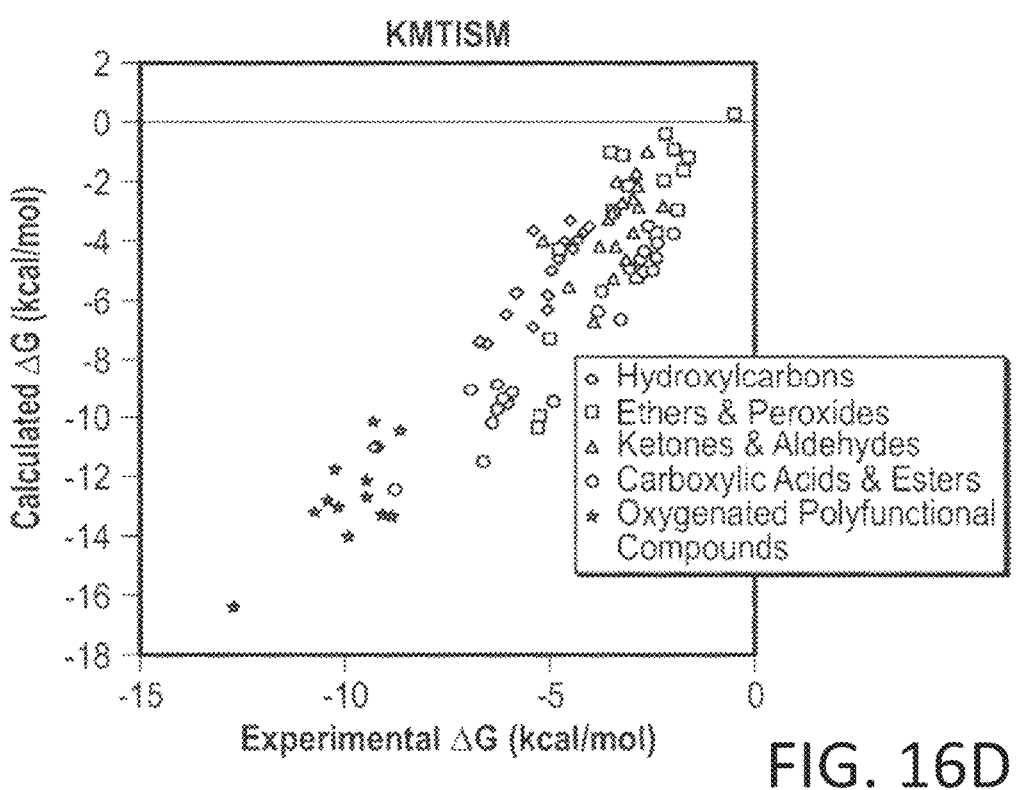
Figure 16E:
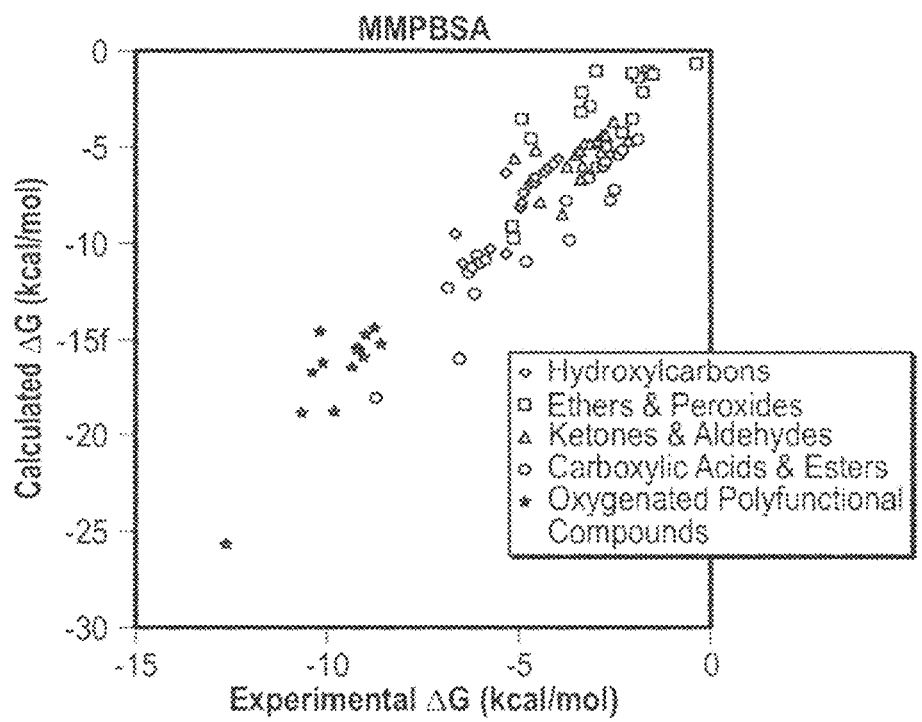
Figure 16F:
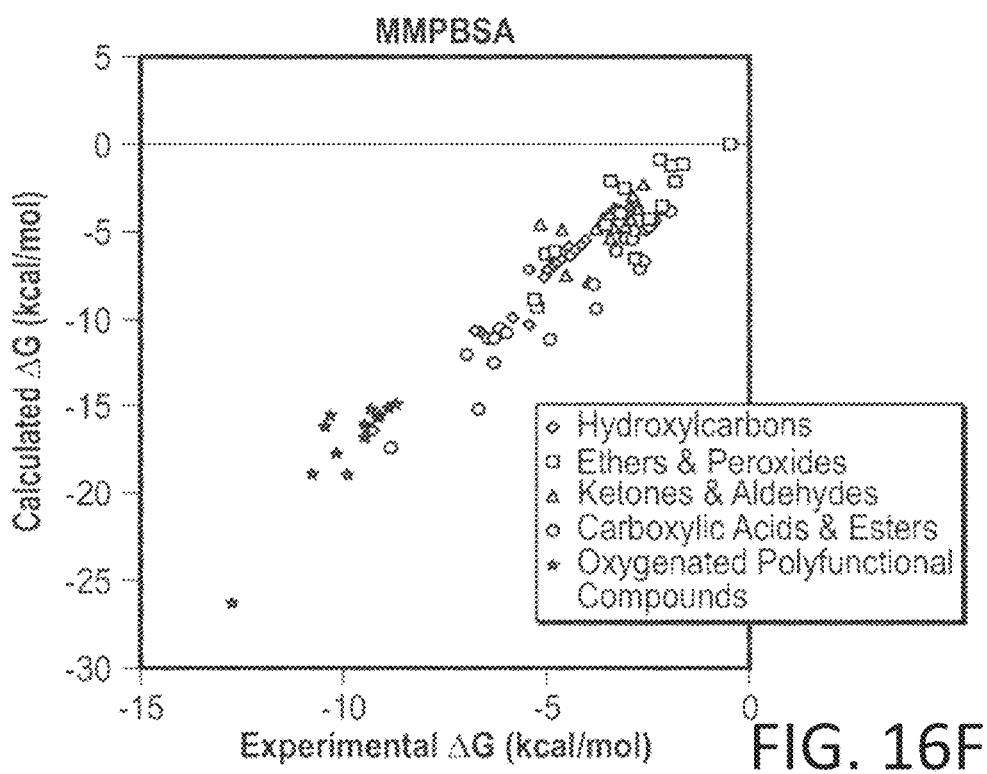
Figure 16G:
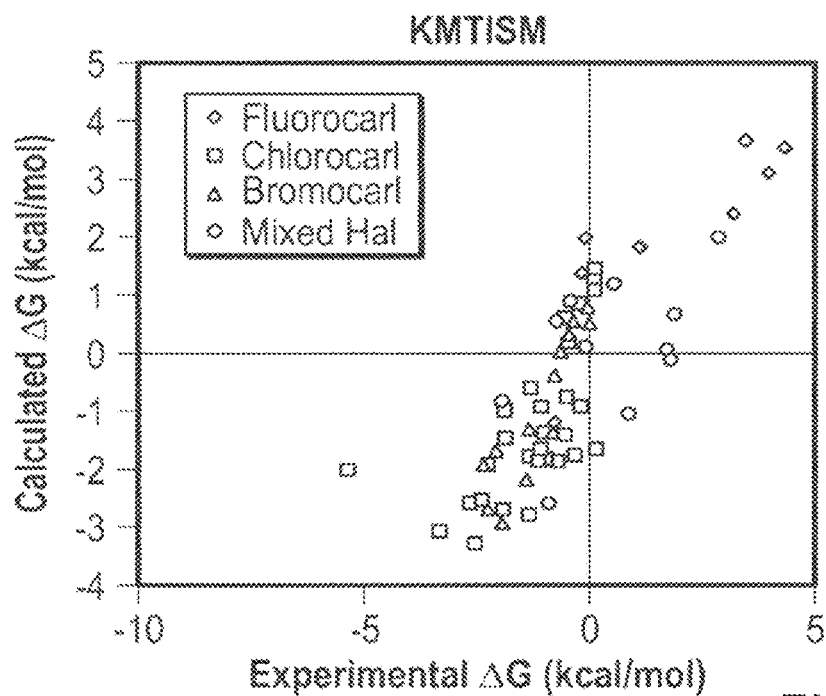
Figure 16H:
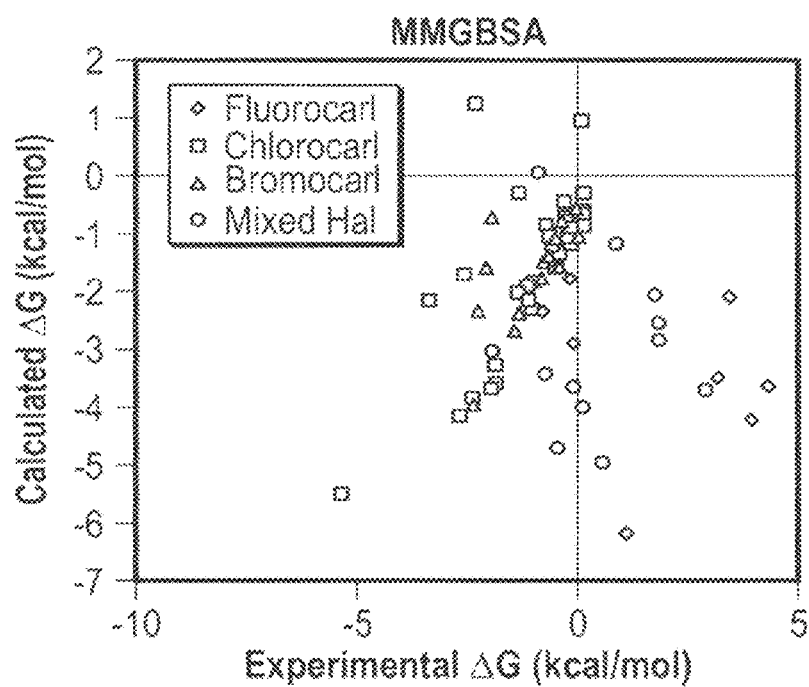
Figure 16I:
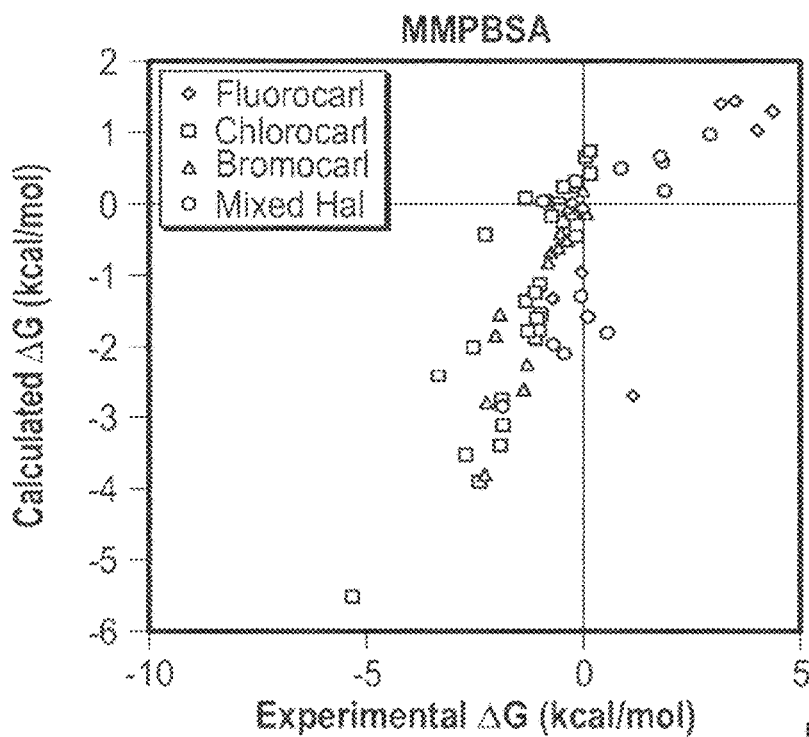
Figure 17A:
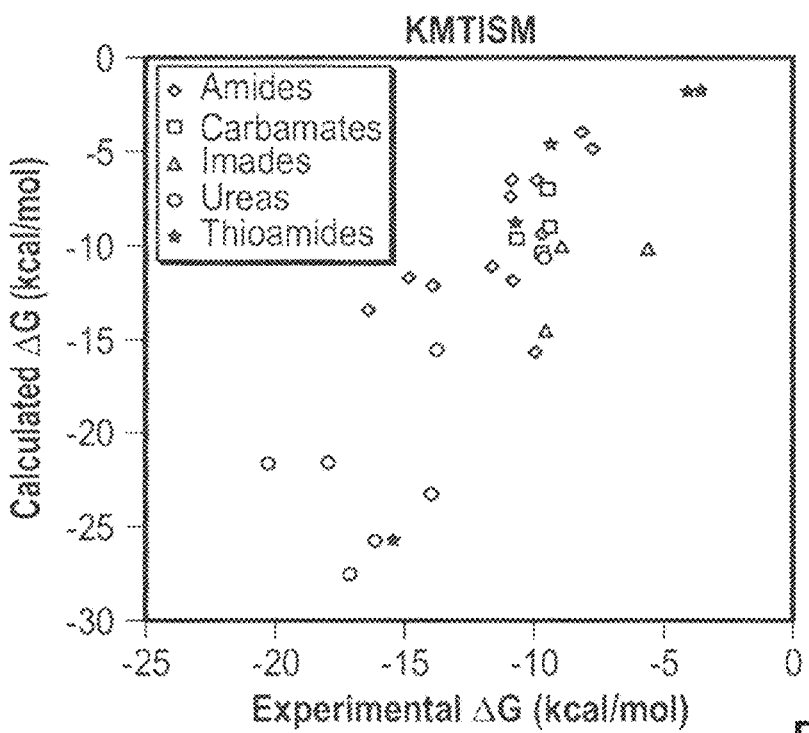
FIGS. 17A-17I graphically illustrate KMTISM's worst three performing test sets according to RMSE.
Figure 17B:
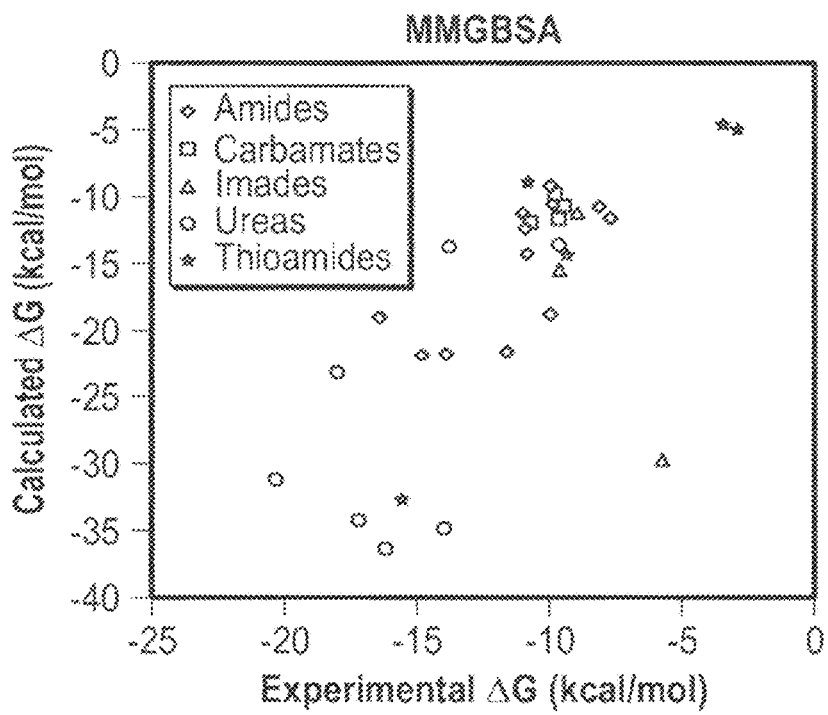
Figure 17C:
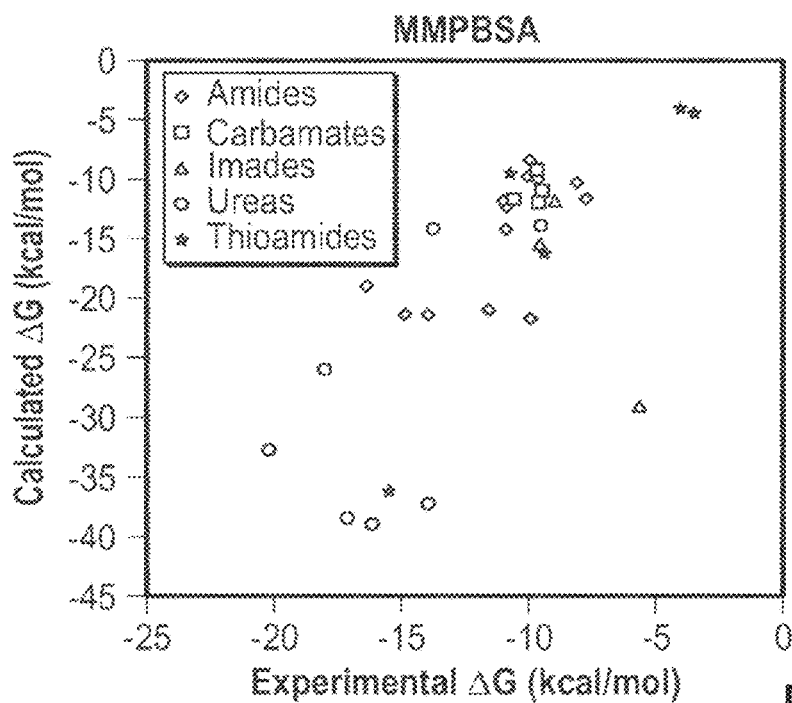
Figure 17D:
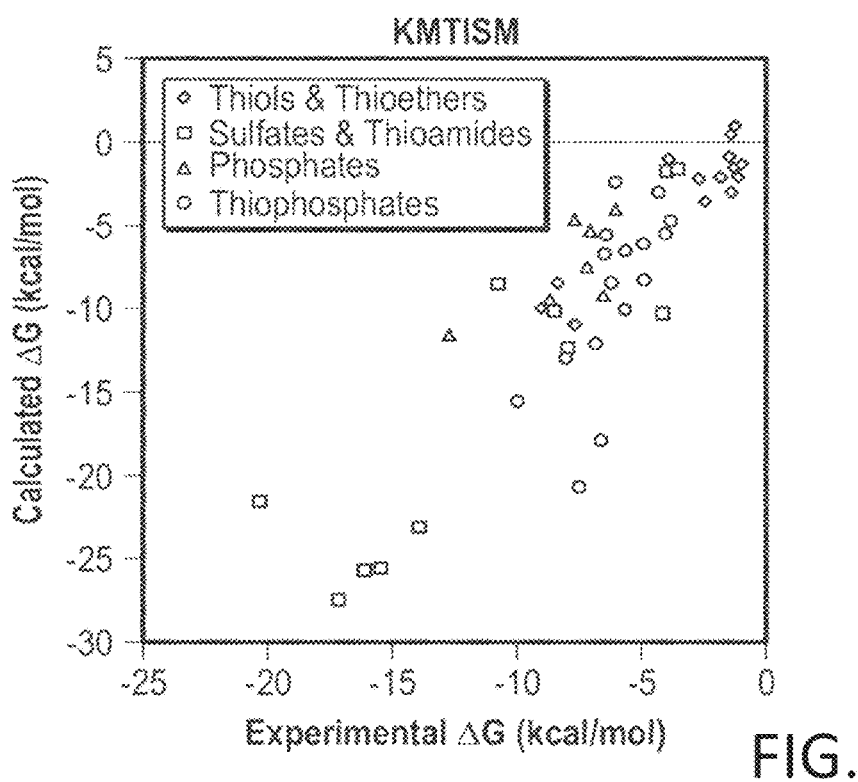
Figure 17E:
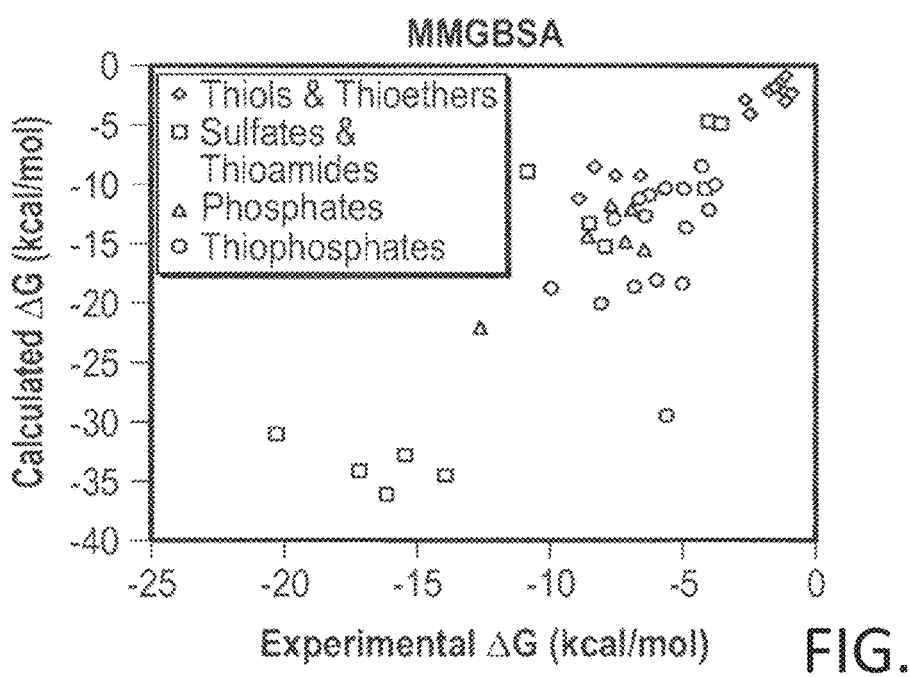
Figure 17F:
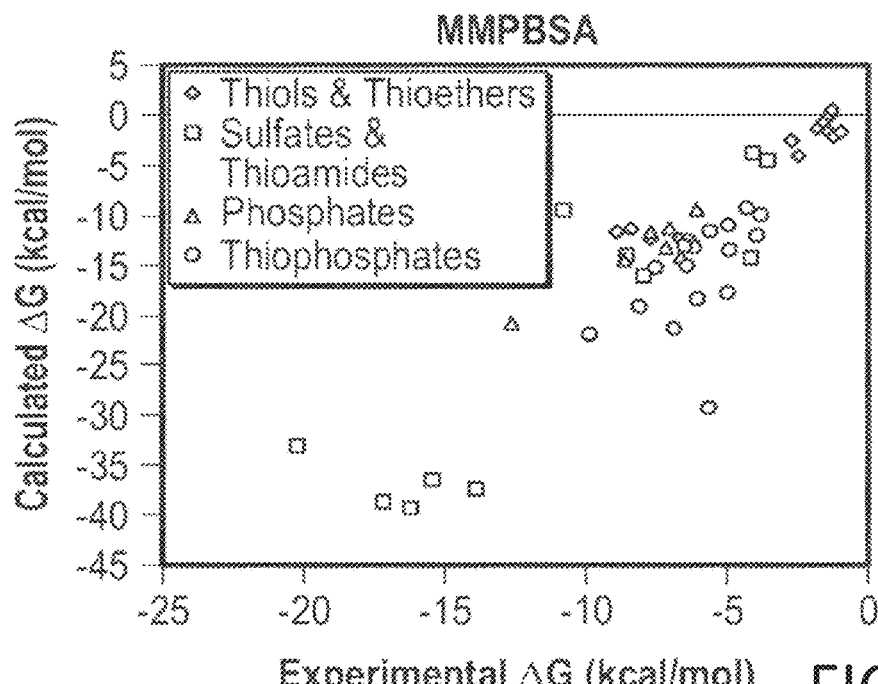
Figure 17G:
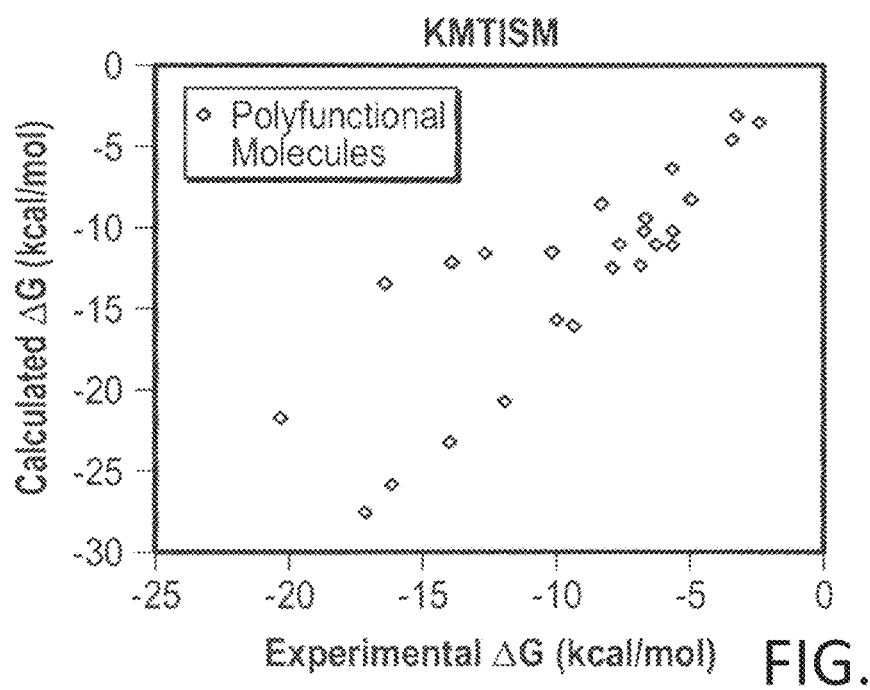
Figure 17H:
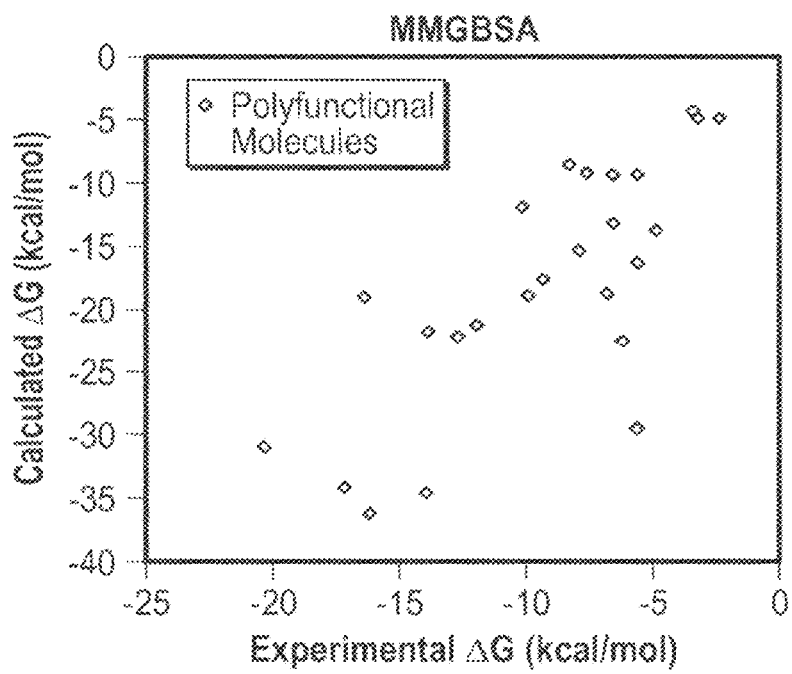
Figure 17I:
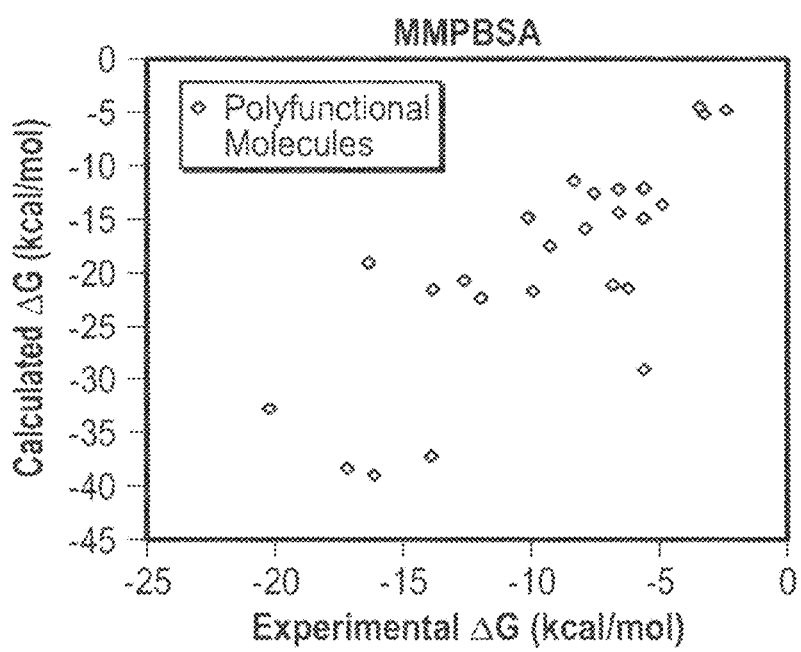

On the other hand, polar atom types in the KECSA energy function were classified according to their corresponding hydrophilic functional groups and were less affected by adjacent functional groups. Polar atom type-water radial probabilities were driven by a more fine grained atom pairwise set of interactions, thereby, improving the performance of the KECSA energy function for these groups. The oxygenated molecule set and halocarbon set were among the top 3 test sets based on KMTISM's performance according to RMSE. Against the oxygen containing molecule set, KMTISM gave a correlation coefficient comparable to MM-PBSA, while its RMSE was better than MM-GBSA. For the halocarbon set, KMTISM outperformed the MM-PB/GBSA methods according to the RMSE and correlation coefficients. Especially for fluorocarbons whose solvation free energies were much better reproduced by KMTISM compared to the MM-PB/GBSA methods. For the dataset of 8 fluorocarbons the RMSE for KMTISM was 1.1 kcal/mol compared to RMSE values as 5.8 kcal/mol for MM-GBSA and 2.2 kcal/mol for MM-PBSA. FIGS. 16A-16I show KMTISM's top three performing test sets according to RMSE. KMTISM, MM-GBSA and MM-PBSA calculated solvation free energies (kcal/mol) vs. experimental data are illustrated for hydrocarbon, oxygen containing and halocarbon test sets. FIG. 15 is a graph showing KMTISM, MM-GBSA and MM-PBSA calculated vs. experimental solvation free energies (kcal/mol) for 372 neutral molecules (kcal/mol).

The variety of atom types in different molecules with different chemical environments make the atom type classification process an inherent source of error for any statistical energy function. The use of atom types in classical potentials is also an issue, but it is typically mitigated by an explicit electrostatic model, which takes into account environmental effects. Collecting similar atom types into the same category can reduce the predictive ability of a statistical potential. For example, the sp$^3$ oxygen atom in ethers and peroxides were modeled using the same atom type within KECSA. This resulted in the solvation free energies for the two peroxides to be overestimated by KMTISM, i.e. the $\Delta G_{sol}$ for methylperoxide was −9.90 kcal/mol or −8.86 kcal/mol (scaled) vs. the experimental value of −5.28 kcal/mol and the $\Delta G_{sol}$ for ethylperoxide was −10.27 kcal/mol or −9.20 kcal/mol (scaled) vs. the experimental value of −5.32 kcal/mol. In comparison with the MM-GB/PBSA methods the $\Delta G_{sol}$ for methylperoxide was −9.89 kcal/mol or −6.51 kcal/mol (scaled) using MM-GBSA and −9.07 kcal/mol or −5.90 kcal/mol (scaled) using MM-PBSA; the $\Delta G_{sol}$ for ethylperoxide was −9.21 kcal/mol or −6.00 kcal/mol (scaled) using MM-GBSA and −8.59 kcal/mol or −5.59 kcal/mol (scaled) using MM-PBSA. Hence, none of the methods examined particularly did well modeling the solvation free energy of peroxides.

Figure 18A:
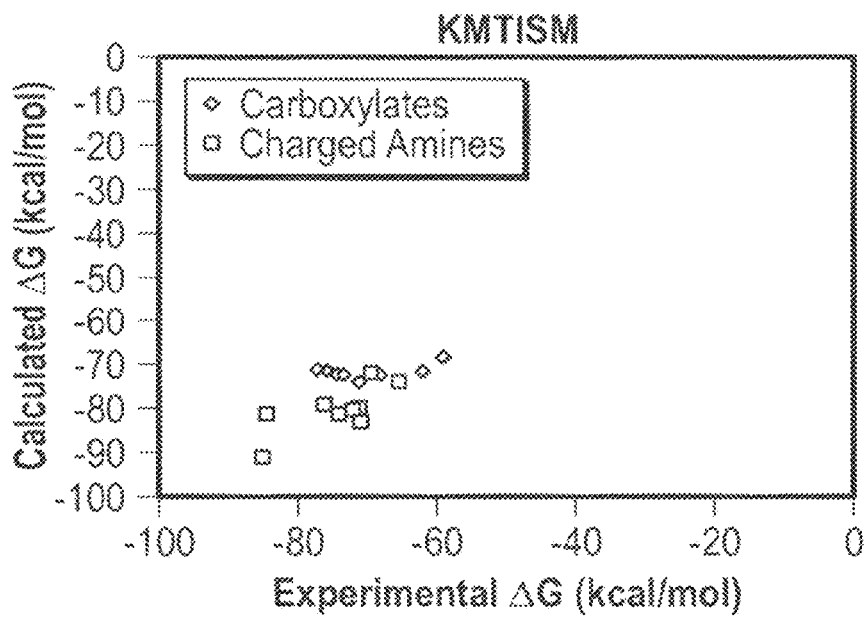
FIGS. 18A-18C graphically illustrates KMTISM, MM-GBSA and MM- PBSA calculated solvation free energies (kcal/mol) vs. experimental data for carboxylate and charged amine test sets, according to some example embodiments.
Figure 18B:
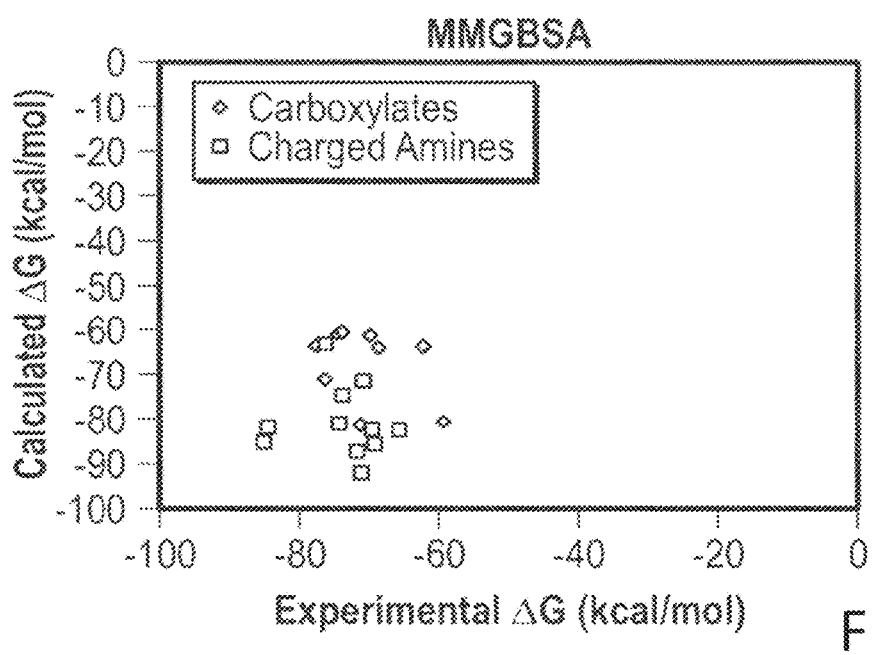
Figure 18C:
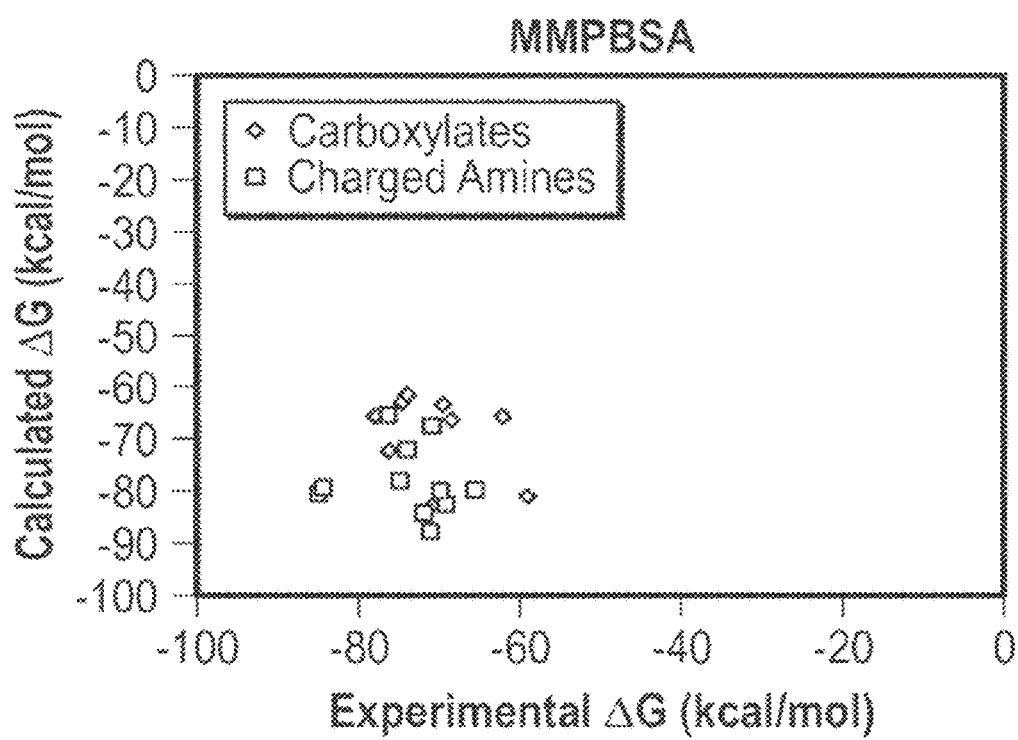

As the structural complexity of a molecule increased so did the computed RMSE. Possible long-range polar interactions add additional difficulty to accurate solvation free energy calculations using the methods described herein. The largest errors were found in the amide set, organosulfur and organophosphorus set and polyfunctional molecule set for all three methods. With lower errors for most individual polar functional groups based on the analysis of the monofunctional test set results, KMTISM had less cumulative error against these three test sets when compared with the MM-GB/PBSA methods for both the raw RMSE and scaled RMSE values (See Table 5). FIG. 17A-17I shows KMTISM's worst three performing test sets according to RMSE, including amide, organosulfur and organophosphorus, and polyfunctional test sets. FIGS. 18A-18C graphically illustrate KMTISM, MM-GBSA and MM-PBSA calculated solvation free energies (kcal/mol) vs. experimental data for carboxylate and charged amine test sets.

This result suggests that KMTISM has an advantage over the MM-GB/PBSA methods for the prediction of the solvation free energy of polyfunctional molecules. This advantage will have a significant effect on the ability of this model to predict, for example, protein-ligand binding affinities, where the solvation free energy of the ligand can have a significant impact on binding affinity prediction.

Although the magnitude of the errors in the solvation free energies for the ion test set were relatively poor for all three methods, KMTISM showed better correlations and RMSE than the other two implicit water models, especially for the charged amine test set (see Table 3). While the error magnitude was large for all methods the percentage error is comparable to the neutral set. The carboxylate functional group, which is conjugated, lowered the accuracy of KMTISM's calculation, while charged amines, on the other hand, whose electron densities are more localized, were better reproduced by the KMTISM method.

TABLE 6

Performance of KMTISM, MM-GBSA and MM-PBSA for the prediction of the solvation free energies of ions.

| | Ion Set | | |
|---|---|---|---|
| | KMTISM | MM-GBSA | MM-PBSA |
| $R^2$ | 0.351 | 0.000 | 0.003 |
| Kendall's tau | 0.258 | −0.057 | −0.067 |
| RMSE (kcal/mol) | 5.777 | 11.736 | 10.481 |
| | Carboxylate Set | | |
| | KMTISM | MM-GBSA | MM-PBSA |
| $R^2$ | 0.239 | 0.161 | 0.166 |
| Kendal's tau | −0.090 | −0.180 | −0.180 |
| RMSE (kcal/mol) | 5.337 | 11.918 | 11.252 |
| | Charged Amine Set | | |
| | KMTISM | MM-GBSA | MM-PBSA |
| $R^2$ | 0.557 | 0.008 | 0.009 |
| Kendall's tau | 0.491 | −0.127 | −0.127 |
| RMSE (kcal/mol) | 6.149 | 11.569 | 9.727 |

Comparison with SMX Results

The polarizable continuum solvent model allows QM based SCF energy calculations to experience the effect of solvation. Overall, this model class has had limited application in the study of macromolecular systems due to its higher computational expense, but are routinely used to understand the effect of solvation on small molecules. A thorough analysis of KMTISM against QM based solvation models was not the focus of the present research, but a general comparison helps put the present work in perspective relative to more advanced models. Cramer and Truhlar's Solvation Model (SMX) series represents a well-regarded solvation model utilizing a PCM-like approach.

As one of the top ranked solvation energy calculation methods, Cramer and Truhlar's Solvation Model (SMX) series has been developed over decades. Their most up-to-date model reported mean absolute errors (MAE) for solvation free energy ($\Delta G_{sol}$) prediction ranging from 0.57 to 0.84 kcal/mol using different QM methods against 274 neutral molecules and calculated $\Delta G_{sol}$ MAEs ranged from 2.7 to 3.8 kcal/mol against 112 ions. Against a similar small molecule and ion test set, KMTISM reproduced a calculated $\Delta G_{sol}$ MAE of 1.79 kcal/mol against the 372 selected neutral molecules and a MAE of 5.06 kcal/mol against the selected 21 ions. Even though the data sets examined were different, the trend is clear that the latest SM models is more accurate than KMTISM (and MM-GBSA and MM-PBSA) by ~1 kcal/mol for both the neutral molecules and the ions as measured by MAE. Nonetheless, the performance of our first generation KMTISM model is impressive and future versions of this model should yield even better accuracy.

MM-GBSA and MM-PBSA are two broadly used implicit solvation models. KMTISM, using a new sampling method (MT method), combined with a statistical energy function (KECSA), is found to have a comparable or a better ability to predict the solvation free energy for several test sets selected from the Minnesota Solvation Database. Though all of these methods perform worse than the most recent SMX model reported by Cramer and Truhlar. It is important to appreciate that without using the approximation that the free energy of solvation is a collection of linearly combined free energies, as is employed in many traditional continuum solvent models, KMTISM uses computed energies to directly determine free energies. Hence, the Helmholtz free energy is calculated by the construction of the relevant partition functions. These partition functions are efficiently assembled using a new sampling method, the MT method, which is able to rapidly estimate free energy, enthalpy, as well as entropy changes. Drawbacks of the KMTISM model lie in its use of a statistical energy function, whose parameterization can have weak spots for atom types with high polarizabilites and uncommon atom types whose lack of available experimental data can pose issues. Future work includes (1) a detailed study of enthalpy changes and entropy changes using the MT method; (2) improving the statistical energy terms by data collection from MD simulations of atom types with high polarizability and uncommon atom types in structural databases, and (3) replacing the statistical energy function with different force field based energy functions and combine them with the MT sampling method in order to affect the rapid evaluation of thermodynamic quantities.

Example 5

Tables 7 and 8 show the experimental and computed solvation free energies of the neutral molecules (Table 7) and charge ions (Table 8) that were studies using the methodology disclosed above.

The method detailed above may also be used in a system that comprises a computational device. The system uses a computational device such as a computer to estimate a pose of a ligand in a receptor that comprises identifying all possible atom pairs of protein-ligand complexes in a given configuration space for a system that comprises proteins. It then creates a first database and a second database; where the first database comprises associated pairwise distant dependent energies and where the second database comprises all probabilities that include how the atom pairs can combine. The first database is then combined with the second database using statistical mechanics to accurately estimate binding free energies as well as the pose of the ligand in the receptor. A protein-ligand complex is then used for further study depending upon the data obtained for the aforementioned estimations.

The further study can include ranking the interactions so as to enable one to choose a group of protein-ligand complexes for further experimentation, analysis or product development, for use in choosing a particular protein-ligand for developing a medical device, an analytical device such as a fluidics device, and the like. The further study can also include choosing a protein-ligand for the further complexation studies—where the protein-ligand is further complexed with another molecule.

TABLE 7

KMTISM, MM-GBSA and MM-PBSA calculated solvation free energy (in kcal/mol) results against the test set with 372 neutral compounds.

| Compound ID | Exp. ΔGsolv | KMTISM Raw Result | KMTISM Scaled Result | MM-GBSA Raw Result | MM-GBSA Scaled Result | MM-PBSA Raw Result | MM-PBSA Scaled Result | Solute Name | Formula |
|---|---|---|---|---|---|---|---|---|---|
| 0044met | −5.11 | −5.8 | −5.17 | −8.2 | −5.24 | −7.35 | −4.76 | methanol | H4C1O1 |
| 0045eth | −5.01 | −4.96 | −4.41 | −7.45 | −4.67 | −6.83 | −4.42 | ethanol | H6C2O1 |
| 0046eth | −9.3 | −11 | −9.85 | −15.6 | −10.85 | −16.12 | −10.57 | 1,2-ethanediol | H6C2O2 |
| 0047pro | −4.83 | −4.6 | −4.08 | −6.97 | −4.3 | −6.17 | −4.18 | 1-propanol | H8C3O1 |
| 0048pro | −1.76 | −4.2 | −3.72 | −7.01 | −4.34 | −6.23 | −4.02 | isopropanol | H8C3O1 |
| 0049but | −4.72 | −3.98 | −3.52 | −6.71 | −4.11 | −6.23 | −4.03 | 1-butanol | H10C4O1 |
| 0050met | −4.51 | −3.29 | −2.9 | −6.34 | −3.83 | −5.62 | −3.62 | t-butanol | H10C4O1 |
| 0051cyc | −5.49 | −3.62 | −3.19 | −6.5 | −3.95 | −6.87 | −4.45 | cyclopentanol | H10C5O1 |
| 0052pen | −4.47 | −4.25 | −3.77 | −6.43 | −3.9 | −6.04 | −3.9 | 1-pentanol | H12C5O1 |
| 0053phe | −6.62 | −7.41 | −6.62 | −11.11 | −7.45 | −10.47 | −6.83 | phenol | H6C6O1 |
| 0054hex | −4.36 | −3.93 | −3.48 | −6.18 | −3.71 | −5.79 | −3.73 | 1-hexanol | H14C6O1 |
| 0055ocr | −5.87 | −5.74 | −5.11 | −10.38 | −6.9 | −9.57 | −6.24 | o-cresol | H8C7O1 |
| 0056mcr | −5.49 | −6.85 | −6.11 | −10.67 | −7.11 | −9.98 | −6.51 | m-cresol | H8C7O1 |
| 0057pcr | −6.14 | −6.43 | −5.73 | −10.78 | −7.19 | −10.17 | −6.64 | p-cresol | H8C7O1 |
| 0058hep | −4.24 | −3.63 | −3.21 | −5.96 | −3.54 | −5.5 | −3.54 | 1-heptanol | H16C7O1 |
| 0145pro | −5.08 | −6.25 | −5.57 | −8 | −5.09 | −7.23 | −4.69 | allylalcohol | H6C3O1 |
| 0146met | −6.77 | −7.35 | −6.56 | −9.62 | −6.31 | −10.43 | −6.81 | 2-methoxyethanol | H8C3O2 |
| 0236oct | −4.09 | −3.49 | −3.07 | −5.71 | −3.35 | −5.25 | −3.38 | 1-octanol | H18C8O1 |
| 0070eth | −3.5 | −5.19 | −4.61 | −6.76 | −4.15 | −4.99 | −3.2 | acetaldehyde | H4C2O1 |
| 0071proa | −3.44 | −4.09 | −3.62 | −6.05 | −3.61 | −4.44 | −2.84 | propanal | H6C3O1 |
| 0072but | −3.18 | −4.56 | −4.05 | −6 | −3.57 | −4.42 | −2.83 | butanal | H8C4O1 |
| 0073pen | −3.03 | −3.63 | −3.2 | −5.51 | −3.2 | −3.98 | −2.53 | pentanal | H10C5O1 |
| 0074ben | −4.02 | −6.61 | −5.9 | −8.56 | −5.52 | −7.55 | −4.9 | benzaldehyde | H6C7O1 |
| 0237oct | −2.29 | −2.72 | −2.39 | −4.85 | −2.7 | −3.28 | −2.07 | octanal | H16C8O1 |
| 0150mhy | −9.51 | −12.67 | −11.37 | −16.65 | −11.65 | −15.84 | −10.39 | m-hydroxybenzaldehyde | H6C7O2 |
| 0151phy | −10.48 | −12.77 | −11.45 | −16.85 | −11.8 | −16 | −10.49 | p-hydroxybenzaldehyde | H6C7O2 |
| 0233ethb | −9.71 | −10.71 | −9.59 | −10.89 | −7.28 | −9.93 | −6.47 | acetamide | H5C2N1O1 |
| 0234ENmb | −10 | −6.4 | −5.7 | −9.08 | −5.9 | −8.37 | −5.44 | E-N-methylacetamide | H7C3N1O1 |
| 0235ZNmb | −10 | −6.37 | −5.68 | −10.49 | −6.98 | −9.48 | −6.17 | Z-N-methylacetamide | H7C3N1O1 |
| n008 | −10.9 | −11.69 | −10.48 | −12.24 | −8.3 | −12.16 | −7.95 | benzamide | H7C7N1O1 |
| test0006 | −9.76 | −9.15 | −8.19 | −9.42 | −6.17 | −9.29 | −6.05 | N,N,4-trimethylbenzamide | H13C10N1O1 |

TABLE 7-continued

KMTISM, MM-GBSA and MM-PBSA calculated solvation free energy (in kcal/mol) results against the test set with 372 neutral compounds.

| Compound ID | Exp. ΔGsolv | KMTISM Raw Result | KMTISM Scaled Result | MM-GBSA Raw Result | MM-GBSA Scaled Result | MM-PBSA Raw Result | MM-PBSA Scaled Result | Solute Name | Formula |
|---|---|---|---|---|---|---|---|---|---|
| test3001 | −14.83 | −11.62 | −10.42 | −21.72 | −15.49 | −21.24 | −13.96 | paracetamol | H9C8N1O2 |
| test3004 | −11.61 | −11 | −9.86 | −21.46 | −15.29 | −20.84 | −13.7 | N-(2-hydroxyphenyl) acetamide | H9C8N1O2 |
| test3002 | −13.93 | −12.01 | −10.77 | −21.56 | −15.37 | −21.32 | −14.02 | N-(3-hydroxyphenyl) acetamide | H9C8N1O2 |
| test0005 | −11.01 | −7.27 | −6.49 | −11.19 | −7.51 | −11.71 | −7.66 | N,N-dimethyl-p-methoxybenzamide | H13C10N1O2 |
| test3005 | −10.91 | −6.35 | −5.66 | −14.26 | −9.83 | −14.15 | −9.27 | phenacetin | H13C10N1O2 |
| 0103eth | −4.5 | −5.37 | −4.78 | −5.65 | −3.31 | −3.94 | −2.51 | ethylamine | H7C2N1 |
| 0104dim | −4.29 | −1.01 | −0.84 | −3.86 | −1.95 | −3.75 | −2.38 | dimethylamine | H7C2N1 |
| 0105aze | −5.56 | −1.9 | −1.64 | −4.14 | −2.16 | −4.48 | −2.87 | azetidine | H7C3N1 |
| 0106pro | −4.39 | −5.25 | −4.67 | −5.25 | −3 | −3.67 | −2.33 | propylamine | H9C3N1 |
| 0107tri | −3.23 | 1.14 | 1.1 | −1.42 | −0.1 | −3.43 | −2.17 | trimethylamine | H9C3N1 |
| 0108pyr | −5.48 | −1.16 | −0.97 | −2.65 | −1.03 | −4.26 | −2.72 | pyrrolidine | H9C4N1 |
| 0109pip | −7.4 | −6.87 | −6.13 | −5.62 | −3.28 | −8.76 | −5.7 | piperazine | H10C4N2 |
| 0110but | −4.29 | −4.7 | −4.17 | −4.88 | −2.73 | −3.43 | −2.17 | butylamine | H11C4N1 |
| 0111die | −4.07 | −0.14 | −0.06 | −1.89 | −0.45 | −2.58 | −1.61 | diethylamine | H11C4N1 |
| 0112Nme | −7.77 | −5.28 | −4.69 | −3.01 | −1.3 | −8.25 | −5.36 | N-methylpiperazine | H12C5N2 |
| 0113pen | −4.1 | −4.51 | −4 | −4.72 | −2.6 | −3.22 | −2.03 | pentylamine | H13C5N1 |
| 0114NNd | −7.58 | −3.27 | −2.88 | −0.39 | 0.68 | −7.73 | −5.02 | N,N'-dimethylpierazine | H14C6N2 |
| 0115dip | −3.66 | 0.34 | 0.38 | −0.96 | 0.25 | −1.71 | −1.03 | dipropylamine | H15C6N1 |
| 0118ani | −5.49 | −7.7 | −6.87 | −7.88 | −5 | −6.97 | −4.52 | aniline | H7C6N1 |
| 0225pipa | −5.11 | −0.54 | −0.41 | −2.1 | −0.61 | −3.75 | −2.38 | piperidine | H11C5N1 |
| 0228met | −4.56 | −6.22 | −5.54 | −6.7 | −4.1 | −4.43 | −2.83 | methylamine | H5C1N1 |
| n009 | −5.56 | −5.88 | −5.23 | −7.31 | −4.56 | −6.56 | −4.24 | 2-methylaniline | H9C7N1 |
| n010 | −5.67 | −6.78 | −6.05 | −7.58 | −4.77 | −6.64 | −4.3 | 3-methylaniline | H9C7N1 |
| n011 | −5.55 | −6.78 | −6.05 | −7.46 | −4.68 | −6.65 | −4.3 | 4-methylaniline | H9C7N1 |
| n013 | −4.62 | −1.91 | −1.65 | −5.36 | −3.09 | −5.6 | −3.61 | N-ethylaniline | H11C8N1 |
| n014 | −3.58 | −0.14 | −0.06 | −4.41 | −2.36 | −5.86 | −3.78 | N,N-dimethylaniline | H11C8N1 |
| n015 | −9.92 | −13.66 | −12.25 | −13.25 | −9.07 | −12.47 | −8.16 | 3,aminoaniline | H8C6N2 |
| n016 | −9.72 | −12.04 | −10.8 | −11.1 | −7.44 | −9.82 | −6.4 | 1,2-ethanediamine | H8C2N2 |
| 0147met | −6.55 | −7.64 | −6.82 | −7.33 | −4.58 | −7.06 | −4.57 | 2-methoxyethanamine | H9C3N1O1 |
| 0149mor | −7.17 | −5.3 | −4.71 | −4.5 | −2.43 | −7.22 | −4.68 | morpholine | H9C4N1O1 |
| 0227Nme | −6.34 | −2.72 | −2.38 | −2.14 | −0.65 | −6.72 | −4.35 | N-methylmorpholine | H11C5N1O1 |
| test1059 | −7.4 | −16.38 | −14.72 | −15.54 | −10.81 | −18.03 | −11.84 | 1-amino-4-anilinoanthraquinone | H14C20N2O2 |
| test1060 | −8.9 | −19.45 | −17.49 | −22.8 | −16.31 | −25.4 | −16.72 | 1,4,5,8-tetraminoanthraquinone | H12C14N4O2 |
| test1061 | −8 | −15.57 | −13.98 | −15.17 | −10.53 | −15.98 | −10.48 | 1-amino-anthraquinone | H9C14N1O2 |
| test1015 | −9.5 | −9.06 | −8.1 | −10.37 | −6.89 | −11.08 | −7.24 | carbaryl | H11C12N1O2 |
| test1016 | −9.6 | −6.89 | −6.15 | −11.51 | −7.75 | −11.81 | −7.72 | carbofuran | H15C12N1O3 |
| test1037 | −10.7 | −9.45 | −8.46 | −11.74 | −7.93 | −11.57 | −7.56 | methomyl | H10C5N2O2S1 |
| test1008 | −9.8 | −10.28 | −9.21 | −9.53 | −6.25 | −9.08 | −5.91 | aldicarb | H14C7N2O2S1 |
| 0086eth | −6.7 | −11.44 | −10.25 | −15.99 | −11.14 | −15 | −9.83 | aceticacid | H4C2O2 |
| 0087pro | −6.47 | −10.12 | −9.06 | −11.57 | −7.79 | −10.83 | −7.07 | propanoicacid | H6C3O2 |
| 0088but | −6.36 | −9.72 | −8.7 | −11.26 | −7.56 | −10.75 | −7.02 | butanoicacid | H8C4O2 |
| 0089pen | −6.16 | −9.46 | −8.47 | −11.02 | −7.38 | −10.42 | −6.8 | pentanoicacid | H10C5O2 |
| 0090hex | −6.21 | −9.37 | −8.39 | −10.65 | −7.09 | −10.19 | −6.65 | hexanoicacid | H12C6O2 |
| test2017 | −7 | −9.02 | −8.07 | −12.32 | −8.36 | −11.75 | −7.68 | ibuprofen | H18C13O2 |
| test2001 | −9.94 | −13.96 | −12.53 | −18.92 | −13.37 | −18.67 | −12.26 | acetylsalicylicacid | H8C9O4 |
| test3007 | −10.32 | −11.71 | −10.5 | −14.69 | −10.17 | −15.34 | −10.06 | 2-methoxybenzoicacid | H8C8O3 |
| test3014 | −9.15 | −13.25 | −11.89 | −14.72 | −10.18 | −15.34 | −10.06 | 4-methoxybenzoicacid | H8C8O3 |
| test3015 | −8.93 | −13.33 | −11.96 | −14.43 | −9.97 | −14.85 | −9.74 | 3-methoxybenzoicacid | H8C8O3 |
| test2021 | −10.21 | −12.96 | −11.62 | −16.33 | −11.4 | −17.54 | −11.52 | naproxen | H14C14O3 |
| test3003 | −12.75 | −16.37 | −14.7 | −25.75 | −18.55 | −26.05 | −17.15 | fenbufen | H14C16O3 |
| test2019 | −10.78 | −13.16 | −11.8 | −19 | −13.43 | −18.71 | −12.29 | ketoprofen | H14C16O3 |
| 0093met | −3.32 | −6.61 | −5.89 | −6.66 | −4.07 | −5.79 | −3.74 | methylacetate | H6C3O2 |
| 0094met | −2.93 | −5.07 | −4.51 | −6.06 | −3.62 | −5.13 | −3.29 | methylpropanoate | H8C4O2 |
| 0095eth | −3.1 | −4.88 | −4.33 | −6.1 | −3.65 | −5.13 | −3.29 | ethylacetate | H8C4O2 |
| 0096met | −2.83 | −4.98 | −4.42 | −5.68 | −3.33 | −4.79 | −3.07 | methylbutanoate | H10C5O2 |
| 0097pro | −2.86 | −4.55 | −4.03 | −5.77 | −3.4 | −4.68 | −3 | propylacetate | H10C5O2 |
| 0098met | −2.57 | −4.94 | −4.39 | −5.41 | −3.13 | −4.59 | −2.94 | methylpentanoate | H12C6O2 |
| 0099but | −2.55 | −4.53 | −4.02 | −5.43 | −3.14 | −4.38 | −2.8 | butylacetate | H12C6O2 |
| 0100met | −2.49 | −4.54 | −4.02 | −5.2 | −2.96 | −4.2 | −2.68 | methylhexanoate | H14C7O2 |
| 0101pen | −2.45 | −4 | −3.54 | −5.2 | −2.96 | −4.13 | −2.63 | pentylacetate | H14C7O2 |
| 0238met | −2.04 | −3.72 | −3.28 | −4.74 | −2.62 | −3.69 | −2.34 | methyloctanoate | H18C9O2 |
| 0240met | −3.91 | −6.34 | −5.65 | −7.83 | −4.96 | −7.71 | −5.01 | methylbenzoate | H8C8O2 |
| test0001 | −8.84 | −12.38 | −11.1 | −18.14 | −12.78 | −17.12 | −11.24 | glyceroltriacetate | H14C9O6 |
| test0008 | −4.97 | −9.45 | −8.45 | −11.01 | −7.37 | −10.87 | −7.1 | 1,1-diacetoxyethane | H10C6O4 |
| test0011 | −6 | −9.11 | −8.15 | −10.91 | −7.3 | −10.45 | −6.82 | diethylpropanedioate | H12C7O4 |
| test0013 | −6.34 | −8.81 | −7.88 | −12.65 | −8.61 | −12.26 | −8.02 | ethyleneglycoldiacetate | H10C6O4 |
| test2003 | −8.72 | −10.4 | −9.32 | −15.29 | −10.62 | −14.73 | −9.66 | butylparaben | H14C11O3 |

TABLE 7-continued

KMTISM, MM-GBSA and MM-PBSA calculated solvation free energy (in kcal/mol) results against the test set with 372 neutral compounds.

| Compound ID | Exp. ΔGsolv | KMTISM Raw Result | KMTISM Scaled Result | MM-GBSA Raw Result | MM-GBSA Scaled Result | MM-PBSA Raw Result | MM-PBSA Scaled Result | Solute Name | Formula |
|---|---|---|---|---|---|---|---|---|---|
| test2011 | −9.2 | −10.91 | −9.77 | −15.96 | −11.12 | −15.49 | −10.16 | ethylparaben | H10C9O3 |
| test2020 | −9.51 | −12.1 | −10.85 | −16.56 | −11.58 | −16.51 | −10.83 | methylparaben | H8C8O3 |
| test2026 | −9.37 | −10.11 | −9.05 | −15.53 | −10.8 | −14.97 | −9.81 | propylparaben | H12C10O3 |
| 0060dim | −1.92 | −2.92 | −2.56 | −2.24 | −0.72 | −1.85 | −1.12 | dimethylether | H6C2O1 |
| 0061tet | −3.47 | −2.92 | −2.56 | −2.25 | −0.73 | −1.85 | −1.12 | tetrahydrofuran | H8C4O1 |
| 0062dio | −5.05 | −7.22 | −6.44 | −3.64 | −1.78 | −6.01 | −3.88 | 1,4-dioxane | H8C4O2 |
| 0063die | −1.76 | −1.52 | −1.3 | −1.27 | 0.01 | −0.91 | −0.5 | diethylether | H10C4O1 |
| 0064met | −1.66 | −1.1 | −0.92 | −1.33 | −0.03 | −0.93 | −0.51 | methylpropylether | H10C4O1 |
| 0065met | −2.01 | −0.83 | −0.68 | −1.53 | −0.18 | −0.98 | −0.54 | methylisopropylether | H10C4O1 |
| 0066dim | −4.84 | −4.24 | −3.76 | −4.66 | −2.56 | −5.9 | −3.81 | 1,2-dimethoxyethane | H10C4O2 |
| 0067but | −2.21 | −0.32 | −0.22 | −1.37 | −0.06 | −0.79 | −0.42 | t-butylmethylether | H12C5O1 |
| 0068ani | −2.45 | −3.65 | −3.22 | −4.3 | −2.28 | −4.02 | −2.56 | anisole | H8C7O1 |
| 0242dii | −0.53 | 0.34 | 0.38 | −0.81 | 0.37 | 0.21 | 0.24 | isopropylether | H14C6O1 |
| 0244tet | −3.12 | −2.11 | −1.83 | −1.21 | 0.06 | −2.25 | −1.39 | tetrahydropyran | H10C5O1 |
| 0246eth | −2.22 | −1.88 | −1.63 | −3.7 | −1.83 | −3.38 | −2.13 | ethylphenylether | H10C8O1 |
| test0009 | −3.28 | −1.05 | −0.88 | −2.97 | −1.27 | −3.64 | −2.31 | 1,1-diethoxyethane | H14C6O2 |
| test0012 | −2.93 | −5.15 | −4.58 | −5.06 | −2.86 | −6.24 | −4.03 | dimethoxymethane | H8C3O2 |
| test0014 | −3.54 | −0.96 | −0.79 | −3.36 | −1.57 | −4.4 | −2.81 | 1,2-diethoxyethane | H14C6O2 |
| 0091met | −2.78 | −4.28 | −3.79 | −7.85 | −4.98 | −6.82 | −4.12 | methylformate | H4C2O2 |
| 0092ethb | −2.65 | −3.5 | −3.09 | −7.23 | −4.51 | −6.27 | −4.05 | ethylformate | H6C3O2 |
| test0016 | −3.82 | −5.66 | −5.04 | −9.96 | −6.57 | −9.14 | −5.95 | phenylformate | H6C7O2 |
| test2015 | −2.33 | −1.93 | −1.67 | 1.26 | 1.93 | −0.38 | −0.15 | hexachlorobenzene | C6CL6 |
| test2023 | 3.43 | 3.66 | 3.38 | −2.06 | −0.58 | 1.49 | 1.09 | octafluorocyclobutane | C4F8 |
| 0207tri | −4.31 | −3.7 | −3.27 | −11.93 | −8.07 | −9.44 | −6.15 | 2,2,2-trifluoroethanol | H3C2O1F3 |
| 0211tri | −4.16 | −3.21 | −2.82 | −11.26 | −7.56 | −9.2 | −5.99 | 1,1,1-trifluoropropan-2-ol | H5C3O1F3 |
| 0212hex | −3.77 | −2.24 | −1.95 | −15.29 | −10.62 | −11.15 | −7.28 | 1,1,1,3,3,3-hexafluoropropan-2-ol | H2C3O1F6 |
| 0215pbr | −7.13 | −8.04 | −7.18 | −11.31 | −7.6 | −11.25 | −7.35 | p-bromophenol | H5C6O1BR1 |
| test1025 | −9.9 | −12.78 | −11.46 | −14.15 | −9.75 | −15.35 | −10.07 | dicamba | H6C8O3CL2 |
| 0425dbr | −9 | −12.44 | −11.16 | −14.7 | −10.17 | −15.08 | −9.89 | 3,5-dibromo-4-hydroxybenzonitrile | H3C7N1O1BR2 |
| test1048 | −7.8 | −4.74 | −4.21 | −11.49 | −7.74 | −11.46 | −7.49 | propanil | H9C9N1O1CL2 |
| test1007 | −8.2 | −3.88 | −3.43 | −10.73 | −7.16 | −10.05 | −6.55 | alachlor | H20C14N1O2CL1 |
| test2013 | −8.42 | −11.34 | −10.16 | −17.39 | −12.21 | −17.03 | −11.18 | flurbiprofen | H13C15O2F1 |
| test2010 | −9.4 | −15.84 | −14.22 | −17.33 | −12.16 | −17.24 | −11.32 | diflunisal | H8C13O3F2 |
| test3019 | −6.71 | −10.06 | −9.01 | −12.94 | −8.83 | −14.18 | −9.29 | tolfenamicacid | H12C14N1O2CL1 |
| test3020 | −6.3 | −10.92 | −9.79 | −22.37 | −15.99 | −21.19 | −13.94 | diclofenacacid | H11C14N1O2CL2 |
| test3021 | −5.68 | −10.96 | −9.82 | −16.06 | −11.2 | −14.64 | −9.6 | flufenamicacid | H10C14N1O2F3 |
| 0223die | −1.63 | −0.82 | −0.67 | −1.64 | −0.27 | −0.81 | −0.43 | diethyldisulfide | H10C4S2 |
| 0209chl | 0.11 | −0.24 | −0.15 | −9.17 | −5.97 | −5.68 | −3.66 | 1-chloro-2,2,2-trifluoroethyl-difluoromethylether | H2C3O1F5CL1 |
| 0214tri | −0.12 | −1.42 | −1.21 | −6.06 | −3.62 | −3.67 | −2.33 | 2,2,2-trifluoroethylvinylether | H5C4O1F3 |
| test0007 | −4.23 | −1.5 | −1.29 | −4.86 | −2.7 | −5.24 | −3.37 | bis(2-chloroethyl)ether | H8C4O1CL2 |
| test1030 | −5.5 | −7.69 | −6.87 | −4.32 | −2.3 | −6.33 | −4.09 | endrin | H8C12O1CL6 |
| test2029 | −0.8 | −1.69 | −1.46 | −5.48 | −3.18 | −4.96 | −3.18 | trimethylorthotrifluoroacetate | H9C5O3F3 |
| test1049 | −16.4 | −14.33 | −11.96 | −18.79 | −13.27 | −18.84 | −12.38 | pyrazon | H8C10N3O1CL1 |
| test1050 | −10.2 | −11.38 | −10.2 | −11.65 | −7.86 | −14.63 | −9.59 | simazine | H12C7N5CL1 |
| 0428ami | −11.96 | −20.64 | −18.55 | −21.09 | −15.02 | −22.17 | −14.58 | 4-amino-3,5,6-trichloropyridine-2-carboxylicacid | H3C6N2O2CL3 |
| 0426dcl | −5.22 | −7.32 | −6.54 | −4.68 | −2.57 | −5.34 | −3.43 | 2,6-dichlorobenzonitrile | H3C7N1CL2 |
| test1021 | −1.5 | −1.85 | −1.6 | −0.2 | 0.83 | −1.52 | −0.9 | chloropicrin | C1N1O2CL3 |
| test2024 | −5.22 | −4.3 | −3.81 | 0.52 | 1.37 | −2.29 | −1.42 | pentachloronitrobenzene | C6N1O2CL5 |
| test1011 | −3.5 | −4.41 | −3.91 | −4.12 | −2.15 | −4.48 | −2.86 | benefin | H16C13N3O4F3 |
| test1027 | −5.7 | −6.21 | −5.54 | −9.11 | −5.93 | −11.99 | −7.84 | dinitramine | H13C11N4O4F3 |
| test1052 | −11.1 | −7.5 | −6.7 | −13.41 | −9.19 | −14.14 | −9.26 | terbacil | H13C9N2O2CL1 |
| 0440pho | −7.28 | −7.4 | −6.61 | −14.55 | −10.05 | −13 | −8.51 | dimethyl5-(4-chloro)bicyclo[3.2.0]heptylphosphate | H12C9O4P1CL1 |
| test1019 | −7.1 | −5.29 | −4.7 | −11.88 | −8.03 | −10.82 | −7.06 | chlorfenvinphos | H14C12O4P1CL3 |
| test1055 | −12.7 | −11.46 | −10.27 | −21.94 | −15.66 | −20.41 | −13.42 | trichlorfon | H8C4O4P1CL3 |
| test1029 | −4.2 | −10.4 | −9.32 | −10.19 | −6.75 | −13.89 | −9.1 | endosulfanalpha | H6C9O3S1CL6 |
| 0213bis | −3.92 | −1.11 | −0.93 | −4.5 | −2.43 | −4.61 | −2.95 | bis(2-chloroethyl)sulfide | H8C4S1CL2 |
| 0438pho | −3.86 | −4.72 | −4.19 | −9.78 | −6.44 | −9.82 | −6.4 | diethyl2,4-dichlorophenylthiophosphate | H13C10O3P1S1CL2 |
| 0441pho | −7.62 | −20.61 | −18.53 | −12.75 | −8.69 | −15.07 | −9.88 | dimethyl4-nitrophenylthiophosphate | H10C8N1O5P1S1 |
| 0442pho | −4.09 | −5.49 | −4.88 | −12 | −8.12 | −11.74 | −7.67 | O-ethylO'-4-bromo-2-chlorophenylS-propylphosphorothioate | H15C11O3P1S1CL1BR1 |
| 0444pho | −5.06 | −6.02 | −5.36 | −10.23 | −6.78 | −10.87 | −7.1 | dimethyl2,4,5-trichlorophenylthiophosphate | H8C8O3P1S1CL3 |

TABLE 7-continued

KMTISM, MM-GBSA and MM-PBSA calculated solvation free energy (in kcal/mol) results against the test set with 372 neutral compounds.

| Compound ID | Exp. ΔGsolv | KMTISM Raw Result | KMTISM Scaled Result | MM-GBSA Raw Result | MM-GBSA Scaled Result | MM-PBSA Raw Result | MM-PBSA Scaled Result | Solute Name | Formula |
|---|---|---|---|---|---|---|---|---|---|
| 0445pho | −5.7 | −6.46 | −5.76 | −10.24 | −6.79 | −11.32 | −7.39 | dimethyl4-bromo-2,5-dichlorophenylthiophosphate | H8C8O3P1S1CL2BR1 |
| test1017 | −6.5 | −5.51 | −4.9 | −12.62 | −8.59 | −14.79 | −9.7 | carbophenothion | H16C11O2P1S3CL1 |
| test1022 | −5 | −8.21 | −7.34 | −13.53 | −9.28 | −13.31 | −8.71 | chlorpyrifos | H11C9N1O3P1S1CL3 |
| 0427dcl | −10.81 | −8.63 | −7.71 | −8.79 | −5.69 | −9.44 | −6.15 | 2,6-dichlorothiobenzamide | H5C7N1S1CL2 |
| 0433pho | −6.61 | −9.13 | −8.17 | −15.3 | −10.62 | −13.89 | −9.1 | 2,2-dichloroethenyl-dimethylphosphate | H7C4O4P1CL2 |
| 0153flu | −0.22 | 1.41 | 1.35 | −1.77 | −0.37 | 0.04 | 0.13 | fluoromethane | H3C1F1 |
| 0154dif | −0.11 | 2.01 | 1.89 | −2.88 | −1.21 | −0.91 | −0.5 | 1,1-difluoroethane | H4C2F2 |
| 0157flu | −0.78 | −1.14 | −0.95 | −2.33 | −0.79 | −1.29 | −0.75 | fluorobenzene | H5C6F1 |
| 0160chl | −0.56 | 0.21 | 0.26 | −1.3 | −0.01 | −0.1 | 0.03 | chloromethane | HC1CL1 |
| 0161dic | −1.36 | −0.59 | −0.46 | −2.04 | −0.57 | −1.32 | −0.77 | dichloromethane | H2C1CL2 |
| 0162tri | −1.07 | −1.33 | −1.13 | −1.8 | −0.38 | −1.08 | −0.61 | chloroform | H1C1CL3 |
| 0163chl | −0.63 | 0.59 | 0.61 | −1.04 | 0.19 | 0.1 | 0.17 | chloroethane | H5C2CL1 |
| 0165tri | −0.25 | −0.89 | −0.73 | −1.01 | 0.22 | −0.42 | −0.18 | 1,1,1-trichloroethane | H3C2CL3 |
| 0166tri | −1.95 | −0.96 | −0.79 | −3.22 | −1.47 | −2.72 | −1.7 | 1,1,2-trichloroethane | H3C2CL3 |
| 0167chla | −0.27 | 0.84 | 0.83 | −0.71 | 0.44 | 0.35 | 0.33 | 1-chloropropane | H7C3CL1 |
| 0168chl | −0.25 | 0.86 | 0.85 | −1.1 | 0.15 | 0.27 | 0.28 | 2-chloropropane | H7C3CL1 |
| 0169chl | −0.59 | −1.38 | −1.18 | −1.11 | 0.13 | 0.26 | 0.28 | chloroethene | H3C2CL1 |
| 0170chl | −0.57 | −0.74 | −0.6 | −1.52 | −0.17 | −0.17 | −0.01 | 3-chloropropene | H5C3CL1 |
| 0171Zdi | −1.17 | −1.78 | −1.53 | −1.86 | −0.43 | −1.19 | −0.68 | Z-1,2-dichloroethene | H2C2CL2 |
| 0172Edi | −0.76 | −1.83 | −1.58 | −0.81 | 0.36 | −0.13 | 0.02 | E-1,2-dichloroethene | H2C2CL2 |
| 0173tri | −0.39 | −1.72 | −1.48 | −0.4 | 0.67 | −0.1 | 0.04 | trichloroethene | H1C2CL3 |
| 0174chl | −1.12 | −1.66 | −1.42 | −2.27 | −0.74 | −1.83 | −1.11 | chlorobenzene | H5C6CL1 |
| 0175odi | −1.36 | −1.73 | −1.49 | −1.98 | −0.52 | −1.75 | −1.05 | 1,2-dichlorobenzene | H4C6CL2 |
| 0176pdi | −1.01 | −1.78 | −1.53 | −1.81 | −0.4 | −1.49 | −0.88 | 1,4-dichlorobenzene | H4C6CL2 |
| 0177bro | −0.82 | −0.38 | −0.27 | −1.42 | −0.1 | −0.65 | −0.33 | bromomethane | H3C1BR1 |
| 0178dib | −2.11 | −1.66 | −1.42 | −1.54 | −0.19 | −1.78 | −1.08 | dibromomethane | H2C1BR2 |
| 0179tri | −1.98 | −2.89 | −2.54 | −0.7 | 0.45 | −1.5 | −0.89 | bromoform | H1C1BR3 |
| 0180bro | −0.7 | 0.06 | 0.13 | −1.33 | −0.03 | −0.55 | −0.26 | bromoethane | H5C2BR1 |
| 0182bro | −0.56 | 0.31 | 0.35 | −1.01 | 0.21 | −0.33 | −0.11 | 1-bromopropane | H7C3BR1 |
| 0183bro | −0.48 | 0.38 | 0.42 | −1.51 | −0.17 | −0.43 | −0.18 | 2-bromopropane | H7C3BR1 |
| 0184bro | −0.41 | 0.57 | 0.59 | −0.76 | 0.4 | −0.02 | 0.09 | 1-bromobutane | H9C4BR1 |
| 0185bro | −0.08 | 0.8 | 0.8 | −0.54 | 0.57 | 0.22 | 0.25 | 1-bromopentane | H11C5BR1 |
| 0186bro | −1.46 | −2.14 | −1.86 | −2.63 | −1.02 | −2.56 | −1.59 | bromobenzene | H5C6BR1 |
| 0187dib | −2.3 | −2.68 | −2.34 | −2.28 | −0.75 | −2.76 | −1.72 | p-dibromobenzene | H4C6BR2 |
| 0197bro | 1.79 | 0.71 | 0.71 | −2.81 | −1.15 | 0.23 | 0.25 | bromotrifluoromethane | C1F3BR1 |
| 0198chl | −0.77 | 0.56 | 0.58 | −3.36 | −1.57 | −1.91 | −1.16 | chlorofluoromethane | H2C1F1CL1 |
| 0199chl | −0.5 | 0.92 | 0.9 | −4.64 | −2.54 | −2.07 | −1.27 | chlorodifluoromethane | H1C1F2CL1 |
| 0200tet | 3.16 | 2.44 | 2.27 | −3.45 | −1.64 | 1.44 | 1.06 | tetrafluoromethane | C1F4 |
| 0201bro | −0.13 | 0.13 | 0.19 | −3.6 | −1.76 | −1.27 | −0.74 | 1-bromo-1-chloro-2,2,2-trifluoroethane | H1C2F3CL1BR1 |
| 0202bro | −1.95 | −0.78 | −0.63 | −2.99 | −1.29 | −2.81 | −1.76 | 1-bromo-2-chloroethane | H4C2CL1BR1 |
| 0203bro | 0.52 | 1.22 | 1.17 | −4.89 | −2.73 | −1.78 | −1.08 | 1-bromo-1,2,2,2-tetrafluoroethane | H1C2F4BR1 |
| 0204tet | 0.05 | −1.64 | −1.4 | 1 | 1.74 | 0.72 | 0.58 | tetrachloroethene | C2CL4 |
| 0205chl | 0.06 | 1.45 | 1.38 | −3.94 | −2.01 | −1.55 | −0.92 | 1-chloro-2,2,2-trifluoroethane | H2C2F3CL1 |
| 0206tri | 1.77 | −0.1 | −0.02 | −2.49 | −0.91 | 0.61 | 0.51 | 1,1,2-trichloro-1,2,2-trifluoroethane | C2F3CL3 |
| 0405hex | 3.94 | 3.13 | 2.9 | −4.18 | −2.2 | 1.08 | 0.82 | hexafluoroethane | C2F6 |
| 0406oct | 4.28 | 3.54 | 3.27 | −3.62 | −1.76 | 1.33 | 0.98 | octafluoropropane | C3F8 |
| 0407tet | −1.15 | −1.64 | −1.4 | −1.86 | −0.43 | −1.51 | −0.89 | 1,1,1,2-tetrachloroethane | H2C2CL4 |
| 0408hex | −1.4 | −2.76 | −2.42 | −0.27 | 0.78 | 0.12 | 0.18 | hexachloroethane | C2CL6 |
| 0409clb | 0.07 | 1.13 | 1.09 | −0.81 | 0.36 | 0.47 | 0.42 | 2-chlorobutane | H9C4CL1 |
| 0410clp | 0.07 | 1.34 | 1.28 | −0.25 | 0.79 | 0.81 | 0.64 | 1-chloropentane | H11C5CL1 |
| 0411chp | 0.07 | 1.45 | 1.38 | −0.58 | 0.54 | 0.76 | 0.61 | 2-chloropentane | H11C5CL1 |
| 0412clt | −1.92 | −1.43 | −1.22 | −3.54 | −1.71 | −3.1 | −1.95 | chlorotoluene | H7C7CL1 |
| 0413clt | −1.15 | −0.88 | −0.73 | −2.11 | −0.62 | −1.53 | −0.91 | o-chlorotoluene | H7C7CL1 |
| 0414dcl | −2.73 | −2.57 | −2.24 | −4.09 | −2.13 | −3.48 | −2.21 | 2,2′-dichlorobiphenyl | H8C12CL2 |
| 0415dcl | −2.45 | −2.49 | −2.18 | −3.78 | −1.89 | −3.85 | −2.45 | 2,3-dichlorobiphenyl | H8C12CL2 |
| 0416dcl | −1.99 | −2.65 | −2.32 | −3.63 | −1.77 | −3.36 | −2.12 | 2,2′,3′-trichlorobiphenyl | H7C12CL3 |
| 0417brp | −0.86 | −1.33 | −1.13 | −1.73 | −0.34 | −0.75 | −0.39 | 3-bromopropene | H5C3BR1 |
| 0418bri | −0.03 | 0.53 | 0.55 | −1 | 0.22 | −0.09 | 0.05 | 1-bromo-isobutane | H9C4BR1 |
| 0419brt | −2.37 | −1.9 | −1.64 | −3.89 | −1.97 | −3.77 | −2.4 | bromotoluene | H7C7BR1 |
| 0420pbr | −1.39 | −1.31 | −1.1 | −2.35 | −0.8 | −2.18 | −1.34 | p-bromotoluene | H7C7BR1 |
| 0421dfl | 1.69 | 0.08 | 0.15 | −2.01 | −0.55 | 0.71 | 0.57 | difluorodichloromethane | C1F2CL2 |
| 0422ftc | 0.82 | −1.02 | −0.85 | −1.13 | 0.12 | 0.54 | 0.46 | fluorotrichloromethane | C1F1CL3 |
| 0423brt | −0.93 | −2.54 | −2.22 | 0.1 | 1.05 | 0.09 | 0.16 | bromotrichloromethane | C1CL3BR1 |
| 0424clp | 2.86 | 2 | 1.88 | −3.64 | −1.78 | 1.02 | 0.78 | chloropentaflouroethane | C2F5CL1 |

TABLE 7-continued

KMTISM, MM-GBSA and MM-PBSA calculated solvation free energy (in kcal/mol) results against the test set with 372 neutral compounds.

| Compound ID | Exp. ΔGsolv | KMTISM Raw Result | KMTISM Scaled Result | MM-GBSA Raw Result | MM-GBSA Scaled Result | MM-PBSA Raw Result | MM-PBSA Scaled Result | Solute Name | Formula |
|---|---|---|---|---|---|---|---|---|---|
| test0004 | 1.07 | 1.81 | 1.71 | −6.15 | −3.69 | −2.66 | −1.66 | m-bis(trifluoromethyl)benzene | H4C8F6 |
| test1018 | −3.4 | −3.03 | −2.66 | −2.12 | −0.63 | −2.39 | −1.48 | chlordane | H6C10CL8 |
| test1033 | −2.6 | −3.26 | −2.87 | −1.67 | −0.29 | −1.97 | −1.2 | heptachlor | H5C10CL7 |
| test1035 | −5.4 | −1.99 | −1.73 | −5.45 | −3.16 | −5.47 | −3.52 | lindane | H6C6CL6 |
| 0116pyr | −4.7 | −5.22 | −4.64 | −6.09 | −3.64 | −5.43 | −3.49 | pyridine | H5C5N1 |
| 0117met | −5.57 | −7.53 | −6.72 | −9.78 | −6.44 | −9.42 | −6.14 | 2-methylpyrazine | H6C5N2 |
| 0119met | −4.63 | −4.4 | −3.89 | −5.7 | −3.35 | −4.87 | −3.12 | 2-methylpyridine | H7C6N1 |
| 0120met | −4.77 | −4.89 | −4.34 | −5.63 | −3.29 | −4.98 | −3.2 | 3-methylpyridine | H7C6N1 |
| 0121met | −4.94 | −4.89 | −4.34 | −5.89 | −3.49 | −5.16 | −3.32 | 4-methylpyridine | H7C6N1 |
| 0122Nme | −4.68 | −2.59 | −2.26 | −6.25 | −3.76 | −6.37 | −4.12 | N-methylaniline | H9C7N1 |
| 0123dim | −4.86 | −3.36 | −2.96 | −5.47 | −3.17 | −4.51 | −2.89 | 2,4-dimethylpyridine | H9C7N1 |
| 0124dim | −4.72 | −3.5 | −3.09 | −5.22 | −2.98 | −4.26 | −2.72 | 2,5-dimethylpyridine | H9C7N1 |
| 0125dim | −4.6 | −2.67 | −2.34 | −5.3 | −3.04 | −4.23 | −2.7 | 2,6-dimethylpyridine | H9C7N1 |
| 0230eth | −5.51 | −7.16 | −6.39 | −9.23 | −6.02 | −8.71 | −5.67 | 2-ethylpyrazine | H8C6N2 |
| 0471dim | −5.22 | −4.3 | −3.81 | −5.48 | −3.18 | −4.83 | −3.1 | 3,4-dimethylpyridine | H9C7N1 |
| 0571dim | −4.84 | −3.99 | −3.53 | −5.15 | −2.93 | −4.32 | −2.76 | 3,5-dimethylpyridine | H9C7N1 |
| 0574eth | −4.74 | −6.25 | −5.57 | −5.81 | −3.43 | −5.93 | −3.82 | 4-ethylpyridine | H9C7N1 |
| test0017 | −9.81 | −8.7 | −7.78 | −10.3 | −6.83 | −10.46 | −6.83 | imidazole | H4C3N2 |
| test1009 | −7.7 | −10.88 | −9.75 | −9.02 | −5.86 | −12.23 | −8 | ametryn | H17C9N5S1 |
| test1047 | −8.4 | −8.37 | −7.48 | −8.31 | −5.33 | −11.25 | −7.35 | prometryn | H19C10N5S1 |
| test1053 | −6.7 | −9.3 | −8.32 | −9.11 | −5.93 | −12.2 | −7.98 | terbutryn | H19C10N5S1 |
| test1063 | −9.4 | −4.62 | −4.09 | −14.17 | −9.77 | −16.19 | −10.62 | pirimicarb | H18C11N4O2 |
| n005 | −5.31 | −6.72 | −5.99 | −10.54 | −7.01 | −8.76 | −5.7 | methylhydrazine | H6C1N2 |
| n006 | −4.48 | −6.33 | −5.64 | −7.69 | −4.85 | −7.75 | −5.03 | 1,1-dimethylhydrazine | H8C2N2 |
| 0001met | 2 | 1.02 | 1 | −0.05 | 0.94 | 2.57 | 1.8 | methane | H4C1 |
| 0002eth | 1.83 | 1.39 | 1.33 | 0.69 | 1.5 | 2.65 | 1.86 | ethane | H6C2 |
| 0003pro | 1.96 | 1.67 | 1.58 | 0.93 | 1.68 | 2.72 | 1.91 | n-propane | H8C3 |
| 0004nbu | 2.08 | 1.95 | 1.83 | 1.15 | 1.85 | 2.9 | 2.02 | n-butane | H10C4 |
| 0005npe | 2.33 | 2.18 | 2.04 | 1.36 | 2.01 | 3.09 | 2.15 | n-pentane | H12C5 |
| 0006nhe | 2.49 | 2.45 | 2.28 | 1.57 | 2.17 | 3.33 | 2.31 | n-hexane | H14C6 |
| 0007nhe | 2.62 | 2.71 | 2.52 | 1.8 | 2.35 | 3.57 | 2.47 | n-heptane | H16C7 |
| 0008noc | 2.89 | 3.01 | 2.79 | 2.02 | 2.51 | 3.79 | 2.61 | n-octane | H18C8 |
| 0010met | 2.32 | 1.83 | 1.72 | 0.88 | 1.65 | 2.8 | 1.96 | 2-methylpropane | H10C4 |
| 0011met | 2.5 | 1.88 | 1.77 | 1.05 | 1.77 | 2.87 | 2.01 | 2,2-dimethylpropane | H12C5 |
| 0012met | 2.52 | 2.28 | 2.13 | 1.32 | 1.98 | 3.22 | 2.24 | 2-methylpentane | H14C6 |
| 0013dim | 2.88 | 2.35 | 2.19 | 1.31 | 1.97 | 3.4 | 2.35 | 2,4-dimethylpentane | H16C7 |
| 0014tri | 2.85 | 2.39 | 2.23 | 1.45 | 2.08 | 3.39 | 2.35 | 2,2,4-trimethylpentane | H18C8 |
| 0016cyc | 0.75 | 1.63 | 1.55 | 0.51 | 1.37 | 2.48 | 1.75 | cyclopropane | H6C3 |
| 0017cyc | 1.2 | 2.03 | 1.91 | 1.21 | 1.9 | 1.92 | 1.37 | cyclopentane | H10C5 |
| 0018cyc | 1.23 | 2.19 | 2.05 | 1.38 | 2.03 | 2.03 | 1.45 | cyclohexane | H12C6 |
| 0019met | 1.71 | 2.35 | 2.2 | 1.39 | 2.04 | 2.26 | 1.6 | methylcyclohexane | H14C7 |
| 0020cis | 1.58 | 2.46 | 2.3 | 1.38 | 2.03 | 2.37 | 1.67 | cis-1,2-dimethylcyclohexane | H16C8 |
| 0021eth | 1.27 | −0.96 | −0.79 | −0.34 | 0.72 | 1.98 | 1.41 | ethene | H4C2 |
| 0022pro | 1.27 | −0.06 | 0.02 | −0.03 | 0.95 | 2.03 | 1.45 | propene | H6C3 |
| 0023str | 0.61 | −1.35 | −1.14 | −0.78 | 0.39 | 1.37 | 1.01 | s-trans-1,3-butadiene | H6C4 |
| 0024met | 1.16 | 0.67 | 0.68 | −0.01 | 0.97 | 2.03 | 1.45 | 2-methylpropene | H8C4 |
| 0025buta | 1.38 | 0.29 | 0.34 | 0.24 | 1.16 | 2.19 | 1.56 | 1-butene | H8C4 |
| 0026cyc | 0.56 | 0.7 | 0.7 | 0.08 | 1.04 | 0.89 | 0.69 | cyclopentene | H8C5 |
| 0027pen | 1.66 | 0.57 | 0.59 | 0.49 | 1.35 | 2.44 | 1.72 | 1-pentene | H10C5 |
| 0028Epe | 1.34 | 1.23 | 1.19 | 0.6 | 1.43 | 2.44 | 1.72 | E-2-pentene | H10C5 |
| 0029hex | 1.68 | 0.84 | 0.83 | 0.71 | 1.52 | 2.65 | 1.86 | 1-hexene | H12C6 |
| 0030eth | −0.01 | −1 | −0.83 | −1.07 | 0.17 | −0.68 | −0.35 | ethyne | H2C2 |
| 0031pro | −0.31 | −0.09 | −0.01 | −1.06 | 0.17 | −0.74 | −0.38 | propyne | H4C3 |
| 0032but | −0.16 | 0.28 | 0.33 | −0.71 | 0.44 | −0.38 | −0.15 | 1-butyne | H6C4 |
| 0033pen | 0.01 | 0.63 | 0.64 | −0.44 | 0.64 | −0.08 | 0.05 | 1-pentyne | H8C5 |
| 0034hex | 0.29 | 0.8 | 0.8 | −0.2 | 0.82 | 0.13 | 0.19 | 1-hexyne | H10C6 |
| 0035ben | −0.87 | −1.59 | −1.36 | −1.59 | −0.99 | −1.77 | −1.07 | benzene | H6C6 |
| 0036tol | −0.89 | −0.74 | −0.6 | −2.34 | −0.8 | −1.45 | −0.86 | toluene | H8C7 |
| 0037eth | −0.8 | −0.34 | −0.24 | −1.96 | −0.51 | −1.09 | −0.62 | ethylbenzene | H10C8 |
| 0038oxy | −0.9 | −0.09 | −0.01 | −2.12 | −0.63 | −1.28 | −0.75 | o-xylene | H10C8 |
| 0039mxy | −0.84 | 0.11 | 0.17 | −2.02 | −0.56 | −1.08 | −0.61 | m-xylene | H10C8 |
| 0040pxy | −0.81 | 0.16 | 0.22 | −2.01 | −0.55 | −1.06 | −0.6 | p-xylene | H10C8 |
| 0041nap | −2.39 | −2.08 | −1.81 | −4.31 | −2.29 | −4.59 | −2.94 | naphthalene | H8C10 |
| 0042ant | −4.23 | −2.54 | −2.22 | −5.68 | −3.33 | −6.98 | −4.52 | anthracene | H10C14 |
| 0148but | 0.04 | −1.42 | −1.21 | −2.21 | −0.7 | −1.61 | −0.96 | butenyne | H4C4 |
| test2025 | −9.61 | −14.4 | −12.93 | −15.14 | −10.5 | −15.2 | −9.97 | phthalimide | H5C8N1O2 |
| 0075pro | −3.85 | −4.13 | −3.65 | −6.06 | −3.62 | −4.51 | −2.88 | acetone | H6C3O1 |
| 0076but | −3.64 | −3.19 | −2.8 | −5.51 | −3.2 | −3.91 | −2.48 | 2-butanone | H8C4O1 |
| 0077cyc | −4.68 | −4.08 | −3.61 | −5.23 | −2.99 | −4.62 | −2.96 | cyclopentanone | H8C5O1 |
| 0078pen | −3.53 | −2.93 | −2.58 | −5.22 | −2.98 | −3.66 | −2.32 | 2-pentanone | H10C5O1 |
| 0079pen | −3.41 | −1.92 | −1.66 | −4.95 | −2.78 | −3.31 | −2.09 | 3-pentanone | H10C5O1 |
| 0080hex | −3.29 | −2.62 | −2.29 | −4.96 | −2.78 | −3.43 | −2.17 | 2-hexanone | H12C6O1 |

TABLE 7-continued

KMTISM, MM-GBSA and MM-PBSA calculated solvation free energy (in kcal/mol) results against the test set with 372 neutral compounds.

| Compound ID | Exp. ΔGsolv | KMTISM Raw Result | KMTISM Scaled Result | MM-GBSA Raw Result | MM-GBSA Scaled Result | MM-PBSA Raw Result | MM-PBSA Scaled Result | Solute Name | Formula |
|---|---|---|---|---|---|---|---|---|---|
| 0081dim | −2.89 | −2.77 | −2.43 | −4.90 | −2.81 | −3.36 | −2.12 | 3,3-dimethylbutanone | H12C6O1 |
| 0082hep | −3.04 | −2.45 | −2.14 | −4.72 | −2.6 | −3.18 | −2.01 | 2-heptanone | H14C7O1 |
| 0083hep | −2.93 | −1.59 | −1.36 | −4.43 | −2.38 | −2.65 | −1.65 | 4-heptanone | H14C7O1 |
| 0084met | −4.58 | −5.46 | −4.86 | −7.94 | −5.04 | −7.16 | −4.64 | acetophenone | H8C8O1 |
| 0085non | −2.67 | −0.91 | −0.75 | −3.89 | −1.97 | −2.01 | −1.23 | 5-nonanone | H18C9O1 |
| 0239oct | −2.88 | −2.04 | −1.77 | −4.51 | −2.44 | −2.92 | −1.83 | 2-octanone | H16C8O1 |
| test1034 | −5.2 | −3.95 | −3.49 | −5.7 | −3.34 | −4.18 | −2.66 | isophorone | H14C9O1 |
| test1001 | −5.7 | −6.53 | −5.82 | −5.56 | −3.24 | −9.7 | −6.32 | nitroglycol | H4C2N2O6 |
| test1002 | −5 | −5.57 | −4.96 | −5.22 | −2.98 | −9.01 | −5.87 | 1,2-dinitroxypropane | H6C3N2O6 |
| test1003 | −2.1 | −2.92 | −2.57 | −1.64 | −0.27 | −2.94 | −1.84 | butylnitrate | H9C4N1O3 |
| test1004 | −1.8 | −2.15 | −1.87 | −1.87 | −0.44 | −2.97 | −1.86 | 2-butylnitrate | H9C4N1O3 |
| test1005 | −1.9 | −2.59 | −2.27 | −1.72 | −0.33 | −2.79 | −1.74 | isobutylnitrate | H9C4N1O3 |
| test1006 | −8.2 | −9.17 | −8.2 | −11 | −7.37 | −13.25 | −8.67 | ethyleneglycolmononitrate | H5C2N1O4 |
| 0126eth | −3.89 | −4.93 | −4.38 | −5.3 | −3.04 | −4.54 | −2.9 | acetonitrile | H3C2N1 |
| 0127pro | −3.85 | −4.62 | −4.1 | −4.64 | −2.54 | −3.93 | −2.5 | propionitrile | H5C3N1 |
| 0128butb | −3.64 | −4.32 | −3.82 | −4.35 | −2.32 | −3.63 | −2.3 | butanonitrile | H7C4N1 |
| 0129ben | −4.1 | −6.77 | −6.04 | −5.56 | −3.24 | −5.56 | −3.58 | benzonitrile | H5C7N1 |
| 0506nit | −3.95 | −5.88 | −5.24 | −2.73 | −1.09 | −3.66 | −2.32 | nitromethane | H3C1N1O2 |
| 0130nit | −3.71 | −4.36 | −3.86 | −2.35 | −0.8 | −3.14 | −1.98 | nitroethane | H5C2N1O2 |
| 0131nit | −3.34 | −4.02 | −3.56 | −1.97 | −0.52 | −2.71 | −1.69 | 1-nitropropane | H7C3N1O2 |
| 0132nit | −3.14 | −2.88 | −2.52 | −2.26 | −0.74 | −2.63 | −1.64 | 2-nitropropane | H7C3N1O2 |
| 0133nit | −3.08 | −3.92 | −3.47 | −1.72 | −0.33 | −2.4 | −1.48 | 1-nitrobutane | H9C4N1O2 |
| 0134nit | −4.12 | −6.04 | −5.38 | −4.25 | −2.25 | −5.69 | −3.67 | nitrobenzene | H5C6N1O2 |
| 0135met | −3.59 | −4.18 | −3.7 | −4.4 | −2.36 | −5.59 | −3.6 | 2-methyl-1-nitrobenzene | H7C7N1O2 |
| test1028 | −6.2 | −8.68 | −7.76 | −11.3 | −7.59 | −13.15 | −8.61 | dinoseb | H12C10N2O5 |
| test1058 | −11.2 | −12.76 | −11.44 | −13.68 | −9.39 | −15.24 | −9.99 | 4-amino-4'-nitroazobenzene | H10C12N4O2 |
| test2022 | −9.45 | −12.16 | −10.9 | −10.07 | −6.66 | −11.81 | −7.72 | 4-nitroaniline | H6C6N2O2 |
| test1046 | −2.5 | −3.37 | −2.97 | −4.67 | −2.56 | −4.76 | −3.05 | profluralin | H16C14N3O4F3 |
| test1056 | −3.3 | −3.04 | −2.67 | −4.67 | −2.56 | −4.99 | −3.2 | trifluralin | H16C13N3O4F3 |
| test1041 | −6 | −9.54 | −8.54 | −9.33 | −6.1 | −10.51 | −6.86 | nitroxyacetone | H5C3N1O4 |
| 0402adn | −13.6 | −18.22 | −16.37 | −18.38 | −12.96 | −19.59 | −12.87 | 9-methyladenine | H7C6N5 |
| 0403thi | −10.4 | −11.48 | −10.29 | −16.32 | −11.4 | −17.04 | −11.18 | 1-methylthymine | H8C6N2O2 |
| n191 | −16.59 | −15.77 | −14.16 | −18.49 | −13.05 | −19.38 | −12.74 | uracil | H4C4N2O2 |
| n200 | −16.92 | −11.46 | −10.27 | −18.65 | −13.16 | −19.54 | −12.84 | 5-fluorouracil | H3C4N2O2F1 |
| n201 | −15.46 | −12.9 | −11.57 | −21.18 | −15.08 | −21.13 | −13.89 | 5-trifluoromethyluracil | H3C5N2O2F3 |
| n202 | −17.74 | −15.8 | −14.18 | −18.25 | −12.86 | −19.5 | −12.81 | 5-chlorouracil | H3C4N2O2CL1 |
| n203 | −18.17 | −15 | −13.47 | −18.54 | −13.08 | −20.24 | −13.31 | 5-bromouracil | H3C4N2O2BR1 |
| test2004 | −12.64 | −12.01 | −10.76 | −18.95 | −13.39 | −21.27 | −13.98 | caffeine | H10C8N4O2 |
| test2006 | −15.83 | −15.51 | −13.92 | −16.25 | −11.35 | −17.51 | −11.5 | 6-chlorouracil | H3C4N2O2CL1 |
| test1013 | −9.7 | −8.09 | −7.23 | −14.11 | −9.72 | −14.48 | −9.49 | bromacil | H13C9N2O2BR1 |
| n018 | −5.28 | −9.9 | −8.87 | −9.89 | −6.52 | −9.07 | −5.9 | methylperoxide | H4C1O2 |
| n019 | −5.32 | −10.27 | −9.2 | −9.21 | −6 | −8.59 | −5.59 | ethylperoxide | H6C2O2 |
| 0220tri | −8.7 | −9.38 | −8.39 | −14.22 | −9.8 | −14.22 | −9.31 | trimethylphoshate | H9C3O4P1 |
| 0221tri | −7.8 | −4.67 | −4.14 | −11.55 | −7.78 | −11.33 | −7.4 | triethylphosphate | H15C6O4P1 |
| 0222tri | −6.1 | −3.89 | −3.44 | −10.3 | −6.83 | −9.4 | −6.12 | tripropylphosphate | H21C9O4P1 |
| test2027 | −8.61 | −10.18 | −9.12 | −13.12 | −8.97 | −13.73 | −8.99 | sulfolane | H8C4O2S1 |
| test1040 | −8 | −12.36 | −11.09 | −15.07 | −10.45 | −15.7 | −10.3 | nitralin | H19C13N3O6S1 |
| test1039 | −15.5 | −25.61 | −23.04 | −32.58 | −23.73 | −35.93 | −23.7 | metsulfuronmethyl | H15C14N5O6S1 |
| test1057 | −4.1 | −1.81 | −1.56 | −4.63 | −2.53 | −3.88 | −2.47 | vemolate | H21C10N1O1S1 |
| 0136met | −1.24 | −2.05 | −1.78 | −2.78 | −1.13 | −2.09 | −1.28 | methanethiol | H4C1S1 |
| 0137ethb | −1.3 | −1.52 | −1.3 | −2.61 | −1 | −1.95 | −1.19 | ethanethiol | H6C2S1 |
| 0138pro | −1.05 | −1.25 | −1.05 | −2.21 | −0.69 | −1.62 | −0.97 | 1-propanethiol | H8C3S1 |
| 0139thi | −2.55 | −3.43 | −3.03 | −3.81 | −1.92 | −3.88 | −2.46 | thiophenol | H6C6S1 |
| 0140dim | −1.54 | −0.64 | −0.5 | −1.47 | −0.14 | −0.51 | −0.24 | dimethylsulfide | H6C2S1 |
| 0141dim | −1.83 | −2.04 | −1.77 | −1.93 | −0.49 | −1.4 | −0.82 | dimethyldisulfide | H6C2S2 |
| 0142die | −1.43 | 0.52 | 0.55 | −1.24 | 0.04 | −0.21 | −0.04 | diethylsulfide | H10C4S1 |
| 0143dip | −1.27 | 1.05 | 1.02 | −0.57 | 0.54 | 0.52 | 0.45 | dipropylsulfide | H14C6S1 |
| 0144thi | −2.73 | −2.13 | −1.85 | −2.78 | −1.13 | −2.47 | −1.53 | thioanisole | H8C7S1 |
| 0245thi | −1.42 | −2.95 | −2.59 | −1.95 | −0.5 | −1.69 | −1.02 | thiophene | H4C4S1 |
| test1044 | −3.6 | −1.72 | −1.48 | −4.74 | −2.62 | −4.23 | −2.7 | pebulate | H21C10N1O1S1 |
| test1031 | −6.1 | −2.46 | −2.15 | −17.95 | −12.64 | −17.98 | −11.81 | ethion | H22C9O4P2S4 |
| test1036 | −8.2 | −12.93 | −11.6 | −19.82 | −14.05 | −18.93 | −12.44 | malathion | H19C10O6P1S2 |
| test1024 | −6.5 | −6.6 | −5.89 | −12.5 | −8.5 | −12.4 | −8.11 | diazinon | H21C12N2O3P1S1 |
| 0449pho | −5.1 | −8.61 | −7.7 | −18.15 | −12.78 | −17.51 | −11.5 | ethyl4-cyanophenylphenyl-thiophosphonate | H14C15N1O2P1S1 |
| 0447pho | −6.27 | −8.29 | −7.41 | −10.9 | −7.29 | −12.95 | −8.48 | diethyl4-nitrophenylthiophosphonate | H14C10N1O2P1S1 |
| test1043 | −6.7 | −17.84 | −16.03 | −11.03 | −7.38 | −13.03 | −8.53 | parathion | H14C10N1O5P1S1 |
| test1045 | −4.4 | −2.93 | −2.57 | −8.28 | −5.3 | −9.2 | −5.99 | phorate | H17C7O2P1S3 |
| test1010 | −10 | −15.51 | −13.93 | −18.66 | −13.17 | −21.58 | −14.19 | azinphosmethyl | H12C10N3O3P1S2 |
| 0401amia | −9.63 | −10.58 | −9.48 | −13.36 | −9.15 | −13.74 | −9 | 1,1-dimethyl-3-phenylurea | H12C9N2O1 |
| n007 | −13.8 | −15.47 | −13.89 | −13.57 | −9.31 | −13.91 | −9.11 | urea | H4C1N2O1 |

TABLE 7-continued

KMTISM, MM-GBSA and MM-PBSA calculated solvation free energy (in kcal/mol) results against the test set with 372 neutral compounds.

| Compound ID | Exp. ΔGsolv | KMTISM Raw Result | KMTISM Scaled Result | MM-GBSA Raw Result | MM-GBSA Scaled Result | MM-PBSA Raw Result | MM-PBSA Scaled Result | Solute Name | Formula |
|---|---|---|---|---|---|---|---|---|---|
| test2007 | −18.06 | −21.51 | −19.34 | −22.88 | −16.37 | −25.87 | −17.04 | cyanuricacid | H3C3N3O3 |
| 0437pho | −6.92 | −12.07 | −10.82 | −18.48 | −13.04 | −20.99 | −13.8 | methyl3-methyl-4-thiomethoxyphenyl-thiophosphate | H13C9O3P1S2 |
| test1012 | −17.2 | −27.37 | −24.63 | −33.94 | −24.76 | −38.29 | −25.26 | bensulfuron | H18C16N4O7S1 |
| test1014 | −9 | −9.95 | −8.91 | −11.05 | −7.4 | −11.57 | −7.56 | captan | H8C9N1O2S1CL3 |
| test1020 | −14 | −23.13 | −20.8 | −34.54 | −25.21 | −37.03 | −24.43 | chlorimuronethyl | H15C15N4O6S1CL1 |
| test1023 | −5.7 | −10.04 | −8.99 | −29.24 | −21.19 | −28.85 | −19.01 | dialifor | H17C14N1O4P1S2CL1 |
| test1051 | −20.3 | −21.56 | −19.39 | −30.85 | −22.42 | −32.58 | −21.48 | sulfometuron-methyl | H16C15N4O5S1 |
| test1054 | −16.2 | −25.7 | −23.12 | −36.05 | −26.36 | −38.78 | −25.59 | thifensulfuron | H13C12N5O6S2 |

TABLE 8

KMTISM, MM-GBSA and MM-PBSA calculated solvation free energy (in kcal/mol) results against the test set with 21 charged compounds.

| Compound ID | Exp. ΔGsolv | KMTISM Result | MM-GBSA Result | MM-PBSA Result | Solute Name | Formula |
|---|---|---|---|---|---|---|
| | | | Anions | | | |
| i058 | −76.20 | −70.64 | −70.46 | −71.79 | formicacid | H1C1O2 |
| i059 | −77.60 | −70.58 | −63.33 | −65.10 | aceticacid | H3C2O2 |
| i060 | −76.20 | −70.91 | −63.15 | −64.37 | propanoicacid | H5C3O2 |
| i061 | −74.60 | −71.64 | −60.41 | −61.92 | hexanoicacid | H11C6O2 |
| i062 | −74.00 | −71.58 | −60.06 | −61.48 | acrylicacid | H3C3O2 |
| i063 | −68.50 | −71.63 | −63.81 | −65.94 | pyruvicacid | H3C3O3 |
| i064 | −71.20 | −73.01 | −80.95 | −82.23 | benzoicacid | H5C7O2 |
| i118 | −59.30 | −67.87 | −79.96 | −80.54 | trifluoroaceticacid | C2O2F3 |
| i119 | −69.70 | −70.83 | −61.19 | −63.11 | chloroaceticacid | H2C2O2CL1 |
| i120 | −62.30 | −70.91 | −63.45 | −65.44 | dichloroaceticacid | H1C2O2CL2 |
| | | | Cations | | | |
| i003 | −76.40 | −78.40 | −62.95 | −64.91 | methylamine | H6C1N1 |
| i004 | −71.50 | −78.92 | −91.16 | −87.52 | n-propylamine | H10C3N1 |
| i008 | −72.00 | −79.70 | −86.92 | −83.96 | allylamine | H8C3N1 |
| i020 | −69.60 | −71.13 | −84.68 | −81.80 | 3-methylaniline | H10C7N1 |
| i021 | −69.80 | −71.18 | −82.01 | −79.25 | 4-methylaniline | H10C7N1 |
| i023 | −65.80 | −72.90 | −81.93 | −79.18 | 3-aminoaniline | H9C6N2 |
| i047 | −85.20 | −90.16 | −84.38 | −79.84 | ammonia | H4N1 |
| i048 | −84.60 | −80.59 | −80.98 | −78.91 | hydrazine | H5N2 |
| i093 | −71.20 | −82.26 | −70.80 | −67.26 | 4-methoxyaniline | H10C7N1O1 |
| i125 | −74.70 | −80.74 | −80.29 | −77.73 | 3-chloroaniline | H7C6N1CL1 |
| i126 | −74.10 | −80.70 | −74.39 | −71.60 | 4-chloroaniline | H7C6N1CL1 |

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the invention not be limited to the particular embodiment disclosed as the best mode contemplated for carrying out this disclosure.

What is claimed:

1. A computer-implemented method of simulating free energy change with respect to one or a series of molecules, comprising:

determining, using a hardware computer processor, atom pairwise contacts between a first molecule structure and a second molecule structure that comprise a two-molecule system;

sampling, using the computer processor, atom energy for the two-molecule system and constructing an atom-energy matrix for the first molecule and an atom-energy matrix for the second molecule;

converting the atom energy matrix for the first molecule into a molecular energy matrix for the first molecule;

converting the atom energy matrix for the second molecule into a molecular energy matrix for the second molecule;

converting energy values of the molecular energy matrix for the first molecule to Boltzman factors under room temperature; and converting energy values of the molecular energy matrix for the second molecule to Boltzman factors under room temperature;

using the Boltzman factors, calculating Boltzmann free energy (A);

$$A = -RT\ln[Z_M] = -RT\ln\left[\int_D e^{-\beta E_M(\tau)} d\tau\right] \approx -RT\ln\left[V\frac{\sum_i^N e^{-\beta E_i(r)}}{N}\right]$$

where:
R is the gas constant;
T is temperature in degrees Kelvin (optionally 298.15 K);
Z is the partition function, which is the sum of the Boltzman factors;
D is a defined volume quantity representing the three dimensional space that particles under study should be contained;
M is a subscription meaning "molecular";
$\beta$ is 1/(RT);
E is the energy;
V is the ensemble volume; and
N is the number of states that have been sampled;
using Monte Carlo Integration by a method that comprises calculating an estimate of the ensemble volume V according to the equation:

$$V = 2^{Y-4} \times (2\pi)^{Y-3} \times (4\pi)^{Y-2} C^{Y-1}$$

where:
C a constant representing a predetermined boundary of the particle-particle distance in the ensemble, and
Y is the number of atoms in the ensemble.

2. The method of claim 1 wherein the first molecule is a protein molecule, the second molecule is a ligand molecule, and the two-molecule system is a protein-ligand system.

3. The method of claim 1 wherein determining atom pairwise contacts between the first molecule structure and the second molecule structure comprises calculating atom pairwise contacts in a first molecule structure and atom pairwise contacts in a second molecule structure of the two-molecule system.

4. The method of claim 1 further comprising storing, via at least one hardware computer processor, a first atom input structure file for the first molecule and a second atom input structure file for the second molecule.

5. The method of claim 4 further comprising storing, via the at least one hardware computer processor, a data structure comprising all possible atom type combinations in a two-molecule system and their associated pairwise distant dependent energies in solution.

6. The method of claim 5 further comprising determining first molecule structural information from the first molecule structure input file and determining second molecule structural information from the second molecule structure input file.

7. The method of claim 6 further comprising collecting the atoms that have a significant contact between the first molecule structure and the second molecule structure within a predetermined distance from each other.

8. The method of claim 1 further comprising calculating the partition functions of the two molecule system in both a free state and a bind-state.

9. The method of claim 1, further comprising performing determining, sampling, converting, and calculating steps with the first molecule structure and a series of second molecule structures.

10. The method of claim 9, further comprising selecting a two-molecule system and measuring an experimental binding affinity for the two-molecule system.

11. One or more computer-readable hardware storage device having embedded therein a set of instructions which, when executed by one or more processors of a computer, causes the computer to execute operations comprising:
determining atom pairwise contacts between a first molecule structure and a second molecule structure that comprise a two-molecule system;
sampling, using the one or more processors, atom energy for the two-molecule system and constructing an atom-energy matrix for the first molecule and an atom-energy matrix for the second molecule;
converting the atom energy matrix for the first molecule into a molecular energy matrix for the first molecule;
converting the atom energy matrix for the second molecule into a molecular energy matrix for the second molecule;
converting energy values of the molecular energy matrix for the first molecule to Boltzman factors under room temperature;
converting energy values of the molecular energy matrix for the second molecule to Boltzman factors under room temperature; and
using the Boltzman factors, calculating Boltzmann free energy (A):

$$A = -RT\ln[Z_M] = -RT\ln\left[\int_D e^{-\beta E_M(\tau)} d\tau\right] \approx -RT\ln\left[V\frac{\sum_i^N e^{-\beta E_i(r)}}{N}\right]$$

where:
R is the gas constant;
T is temperature in degrees Kelvin (optionally 298.15 K);
Z is the partition function, which is the sum of the Boltzman factors;
D is a defined volume quantity representing the three dimensional space that particles under study should be contained;
M is a subscription meaning "molecular";
$\beta$ is 1/(RT);
E is the energy;
V is the ensemble volume; and
N is the number of states that have been sampled;
using Monte Carlo Integration by a method that comprises calculating an estimate of the ensemble volume V according to the equation:

$$V = 2^{Y-4} \times (2\pi)^{Y-3} \times (4\pi)^{Y-2} C^{Y-1}$$

where:
C a constant representing a predetermined boundary of the particle-particle distance in the ensemble, and
Y is the number of atoms in the ensemble.

12. The one or more computer-readable hardware storage device of claim 11 wherein the first molecule is a protein molecule, the second molecule is a ligand molecule, and the two-molecule system is a protein-ligand system.

13. The one or more computer-readable hardware storage device of claim 11 wherein determining atom pairwise contacts between the first molecule structure and the second molecule structure comprises calculating atom pairwise contacts in a first molecule structure and atom pairwise contacts in a second molecule structure of the two-molecule system.

14. The one or more computer-readable hardware storage device of claim 11, the operations further comprising storing a first atom input structure file for the first molecule and a second atom input structure file for the second molecule.

15. The one or more computer-readable hardware storage device of claim 14, the operations further comprising storing a data structure comprising all possible atom type combinations in the two-molecule system and their associated pairwise distant dependent energies in solution.

16. The puter-readable hardware storage device of claim 15, the operations further comprising determining first molecule structural information from the first molecule structure input file and determining second molecule structural information from the second molecule structure input file.

17. The one or more computer-readable hardware storage device claim 16, the operations further comprising collecting the atoms that have a significant contact between the first molecule structure and the second molecule structure within a predetermined distance from each other.

18. The one or more computer-readable hardware storage device of claim 11, the operations further comprising calculating the partition functions of the two molecule system in both a free state and a bind-state.

19. A system comprising one or more computer processor configured to:
  determine atom pairwise contacts between a first molecule structure and a second molecule structure that comprise a two-molecule system;
  sample atom energy for the two-molecule system and construct an atom-energy matrix or the first molecule and an atom-energy matrix for the second molecule;
  convert the atom energy matrix for the first molecule into a molecular energy matrix for the first molecule;
  convert the atoms energy matrix for the second molecule into a molecular energy matrix for the second molecule;
  convert energy values of the molecular energy matrix for the first molecule to Boltzman factors under room temperature;
  convert energy values of the molecular energy matrix for the second molecule to Boltzman factors under room temperature; and
  using the Boltzman factors, calculate Boltzmann free energy (A):

$$A = -RT\ln[Z_M] = -RT\ln\left[\int_D e^{-\beta E_M(\tau)}d\tau\right] \approx -RT\ln\left[V\frac{\sum_i^N e^{-\beta E_i(r)}}{N}\right]$$

where
  R is the gas constant;
  T is temperature in degrees Kelvin (optionally 298.15 K);
  Z is the partition function, which is the sum of the Boltzman factors;

D is a defined volume quantity representing the three dimensional space that particles under study should be contained;
  M is a subscription meaning "molecular";
  B is 1/(RT);
  E is the energy;
  V is the ensemble volume; and
  N is the number of states that have been sampled;
using Monte Carlo Integration by a method that comprises calculation of an estimate of the ensemble volume V according to the equation:

$$V = 2^{Y-4} \times (2\pi)^{Y-3} \times (4\pi)^{Y-2} C^{Y-1}$$

where:
  C a constant representing a predetermined boundary of the particle-particle distance in the ensemble, and
  Y is the number of atoms in the ensemble.

20. The system of claim 19 wherein the first molecule is a protein molecule, the second molecule is a ligand molecule, and the two-molecule system is a protein-ligand system.

21. The system of claim 19 wherein determination of atom pairwise contacts between the first molecule structure and the second molecule structure comprises calculation of atom pairwise contacts in a first molecule structure and atom pairwise contact a second molecule structure of the two-molecule system.

22. The system of claim 19, the one or more hardware computer processor further configured to store a first atom input structure file for the first molecule and to store a second atom input structure file for the second molecule.

23. The system of claim 22, the one or more hardware computer processor further configured to store a data structure comprising all possible atom type combinations in the two-molecule system and their associated pairwise distant dependent energies in solution.

24. The system of claim 23, the one or more hardware computer processor further configured to determine first molecule structural information from a first molecule structure input file and to determine second molecule structural information from a second molecule structure input file.

25. The system of claim 24, the one or more hardware computer processor further configured to collect atoms that have a significant contact between the first molecule structure and the second molecule structure within a predetermined distance from each other.

26. The system of claim 19, the one or more hardware computer processor further configured to calculate the partition functions of the two molecule system in both a free state and a bind-state.

* * * * *

UNITED STATES PATENT AND TRADEMARK OFFICE
CERTIFICATE OF CORRECTION

PATENT NO. : 10,332,616 B2
APPLICATION NO. : 15/143519
DATED : June 25, 2019
INVENTOR(S) : Zheng et al.

Page 1 of 1

It is certified that error appears in the above-identified patent and that said Letters Patent is hereby corrected as shown below:

In the Claims

Column 64, Line 62, Claim 1, after "and", insert --¶--

Column 64, Line 66, Claim 1, delete "(A);" and insert --(A):-- therefor

Column 67, Line 8, Claim 16, delete "puter-readable" and insert --one or more computer-readable-- therefor Column 67, Line 14, Claim 17, after "device", insert --of--

Column 67, Line 22, Claim 19, after "more", insert --hardware--

Column 67, Line 28, Claim 19, delete "or" and insert --for-- therefor

Column 67, Line 32, Claim 19, delete "atoms" and insert --atom-- therefor

Column 67, Line 50, Claim 19, delete "where" and insert --where:-- therefor

Column 68, Line 5, Claim 19, delete "B" and insert --β-- therefor

Column 68, Line 29, Claim 21, after "contact", insert --in--

Signed and Sealed this
Fourteenth Day of April, 2020

Andrei Iancu
*Director of the United States Patent and Trademark Office*